(12) United States Patent
Kanda et al.

(10) Patent No.: US 8,501,914 B2
(45) Date of Patent: Aug. 6, 2013

(54) RECOMBINANT PROTEIN S COMPOSITION

(75) Inventors: Yutaka Kanda, Tokyo (JP); Hiroshi Sato, Tokyo (JP); Tsuyoshi Yamada, Tokyo (JP); Akifumi Kato, Tokyo (JP); Mitsuo Satoh, Tokyo (JP)

(73) Assignee: Kyowa Hakko Kirin Co., Ltd, Tokyo (JP)

( * ) Notice: Subject to any disclaimer, the term of this patent is extended or adjusted under 35 U.S.C. 154(b) by 839 days.

(21) Appl. No.: 12/540,501

(22) Filed: Aug. 13, 2009

(65) Prior Publication Data

US 2010/0162418 A1 Jun. 24, 2010

Related U.S. Application Data

(60) Provisional application No. 61/089,271, filed on Aug. 15, 2008.

(30) Foreign Application Priority Data

Aug. 13, 2008 (JP) ................................ P2008-208384

(51) Int. Cl.
*A61K 38/16* (2006.01)
*C12P 21/02* (2006.01)

(52) U.S. Cl.
USPC .......................................... 530/380; 435/70.1

(58) Field of Classification Search
None
See application file for complete search history.

(56) References Cited

U.S. PATENT DOCUMENTS

2004/0110704 A1 6/2004 Yamane et al.

OTHER PUBLICATIONS

Kennell, D., Progr. Nucleic Acid Res. Mol. Biol. 11:259-301, 1971.*
Ngo, in the Protein Folding Problem and Tertiary Structure Prediction, Merz et al. (eds.), Birkhauser Boston: Boston, MA, pp. 433 and 492-495, 1994.*
Rudinger (in Peptide Hormones, Parsons (ed.), University Park Press: Baltimore, MD, pp. 1-7, 1976.*
Hryszko, T. et al., "Protein S attenuates the invasive potential of THP-1 cells by interfering with plasminogen binding on cell surface via a protein C-independent mechanism", FEBS Letters, 2005, vol. 579, p. 6023-6026.
Rezende, S. M. et al., "Coagulation, inflammation, and apoptosis: different roles for protein S and the protein S-C4b binding protein complex", Blood, 2004, vol. 103, No. 4, p. 1192-1201.
Morboeuf, O. et al., "Expression and Characterization of Recombinant Protein S with the Ser 460 Pro Mutation", Thrombosis Research, 2000, vol. 100, p. 81-88.
Hoskins, J. et al., "Cloning and characterization of human liver cDNA encoding a protein S precursor", Proc. Natl. Acad. Sci. USA., 1987, vol. 84, p. 349-353.
Dahlback, B., "The tale of protein S and C4b-binding protein, a story of affection", Thrombosis and Haemostasis, 2007, vol. 98, p. 90-96.
Bopp, C. et al., "sRAGE is Elevated in Septic Patients and Associated With Patients Outcome", Journal of Surgical Research, Jun. 2008, vol. 147, p. 79-83.
Yamane-Ohnuki, N. et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity", Biotechnology and Bioengineering, 2004, vol. 87, No. 5, p. 614-622.

* cited by examiner

*Primary Examiner* — Michael Burkhart
(74) *Attorney, Agent, or Firm* — Sughrue Mion, PLLC

(57) ABSTRACT

A pharmaceutical agent for treating a disease such as inflammatory diseases, blood coagulation diseases associated with deficiency of Protein S has been required. The present invention provides a Protein S composition comprising recombinant Protein S molecules having complex type N-glycoside-linked sugar chains, wherein the Protein S has a higher binding activity to a receptor for advanced glycation end products (hereinafter referred to as "RAGE") than native Protein S present in healthy human blood, and also has a higher ratio of sugar chains in which fucose is not bound to the complex type N-glycoside-linked sugar chains bound to Protein S than native Protein S present in healthy human blood.

14 Claims, 11 Drawing Sheets

SEQUENCE LISTING

```
<160> NUMBER OF SEQ ID NOS: 8

<210> SEQ ID NO 1
<211> LENGTH: 2031
<212> TYPE: DNA
<213> ORGANISM: Homo sapiens
<220> FEATURE:
<221> NAME/KEY: CDS
<222> LOCATION: (1)..(2031)

<400> SEQUENCE: 1 atg agg gtc ctg ggt ggg cgc tgc ggg gcg ctg ctg gcg tgt ctc ctc        48
Met Arg Val Leu Gly Gly Arg Cys Gly Ala Leu Leu Ala Cys Leu Leu
1               5                   10                  15 cta gtg ctt ccc gtc tca gag gca aac ttt ttg tca aag caa cag gct        96
Leu Val Leu Pro Val Ser Glu Ala Asn Phe Leu Ser Lys Gln Gln Ala
            20                  25                  30 tca caa gtc ctg gtt agg aag cgt cgt gca aat tct tta ctt gaa gaa       144
Ser Gln Val Leu Val Arg Lys Arg Arg Ala Asn Ser Leu Leu Glu Glu
        35                  40                  45 acc aaa cag ggt aat ctt gaa aga gaa tgc atc gaa gaa ctg tgc aat       192
Thr Lys Gln Gly Asn Leu Glu Arg Glu Cys Ile Glu Glu Leu Cys Asn
    50                  55                  60 aaa gaa gaa gcc agg gag gtc ttt gaa aat gac ccg gaa acg gat tat       240
Lys Glu Glu Ala Arg Glu Val Phe Glu Asn Asp Pro Glu Thr Asp Tyr
65                  70                  75                  80 ttt tat cca aaa tac tta gtt tgt ctt cgc tct ttt caa act ggg tta       288
Phe Tyr Pro Lys Tyr Leu Val Cys Leu Arg Ser Phe Gln Thr Gly Leu
                85                  90                  95 ttc act gct gca cgt cag tca act aat gct tat cct gac cta aga agc       336
Phe Thr Ala Ala Arg Gln Ser Thr Asn Ala Tyr Pro Asp Leu Arg Ser
            100                 105                 110 tgt gtc aat gcc att cca gac cag tgt agt cct ctg cca tgc aat gaa       384
Cys Val Asn Ala Ile Pro Asp Gln Cys Ser Pro Leu Pro Cys Asn Glu
        115                 120                 125 gat gga tat atg agc tgc aaa gat gga aaa gct tct ttt act tgc act       432
Asp Gly Tyr Met Ser Cys Lys Asp Gly Lys Ala Ser Phe Thr Cys Thr
    130                 135                 140 tgt aaa cca ggt tgg caa gga gaa aag tgt gaa ttt gac ata aat gaa       480
Cys Lys Pro Gly Trp Gln Gly Glu Lys Cys Glu Phe Asp Ile Asn Glu
145                 150                 155                 160 tgc aaa gat ccc tca aat ata aat gga ggt tgc agt caa att tgt gat       528
```

```
                        -continued

Cys Lys Asp Pro Ser Asn Ile Asn Gly Gly Cys Ser Gln Ile Cys Asp
                          165                 170                 175 aat aca cct gga agt tac cac tgt tcc tgt aaa aat ggt ttt gtt atg       576
Asn Thr Pro Gly Ser Tyr His Cys Ser Cys Lys Asn Gly Phe Val Met
                180                 185                 190 ctt tca aat aag aaa gat tgt aaa gat gtg gat gaa tgc tct ttg aag       624
Leu Ser Asn Lys Lys Asp Cys Lys Asp Val Asp Glu Cys Ser Leu Lys
            195                 200                 205 cca agc att tgt ggc aca gct gtg tgc aag aac atc cca gga gat ttt       672
Pro Ser Ile Cys Gly Thr Ala Val Cys Lys Asn Ile Pro Gly Asp Phe
        210                 215                 220 gaa tgt gaa tgc ccc gaa ggc tac aga tat aat ctc aaa tca aag tct       720
Glu Cys Glu Cys Pro Glu Gly Tyr Arg Tyr Asn Leu Lys Ser Lys Ser
225                 230                 235                 240 tgt gaa gat ata gat gaa tgc tct gag aac atg tgt gct cag ctt tgt       768
Cys Glu Asp Ile Asp Glu Cys Ser Glu Asn Met Cys Ala Gln Leu Cys
                245                 250                 255 gtc aat tac cct gga ggt tac act tgc tat tgt gat ggg aag aaa gga       816
Val Asn Tyr Pro Gly Gly Tyr Thr Cys Tyr Cys Asp Gly Lys Lys Gly
                260                 265                 270 ttc aaa ctt gcc caa gat cag aag agt tgt gag gtt gtt tca gtg tgc       864
Phe Lys Leu Ala Gln Asp Gln Lys Ser Cys Glu Val Val Ser Val Cys
            275                 280                 285 ctt ccc ttg aac ctt gac aca aag tat gaa tta ctt tac ttg gcg gag       912
Leu Pro Leu Asn Leu Asp Thr Lys Tyr Glu Leu Leu Tyr Leu Ala Glu
        290                 295                 300 cag ttt gca ggg gtt gtt tta tat tta aaa ttt cgt ttg cca gaa atc       960
Gln Phe Ala Gly Val Val Leu Tyr Leu Lys Phe Arg Leu Pro Glu Ile
305                 310                 315                 320 agc aga ttt tca gca gaa ttt gat ttc cgg aca tat gat tca gaa ggc      1008
Ser Arg Phe Ser Ala Glu Phe Asp Phe Arg Thr Tyr Asp Ser Glu Gly
                325                 330                 335 gtg ata ctg tac gca gaa tct atc gat cac tca gcg tgg ctc ctg att      1056
Val Ile Leu Tyr Ala Glu Ser Ile Asp His Ser Ala Trp Leu Leu Ile
                340                 345                 350 gca ctt cgt ggt gga aag att gaa gtt cag ctt aag aat gaa cat aca      1104
Ala Leu Arg Gly Gly Lys Ile Glu Val Gln Leu Lys Asn Glu His Thr
            355                 360                 365 tcc aaa atc aca act gga ggt gat gtt att aat aat ggt cta tgg aat      1152
Ser Lys Ile Thr Thr Gly Gly Asp Val Ile Asn Asn Gly Leu Trp Asn
        370                 375                 380 atg gtg tct gtg gaa gaa tta gaa cat agt att agc att aaa ata gct      1200
Met Val Ser Val Glu Glu Leu Glu His Ser Ile Ser Ile Lys Ile Ala
385                 390                 395                 400 aaa gaa gct gtg atg gat ata aat aaa cct gga ccc ctt ttt aag ccg      1248
Lys Glu Ala Val Met Asp Ile Asn Lys Pro Gly Pro Leu Phe Lys Pro
                405                 410                 415 gaa aat gga ttg ctg gaa acc aaa gta tac ttt gca gga ttc cct cgg      1296
Glu Asn Gly Leu Leu Glu Thr Lys Val Tyr Phe Ala Gly Phe Pro Arg
                420                 425                 430 aaa gtg gaa agt gaa ctc att aaa ccg att aac cct cgt cta gat gga      1344
Lys Val Glu Ser Glu Leu Ile Lys Pro Ile Asn Pro Arg Leu Asp Gly
            435                 440                 445 tgt ata cga agc tgg aat ttg atg aag caa gga gct tct gga ata aag      1392
Cys Ile Arg Ser Trp Asn Leu Met Lys Gln Gly Ala Ser Gly Ile Lys
        450                 455                 460 gaa att att caa gaa aaa caa aat aag cat tgc ctg gtt act gtg gag      1440
Glu Ile Ile Gln Glu Lys Gln Asn Lys His Cys Leu Val Thr Val Glu
465                 470                 475                 480 aag ggc tcc tac tat cct ggt tct gga att gct caa ttt cac ata gat      1488
```

-continued

```
                Lys Gly Ser Tyr Tyr Pro Gly Ser Gly Ile Ala Gln Phe His Ile Asp
                                485                 490                 495 tat aat aat gta tcc agt gct gag ggt tgg cat gta aat gtg acc ttg         1536
Tyr Asn Asn Val Ser Ser Ala Glu Gly Trp His Val Asn Val Thr Leu
                500                 505                 510 aat att cgt cca tcc acg ggc act ggt gtt atg ctt gcc ttg gtt tct         1584
Asn Ile Arg Pro Ser Thr Gly Thr Gly Val Met Leu Ala Leu Val Ser
                515                 520                 525 ggt aac aac aca gtg ccc ttt gct gtg tcc ttg gtg gac tcc acc tct         1632
Gly Asn Asn Thr Val Pro Phe Ala Val Ser Leu Val Asp Ser Thr Ser
        530                 535                 540 gaa aaa tca cag gat att ctg tta tct gtt gaa aat act gta ata tat         1680
Glu Lys Ser Gln Asp Ile Leu Leu Ser Val Glu Asn Thr Val Ile Tyr
545                 550                 555                 560 cgg ata cag gcc cta agt cta tgt tcc gat caa caa tct cat ctg gaa         1728
Arg Ile Gln Ala Leu Ser Leu Cys Ser Asp Gln Gln Ser His Leu Glu
                565                 570                 575 ttt aga gtc aac aga aac aat ctg gag ttg tcg aca cca ctt aaa ata         1776
Phe Arg Val Asn Arg Asn Asn Leu Glu Leu Ser Thr Pro Leu Lys Ile
                580                 585                 590 gaa acc atc tcc cat gaa gac ctt caa aga caa ctt gcc gtc ttg gac         1824
Glu Thr Ile Ser His Glu Asp Leu Gln Arg Gln Leu Ala Val Leu Asp
                595                 600                 605 aaa gca atg aaa gca aaa gtg gcc aca tac ctg ggt ggc ctt cca gat         1872
Lys Ala Met Lys Ala Lys Val Ala Thr Tyr Leu Gly Gly Leu Pro Asp
        610                 615                 620 gtt cca ttc agt gcc aca cca gtg aat gcc ttt tat aat ggc tgc atg         1920
Val Pro Phe Ser Ala Thr Pro Val Asn Ala Phe Tyr Asn Gly Cys Met
625                 630                 635                 640 gaa gtg aat att aat ggt gta cag ttg gat ctg gat gaa gcc att tct         1968
Glu Val Asn Ile Asn Gly Val Gln Leu Asp Leu Asp Glu Ala Ile Ser
                645                 650                 655 aaa cat aat gat att aga gct cac tca tgt cca tca gtt tgg aaa aag         2016
Lys His Asn Asp Ile Arg Ala His Ser Cys Pro Ser Val Trp Lys Lys
                660                 665                 670 aca aag aat tct taa                                                     2031
Thr Lys Asn Ser
        675

<210> SEQ ID NO 2
<211> LENGTH: 676
<212> TYPE: PRT
<213> ORGANISM: Homo sapiens

<400> SEQUENCE: 2

Met Arg Val Leu Gly Gly Arg Cys Gly Ala Leu Leu Ala Cys Leu Leu
1               5                   10                  15

Leu Val Leu Pro Val Ser Glu Ala Asn Phe Leu Ser Lys Gln Gln Ala
                20                  25                  30

Ser Gln Val Leu Val Arg Lys Arg Ala Asn Ser Leu Leu Glu Glu
            35                  40                  45

Thr Lys Gln Gly Asn Leu Glu Arg Glu Cys Ile Glu Glu Leu Cys Asn
    50                  55                  60

Lys Glu Glu Ala Arg Glu Val Phe Glu Asn Asp Pro Glu Thr Asp Tyr
65                  70                  75                  80

Phe Tyr Pro Lys Tyr Leu Val Cys Leu Arg Ser Phe Gln Thr Gly Leu
                85                  90                  95

Phe Thr Ala Ala Arg Gln Ser Thr Asn Ala Tyr Pro Asp Leu Arg Ser
                100                 105                 110
```

-continued

```
Cys Val Asn Ala Ile Pro Asp Gln Cys Ser Pro Leu Pro Cys Asn Glu
            115                 120                 125

Asp Gly Tyr Met Ser Cys Lys Asp Gly Lys Ala Ser Phe Thr Cys Thr
130                 135                 140

Cys Lys Pro Gly Trp Gln Gly Glu Lys Cys Glu Phe Asp Ile Asn Glu
145                 150                 155                 160

Cys Lys Asp Pro Ser Asn Ile Asn Gly Gly Cys Ser Gln Ile Cys Asp
            165                 170                 175

Asn Thr Pro Gly Ser Tyr His Cys Ser Cys Lys Asn Gly Phe Val Met
            180                 185                 190

Leu Ser Asn Lys Lys Asp Cys Lys Asp Val Asp Glu Cys Ser Leu Lys
            195                 200                 205

Pro Ser Ile Cys Gly Thr Ala Val Cys Lys Asn Ile Pro Gly Asp Phe
210                 215                 220

Glu Cys Glu Cys Pro Glu Gly Tyr Arg Tyr Asn Leu Lys Ser Lys Ser
225                 230                 235                 240

Cys Glu Asp Ile Asp Glu Cys Ser Glu Asn Met Cys Ala Gln Leu Cys
            245                 250                 255

Val Asn Tyr Pro Gly Gly Tyr Thr Cys Tyr Cys Asp Gly Lys Lys Gly
            260                 265                 270

Phe Lys Leu Ala Gln Asp Gln Lys Ser Cys Glu Val Val Ser Val Cys
            275                 280                 285

Leu Pro Leu Asn Leu Asp Thr Lys Tyr Glu Leu Leu Tyr Leu Ala Glu
            290                 295                 300

Gln Phe Ala Gly Val Val Leu Tyr Leu Lys Phe Arg Leu Pro Glu Ile
305                 310                 315                 320

Ser Arg Phe Ser Ala Glu Phe Asp Phe Arg Thr Tyr Asp Ser Glu Gly
            325                 330                 335

Val Ile Leu Tyr Ala Glu Ser Ile Asp His Ser Ala Trp Leu Leu Ile
            340                 345                 350

Ala Leu Arg Gly Gly Lys Ile Glu Val Gln Leu Lys Asn Glu His Thr
            355                 360                 365

Ser Lys Ile Thr Thr Gly Gly Asp Val Ile Asn Asn Gly Leu Trp Asn
370                 375                 380

Met Val Ser Val Glu Glu Leu Glu His Ser Ile Ser Ile Lys Ile Ala
385                 390                 395                 400

Lys Glu Ala Val Met Asp Ile Asn Lys Pro Gly Pro Leu Phe Lys Pro
            405                 410                 415

Glu Asn Gly Leu Leu Glu Thr Lys Val Tyr Phe Ala Gly Phe Pro Arg
            420                 425                 430

Lys Val Glu Ser Glu Leu Ile Lys Pro Ile Asn Pro Arg Leu Asp Gly
            435                 440                 445

Cys Ile Arg Ser Trp Asn Leu Met Lys Gln Gly Ala Ser Gly Ile Lys
450                 455                 460

Glu Ile Ile Gln Glu Lys Gln Asn Lys His Cys Leu Val Thr Val Glu
465                 470                 475                 480

Lys Gly Ser Tyr Tyr Pro Gly Ser Gly Ile Ala Gln Phe His Ile Asp
            485                 490                 495

Tyr Asn Asn Val Ser Ser Ala Glu Gly Trp His Val Asn Val Thr Leu
            500                 505                 510

Asn Ile Arg Pro Ser Thr Gly Thr Gly Val Met Leu Ala Leu Val Ser
            515                 520                 525

Gly Asn Asn Thr Val Pro Phe Ala Val Ser Leu Val Asp Ser Thr Ser
530                 535                 540
```

```
Glu Lys Ser Gln Asp Ile Leu Leu Ser Val Glu Asn Thr Val Ile Tyr
545                 550                 555                 560

Arg Ile Gln Ala Leu Ser Leu Cys Ser Asp Gln Gln Ser His Leu Glu
                565                 570                 575

Phe Arg Val Asn Arg Asn Asn Leu Glu Leu Ser Thr Pro Leu Lys Ile
            580                 585                 590

Glu Thr Ile Ser His Glu Asp Leu Gln Arg Gln Leu Ala Val Leu Asp
        595                 600                 605

Lys Ala Met Lys Ala Lys Val Ala Thr Tyr Leu Gly Leu Pro Asp
    610                 615                 620

Val Pro Phe Ser Ala Thr Pro Val Asn Ala Phe Tyr Asn Gly Cys Met
625                 630                 635                 640

Glu Val Asn Ile Asn Gly Val Gln Leu Asp Leu Asp Glu Ala Ile Ser
                645                 650                 655

Lys His Asn Asp Ile Arg Ala His Ser Cys Pro Ser Val Trp Lys Lys
            660                 665                 670

Thr Lys Asn Ser
        675

<210> SEQ ID NO 3
<211> LENGTH: 37
<212> TYPE: DNA
<213> ORGANISM: Artificial
<220> FEATURE:
<223> OTHER INFORMATION: Description of artificial sequence : protein S
      5'-primer

<400> SEQUENCE: 3
cgcgtacgga cccctcacca tgagggtcct gggtggg                            37

<210> SEQ ID NO 4
<211> LENGTH: 31
<212> TYPE: DNA
<213> ORGANISM: Artificial
<220> FEATURE:
<223> OTHER INFORMATION: Description of artificial sequence : protein S
      3'-primer

<400> SEQUENCE: 4
ggggatcctt aagaattctt tgtcttttc c                                   31

<210> SEQ ID NO 5
<211> LENGTH: 1959
<212> TYPE: DNA
<213> ORGANISM: Homo sapiens
<220> FEATURE:
<221> NAME/KEY: CDS
<222> LOCATION: (1)..(1959)

<400> SEQUENCE: 5 aac ttt ttg tca aag caa cag gct tca caa gtc ctg gtt agg aag cgt    48
Asn Phe Leu Ser Lys Gln Gln Ala Ser Gln Val Leu Val Arg Lys Arg
1               5                   10                  15 cgt gca aat tct tta ctt gaa gaa acc aaa cag ggt aat ctt gaa aga    96
Arg Ala Asn Ser Leu Leu Glu Glu Thr Lys Gln Gly Asn Leu Glu Arg
            20                  25                  30 gaa tgc atc gaa gaa ctg tgc aat aaa gaa gaa gcc agg gag gtc ttt   144
Glu Cys Ile Glu Glu Leu Cys Asn Lys Glu Glu Ala Arg Glu Val Phe
        35                  40                  45 gaa aat gac ccg gaa acg gat tat ttt tat cca aaa tac tta gtt tgt   192
Glu Asn Asp Pro Glu Thr Asp Tyr Phe Tyr Pro Lys Tyr Leu Val Cys
    50                  55                  60
```

```
                                                            -continued ctt cgc tct ttt caa act ggg tta ttc act gct gca cgt cag tca act      240
Leu Arg Ser Phe Gln Thr Gly Leu Phe Thr Ala Ala Arg Gln Ser Thr
 65                  70                  75                  80 aat gct tat cct gac cta aga agc tgt gtc aat gcc att cca gac cag      288
Asn Ala Tyr Pro Asp Leu Arg Ser Cys Val Asn Ala Ile Pro Asp Gln
                 85                  90                  95 tgt agt cct ctg cca tgc aat gaa gat gga tat atg agc tgc aaa gat      336
Cys Ser Pro Leu Pro Cys Asn Glu Asp Gly Tyr Met Ser Cys Lys Asp
            100                 105                 110 gga aaa gct tct ttt act tgc act tgt aaa cca ggt tgg caa gga gaa      384
Gly Lys Ala Ser Phe Thr Cys Thr Cys Lys Pro Gly Trp Gln Gly Glu
        115                 120                 125 aag tgt gaa ttt gac ata aat gaa tgc aaa gat ccc tca aat ata aat      432
Lys Cys Glu Phe Asp Ile Asn Glu Cys Lys Asp Pro Ser Asn Ile Asn
    130                 135                 140 gga ggt tgc agt caa att tgt gat aat aca cct gga agt tac cac tgt      480
Gly Gly Cys Ser Gln Ile Cys Asp Asn Thr Pro Gly Ser Tyr His Cys
145                 150                 155                 160 tcc tgt aaa aat ggt ttt gtt atg ctt tca aat aag aaa gat tgt aaa      528
Ser Cys Lys Asn Gly Phe Val Met Leu Ser Asn Lys Lys Asp Cys Lys
                165                 170                 175 gat gtg gat gaa tgc tct ttg aag cca agc att tgt ggc aca gct gtg      576
Asp Val Asp Glu Cys Ser Leu Lys Pro Ser Ile Cys Gly Thr Ala Val
            180                 185                 190 tgc aag aac atc cca gga gat ttt gaa tgt gaa tgc ccc gaa ggc tac      624
Cys Lys Asn Ile Pro Gly Asp Phe Glu Cys Glu Cys Pro Glu Gly Tyr
        195                 200                 205 aga tat aat ctc aaa tca aag tct tgt gaa gat ata gat gaa tgc tct      672
Arg Tyr Asn Leu Lys Ser Lys Ser Cys Glu Asp Ile Asp Glu Cys Ser
    210                 215                 220 gag aac atg tgt gct cag ctt tgt gtc aat tac cct gga ggt tac act      720
Glu Asn Met Cys Ala Gln Leu Cys Val Asn Tyr Pro Gly Gly Tyr Thr
225                 230                 235                 240 tgc tat tgt gat ggg aag aaa gga ttc aaa ctt gcc caa gat cag aag      768
Cys Tyr Cys Asp Gly Lys Lys Gly Phe Lys Leu Ala Gln Asp Gln Lys
                245                 250                 255 agt tgt gag gtt gtt tca gtg tgc ctt ccc ttg aac ctt gac aca aag      816
Ser Cys Glu Val Val Ser Val Cys Leu Pro Leu Asn Leu Asp Thr Lys
            260                 265                 270 tat gaa tta ctt tac ttg gcg gag cag ttt gca ggg gtt gtt tta tat      864
Tyr Glu Leu Leu Tyr Leu Ala Glu Gln Phe Ala Gly Val Val Leu Tyr
        275                 280                 285 tta aaa ttt cgt ttg cca gaa atc agc aga ttt tca gca gaa ttt gat      912
Leu Lys Phe Arg Leu Pro Glu Ile Ser Arg Phe Ser Ala Glu Phe Asp
    290                 295                 300 ttc cgg aca tat gat tca gaa ggc gtg ata ctg tac gca gaa tct atc      960
Phe Arg Thr Tyr Asp Ser Glu Gly Val Ile Leu Tyr Ala Glu Ser Ile
305                 310                 315                 320 gat cac tca gcg tgg ctc ctg att gca ctt cgt ggt gga aag att gaa     1008
Asp His Ser Ala Trp Leu Leu Ile Ala Leu Arg Gly Gly Lys Ile Glu
                325                 330                 335 gtt cag ctt aag aat gaa cat aca tcc aaa atc aca act gga ggt gat     1056
Val Gln Leu Lys Asn Glu His Thr Ser Lys Ile Thr Thr Gly Gly Asp
            340                 345                 350 gtt att aat aat ggt cta tgg aat atg gtg tct gtg gaa gaa tta gaa     1104
Val Ile Asn Asn Gly Leu Trp Asn Met Val Ser Val Glu Glu Leu Glu
        355                 360                 365 cat agt att agc att aaa ata gct aaa gaa gct gtg atg gat ata aat     1152
His Ser Ile Ser Ile Lys Ile Ala Lys Glu Ala Val Met Asp Ile Asn
    370                 375                 380
```

```
aaa cct gga ccc ctt ttt aag ccg gaa aat gga ttg ctg gaa acc aaa      1200
Lys Pro Gly Pro Leu Phe Lys Pro Glu Asn Gly Leu Leu Glu Thr Lys
385                 390                 395                 400 gta tac ttt gca gga ttc cct cgg aaa gtg gaa agt gaa ctc att aaa      1248
Val Tyr Phe Ala Gly Phe Pro Arg Lys Val Glu Ser Glu Leu Ile Lys
            405                 410                 415 ccg att aac cct cgt cta gat gga tgt ata cga agc tgg aat ttg atg      1296
Pro Ile Asn Pro Arg Leu Asp Gly Cys Ile Arg Ser Trp Asn Leu Met
        420                 425                 430 aag caa gga gct tct gga ata aag gaa att att caa gaa aaa caa aat      1344
Lys Gln Gly Ala Ser Gly Ile Lys Glu Ile Ile Gln Glu Lys Gln Asn
    435                 440                 445 aag cat tgc ctg gtt act gtg gag aag ggc tcc tac tat cct ggt tct      1392
Lys His Cys Leu Val Thr Val Glu Lys Gly Ser Tyr Tyr Pro Gly Ser
450                 455                 460 gga att gct caa ttt cac ata gat tat aat aat gta tcc agt gct gag      1440
Gly Ile Ala Gln Phe His Ile Asp Tyr Asn Asn Val Ser Ser Ala Glu
465                 470                 475                 480 ggt tgg cat gta aat gtg acc ttg aat att cgt cca tcc acg ggc act      1488
Gly Trp His Val Asn Val Thr Leu Asn Ile Arg Pro Ser Thr Gly Thr
            485                 490                 495 ggt gtt atg ctt gcc ttg gtt tct ggt aac aac aca gtg ccc ttt gct      1536
Gly Val Met Leu Ala Leu Val Ser Gly Asn Asn Thr Val Pro Phe Ala
        500                 505                 510 gtg tcc ttg gtg gac tcc acc tct gaa aaa tca cag gat att ctg tta      1584
Val Ser Leu Val Asp Ser Thr Ser Glu Lys Ser Gln Asp Ile Leu Leu
    515                 520                 525 tct gtt gaa aat act gta ata tat cgg ata cag gcc cta agt cta tgt      1632
Ser Val Glu Asn Thr Val Ile Tyr Arg Ile Gln Ala Leu Ser Leu Cys
530                 535                 540 tcc gat caa caa tct cat ctg gaa ttt aga gtc aac aga aac aat ctg      1680
Ser Asp Gln Gln Ser His Leu Glu Phe Arg Val Asn Arg Asn Asn Leu
545                 550                 555                 560 gag ttg tcg aca cca ctt aaa ata gaa acc atc tcc cat gaa gac ctt      1728
Glu Leu Ser Thr Pro Leu Lys Ile Glu Thr Ile Ser His Glu Asp Leu
            565                 570                 575 caa aga caa ctt gcc gtc ttg gac aaa gca atg aaa gca aaa gtg gcc      1776
Gln Arg Gln Leu Ala Val Leu Asp Lys Ala Met Lys Ala Lys Val Ala
        580                 585                 590 aca tac ctg ggt ggc ctt cca gat gtt cca ttc agt gcc aca cca gtg      1824
Thr Tyr Leu Gly Gly Leu Pro Asp Val Pro Phe Ser Ala Thr Pro Val
    595                 600                 605 aat gcc ttt tat aat ggc tgc atg gaa gtg aat att aat ggt gta cag      1872
Asn Ala Phe Tyr Asn Gly Cys Met Glu Val Asn Ile Asn Gly Val Gln
610                 615                 620 ttg gat ctg gat gaa gcc att tct aaa cat aat gat att aga gct cac      1920
Leu Asp Leu Asp Glu Ala Ile Ser Lys His Asn Asp Ile Arg Ala His
625                 630                 635                 640 tca tgt cca tca gtt tgg aaa aag aca aag aat tct taa                  1959
Ser Cys Pro Ser Val Trp Lys Lys Thr Lys Asn Ser
            645                 650

<210> SEQ ID NO 6
<211> LENGTH: 652
<212> TYPE: PRT
<213> ORGANISM: Homo sapiens

<400> SEQUENCE: 6

Asn Phe Leu Ser Lys Gln Gln Ala Ser Gln Val Leu Val Arg Lys Arg
1               5                   10                  15
```

-continued

```
Arg Ala Asn Ser Leu Leu Glu Glu Thr Lys Gln Gly Asn Leu Glu Arg
            20                  25                  30
Glu Cys Ile Glu Glu Leu Cys Asn Lys Glu Glu Ala Arg Glu Val Phe
        35                  40                  45
Glu Asn Asp Pro Glu Thr Asp Tyr Phe Tyr Pro Lys Tyr Leu Val Cys
 50                  55                  60
Leu Arg Ser Phe Gln Thr Gly Leu Phe Thr Ala Ala Arg Gln Ser Thr
 65                  70                  75                  80
Asn Ala Tyr Pro Asp Leu Arg Ser Cys Val Asn Ala Ile Pro Asp Gln
                 85                  90                  95
Cys Ser Pro Leu Pro Cys Asn Glu Asp Gly Tyr Met Ser Cys Lys Asp
            100                 105                 110
Gly Lys Ala Ser Phe Thr Cys Thr Cys Lys Pro Gly Trp Gln Gly Glu
        115                 120                 125
Lys Cys Glu Phe Asp Ile Asn Glu Cys Lys Asp Pro Ser Asn Ile Asn
130                 135                 140
Gly Gly Cys Ser Gln Ile Cys Asp Asn Thr Pro Gly Ser Tyr His Cys
145                 150                 155                 160
Ser Cys Lys Asn Gly Phe Val Met Leu Ser Asn Lys Lys Asp Cys Lys
                165                 170                 175
Asp Val Asp Glu Cys Ser Leu Lys Pro Ser Ile Cys Gly Thr Ala Val
            180                 185                 190
Cys Lys Asn Ile Pro Gly Asp Phe Glu Cys Glu Cys Pro Glu Gly Tyr
        195                 200                 205
Arg Tyr Asn Leu Lys Ser Lys Ser Cys Glu Asp Ile Asp Glu Cys Ser
210                 215                 220
Glu Asn Met Cys Ala Gln Leu Cys Val Asn Tyr Pro Gly Gly Tyr Thr
225                 230                 235                 240
Cys Tyr Cys Asp Gly Lys Lys Gly Phe Lys Leu Ala Gln Asp Gln Lys
                245                 250                 255
Ser Cys Glu Val Val Ser Val Cys Leu Pro Leu Asn Leu Asp Thr Lys
            260                 265                 270
Tyr Glu Leu Leu Tyr Leu Ala Glu Gln Phe Ala Gly Val Val Leu Tyr
        275                 280                 285
Leu Lys Phe Arg Leu Pro Glu Ile Ser Arg Phe Ser Ala Glu Phe Asp
290                 295                 300
Phe Arg Thr Tyr Asp Ser Glu Gly Val Ile Leu Tyr Ala Glu Ser Ile
305                 310                 315                 320
Asp His Ser Ala Trp Leu Leu Ile Ala Leu Arg Gly Gly Lys Ile Glu
                325                 330                 335
Val Gln Leu Lys Asn Glu His Thr Ser Lys Ile Thr Thr Gly Gly Asp
            340                 345                 350
Val Ile Asn Asn Gly Leu Trp Asn Met Val Ser Val Glu Glu Leu Glu
        355                 360                 365
His Ser Ile Ser Ile Lys Ile Ala Lys Glu Ala Val Met Asp Ile Asn
370                 375                 380
Lys Pro Gly Pro Leu Phe Lys Pro Glu Asn Gly Leu Leu Glu Thr Lys
385                 390                 395                 400
Val Tyr Phe Ala Gly Phe Pro Arg Lys Val Glu Ser Glu Leu Ile Lys
                405                 410                 415
Pro Ile Asn Pro Arg Leu Asp Gly Cys Ile Arg Ser Trp Asn Leu Met
            420                 425                 430
Lys Gln Gly Ala Ser Gly Ile Lys Glu Ile Ile Gln Glu Lys Gln Asn
        435                 440                 445
```

```
Lys His Cys Leu Val Thr Val Glu Lys Gly Ser Tyr Tyr Pro Gly Ser
    450                 455                 460

Gly Ile Ala Gln Phe His Ile Asp Tyr Asn Asn Val Ser Ser Ala Glu
465                 470                 475                 480

Gly Trp His Val Asn Val Thr Leu Asn Ile Arg Pro Ser Thr Gly Thr
                485                 490                 495

Gly Val Met Leu Ala Leu Val Ser Gly Asn Asn Thr Val Pro Phe Ala
            500                 505                 510

Val Ser Leu Val Asp Ser Thr Ser Glu Lys Ser Gln Asp Ile Leu Leu
        515                 520                 525

Ser Val Glu Asn Thr Val Ile Tyr Arg Ile Gln Ala Leu Ser Leu Cys
    530                 535                 540

Ser Asp Gln Gln Ser His Leu Glu Phe Arg Val Asn Arg Asn Asn Leu
545                 550                 555                 560

Glu Leu Ser Thr Pro Leu Lys Ile Glu Thr Ile Ser His Glu Asp Leu
                565                 570                 575

Gln Arg Gln Leu Ala Val Leu Asp Lys Ala Met Lys Ala Lys Val Ala
            580                 585                 590

Thr Tyr Leu Gly Gly Leu Pro Asp Val Pro Phe Ser Ala Thr Pro Val
        595                 600                 605

Asn Ala Phe Tyr Asn Gly Cys Met Glu Val Asn Ile Asn Gly Val Gln
    610                 615                 620

Leu Asp Leu Asp Glu Ala Ile Ser Lys His Asn Asp Ile Arg Ala His
625                 630                 635                 640

Ser Cys Pro Ser Val Trp Lys Lys Thr Lys Asn Ser
                645                 650

<210> SEQ ID NO 7
<211> LENGTH: 1908
<212> TYPE: DNA
<213> ORGANISM: Homo sapiens
<220> FEATURE:
<221> NAME/KEY: CDS
<222> LOCATION: (1)..(1908)

<400> SEQUENCE: 7 gca aat tct tta ctt gaa gaa acc aaa cag ggt aat ctt gaa aga gaa    48
Ala Asn Ser Leu Leu Glu Glu Thr Lys Gln Gly Asn Leu Glu Arg Glu
1               5                   10                  15 tgc atc gaa gaa ctg tgc aat aaa gaa gaa gcc agg gag gtc ttt gaa    96
Cys Ile Glu Glu Leu Cys Asn Lys Glu Glu Ala Arg Glu Val Phe Glu
            20                  25                  30 aat gac ccg gaa acg gat tat ttt tat cca aaa tac tta gtt tgt ctt   144
Asn Asp Pro Glu Thr Asp Tyr Phe Tyr Pro Lys Tyr Leu Val Cys Leu
        35                  40                  45 cgc tct ttt caa act ggg tta ttc act gct gca cgt cag tca act aat   192
Arg Ser Phe Gln Thr Gly Leu Phe Thr Ala Ala Arg Gln Ser Thr Asn
    50                  55                  60 gct tat cct gac cta aga agc tgt gtc aat gcc att cca gac cag tgt   240
Ala Tyr Pro Asp Leu Arg Ser Cys Val Asn Ala Ile Pro Asp Gln Cys
65                  70                  75                  80 agt cct ctg cca tgt aat gaa gat gga tat atg agc tgc aaa gat gga   288
Ser Pro Leu Pro Cys Asn Glu Asp Gly Tyr Met Ser Cys Lys Asp Gly
                85                  90                  95 aaa gct tct ttt act tgc act tgt aaa cca ggt tgg caa gga gaa aag   336
Lys Ala Ser Phe Thr Cys Thr Cys Lys Pro Gly Trp Gln Gly Glu Lys
            100                 105                 110 tgt gaa ttt gac ata aat gaa tgc aaa gat ccc tca aat ata aat gga   384
```

-continued

| | | | | | | | | | | | | | | |
|---|---|---|---|---|---|---|---|---|---|---|---|---|---|---|
| Cys | Glu | Phe | Asp | Ile | Asn | Glu | Cys | Lys | Asp | Pro | Ser | Asn | Ile | Asn | Gly |
| | 115 | | | | 120 | | | | 125 | | | | | | |

| ggt | tgc | agt | caa | att | tgt | gat | aat | aca | cct | gga | agt | tac | cac | tgt | tcc | 432 |
|---|---|---|---|---|---|---|---|---|---|---|---|---|---|---|---|---|
| Gly | Cys | Ser | Gln | Ile | Cys | Asp | Asn | Thr | Pro | Gly | Ser | Tyr | His | Cys | Ser | |
| 130 | | | | | 135 | | | | | 140 | | | | | | |

| tgt | aaa | aat | ggt | ttt | gtt | atg | ctt | tca | aat | aag | aaa | gat | tgt | aaa | gat | 480 |
|---|---|---|---|---|---|---|---|---|---|---|---|---|---|---|---|---|
| Cys | Lys | Asn | Gly | Phe | Val | Met | Leu | Ser | Asn | Lys | Lys | Asp | Cys | Lys | Asp | |
| 145 | | | | | 150 | | | | | 155 | | | | | 160 | |

| gtg | gat | gaa | tgc | tct | ttg | aag | cca | agc | att | tgt | ggc | aca | gct | gtg | tgc | 528 |
|---|---|---|---|---|---|---|---|---|---|---|---|---|---|---|---|---|
| Val | Asp | Glu | Cys | Ser | Leu | Lys | Pro | Ser | Ile | Cys | Gly | Thr | Ala | Val | Cys | |
| | | | 165 | | | | | 170 | | | | | 175 | | | |

| aag | aac | atc | cca | gga | gat | ttt | gaa | tgt | gaa | tgc | ccc | gaa | ggc | tac | aga | 576 |
|---|---|---|---|---|---|---|---|---|---|---|---|---|---|---|---|---|
| Lys | Asn | Ile | Pro | Gly | Asp | Phe | Glu | Cys | Glu | Cys | Pro | Glu | Gly | Tyr | Arg | |
| | | | 180 | | | | | 185 | | | | | 190 | | | |

| tat | aat | ctc | aaa | tca | aag | tct | tgt | gaa | gat | ata | gat | gaa | tgc | tct | gag | 624 |
|---|---|---|---|---|---|---|---|---|---|---|---|---|---|---|---|---|
| Tyr | Asn | Leu | Lys | Ser | Lys | Ser | Cys | Glu | Asp | Ile | Asp | Glu | Cys | Ser | Glu | |
| | | | 195 | | | | | 200 | | | | | 205 | | | |

| aac | atg | tgt | gct | cag | ctt | tgt | gtc | aat | tac | cct | gga | ggt | tac | act | tgc | 672 |
|---|---|---|---|---|---|---|---|---|---|---|---|---|---|---|---|---|
| Asn | Met | Cys | Ala | Gln | Leu | Cys | Val | Asn | Tyr | Pro | Gly | Gly | Tyr | Thr | Cys | |
| 210 | | | | | 215 | | | | | 220 | | | | | | |

| tat | tgt | gat | ggg | aag | aaa | gga | ttc | aaa | ctt | gcc | caa | gat | cag | aag | agt | 720 |
|---|---|---|---|---|---|---|---|---|---|---|---|---|---|---|---|---|
| Tyr | Cys | Asp | Gly | Lys | Lys | Gly | Phe | Lys | Leu | Ala | Gln | Asp | Gln | Lys | Ser | |
| 225 | | | | | 230 | | | | | 235 | | | | | 240 | |

| tgt | gag | gtt | gtt | tca | gtg | tgc | ctt | ccc | ttg | aac | ctt | gac | aca | aag | tat | 768 |
|---|---|---|---|---|---|---|---|---|---|---|---|---|---|---|---|---|
| Cys | Glu | Val | Val | Ser | Val | Cys | Leu | Pro | Leu | Asn | Leu | Asp | Thr | Lys | Tyr | |
| | | | 245 | | | | | 250 | | | | | 255 | | | |

| gaa | tta | ctt | tac | ttg | gcg | gag | cag | ttt | gca | ggg | gtt | gtt | tta | tat | tta | 816 |
|---|---|---|---|---|---|---|---|---|---|---|---|---|---|---|---|---|
| Glu | Leu | Leu | Tyr | Leu | Ala | Glu | Gln | Phe | Ala | Gly | Val | Val | Leu | Tyr | Leu | |
| | | | 260 | | | | | 265 | | | | | 270 | | | |

| aaa | ttt | cgt | ttg | cca | gaa | atc | agc | aga | ttt | tca | gca | gaa | ttt | gat | ttc | 864 |
|---|---|---|---|---|---|---|---|---|---|---|---|---|---|---|---|---|
| Lys | Phe | Arg | Leu | Pro | Glu | Ile | Ser | Arg | Phe | Ser | Ala | Glu | Phe | Asp | Phe | |
| | | | 275 | | | | | 280 | | | | | 285 | | | |

| cgg | aca | tat | gat | tca | gaa | ggc | gtg | ata | ctg | tac | gca | gaa | tct | atc | gat | 912 |
|---|---|---|---|---|---|---|---|---|---|---|---|---|---|---|---|---|
| Arg | Thr | Tyr | Asp | Ser | Glu | Gly | Val | Ile | Leu | Tyr | Ala | Glu | Ser | Ile | Asp | |
| | 290 | | | | | 295 | | | | | 300 | | | | | |

| cac | tca | gcg | tgg | ctc | ctg | att | gca | ctt | cgt | ggt | gga | aag | att | gaa | gtt | 960 |
|---|---|---|---|---|---|---|---|---|---|---|---|---|---|---|---|---|
| His | Ser | Ala | Trp | Leu | Leu | Ile | Ala | Leu | Arg | Gly | Gly | Lys | Ile | Glu | Val | |
| 305 | | | | | 310 | | | | | 315 | | | | | 320 | |

| cag | ctt | aag | aat | gaa | cat | aca | tcc | aaa | atc | aca | act | gga | ggt | gat | gtt | 1008 |
|---|---|---|---|---|---|---|---|---|---|---|---|---|---|---|---|---|
| Gln | Leu | Lys | Asn | Glu | His | Thr | Ser | Lys | Ile | Thr | Thr | Gly | Gly | Asp | Val | |
| | | | 325 | | | | | 330 | | | | | 335 | | | |

| att | aat | aat | ggt | cta | tgg | aat | atg | gtg | tct | gtg | gaa | gaa | tta | gaa | cat | 1056 |
|---|---|---|---|---|---|---|---|---|---|---|---|---|---|---|---|---|
| Ile | Asn | Asn | Gly | Leu | Trp | Asn | Met | Val | Ser | Val | Glu | Glu | Leu | Glu | His | |
| | | | 340 | | | | | 345 | | | | | 350 | | | |

| agt | att | agc | att | aaa | ata | gct | aaa | gaa | gct | gtg | atg | gat | ata | aat | aaa | 1104 |
|---|---|---|---|---|---|---|---|---|---|---|---|---|---|---|---|---|
| Ser | Ile | Ser | Ile | Lys | Ile | Ala | Lys | Glu | Ala | Val | Met | Asp | Ile | Asn | Lys | |
| | | | 355 | | | | | 360 | | | | | 365 | | | |

| cct | gga | ccc | ctt | ttt | aag | ccg | gaa | aat | gga | ttg | ctg | gaa | acc | aaa | gta | 1152 |
|---|---|---|---|---|---|---|---|---|---|---|---|---|---|---|---|---|
| Pro | Gly | Pro | Leu | Phe | Lys | Pro | Glu | Asn | Gly | Leu | Leu | Glu | Thr | Lys | Val | |
| 370 | | | | | 375 | | | | | 380 | | | | | | |

| tac | ttt | gca | gga | ttc | cct | cgg | aaa | gtg | gaa | agt | gaa | ctc | att | aaa | ccg | 1200 |
|---|---|---|---|---|---|---|---|---|---|---|---|---|---|---|---|---|
| Tyr | Phe | Ala | Gly | Phe | Pro | Arg | Lys | Val | Glu | Ser | Glu | Leu | Ile | Lys | Pro | |
| 385 | | | | | 390 | | | | | 395 | | | | | 400 | |

| att | aac | cct | cgt | cta | gat | gga | tgt | ata | cga | agc | tgg | aat | ttg | atg | aag | 1248 |
|---|---|---|---|---|---|---|---|---|---|---|---|---|---|---|---|---|
| Ile | Asn | Pro | Arg | Leu | Asp | Gly | Cys | Ile | Arg | Ser | Trp | Asn | Leu | Met | Lys | |
| | | | 405 | | | | | 410 | | | | | 415 | | | |

| caa | gga | gct | tct | gga | ata | aag | gaa | att | att | caa | gaa | aaa | caa | aat | aag | 1296 |
|---|---|---|---|---|---|---|---|---|---|---|---|---|---|---|---|---|
| Gln | Gly | Ala | Ser | Gly | Ile | Lys | Glu | Ile | Ile | Gln | Glu | Lys | Gln | Asn | Lys | |
| | 420 | | | | | 425 | | | | | 430 | | | | | |

| cat | tgc | ctg | gtt | act | gtg | gag | aag | ggc | tcc | tac | tat | cct | ggt | tct | gga | 1344 |
|---|---|---|---|---|---|---|---|---|---|---|---|---|---|---|---|---|

-continued

```
                His Cys Leu Val Thr Val Glu Lys Gly Ser Tyr Tyr Pro Gly Ser Gly
                        435                 440                 445 att gct caa ttt cac ata gat tat aat aat gta tcc agt gct gag ggt          1392
Ile Ala Gln Phe His Ile Asp Tyr Asn Asn Val Ser Ser Ala Glu Gly
450                 455                 460 tgg cat gta aat gtg acc ttg aat att cgt cca tcc acg ggc act ggt          1440
Trp His Val Asn Val Thr Leu Asn Ile Arg Pro Ser Thr Gly Thr Gly
465                 470                 475                 480 gtt atg ctt gcc ttg gtt tct ggt aac aac aca gtg ccc ttt gct gtg          1488
Val Met Leu Ala Leu Val Ser Gly Asn Asn Thr Val Pro Phe Ala Val
                485                 490                 495 tcc ttg gtg gac tcc acc tct gaa aaa tca cag gat att ctg tta tct          1536
Ser Leu Val Asp Ser Thr Ser Glu Lys Ser Gln Asp Ile Leu Leu Ser
            500                 505                 510 gtt gaa aat act gta ata tat cgg ata cag gcc cta agt cta tgt tcc          1584
Val Glu Asn Thr Val Ile Tyr Arg Ile Gln Ala Leu Ser Leu Cys Ser
        515                 520                 525 gat caa caa tct cat ctg gaa ttt aga gtc aac aga aac aat ctg gag          1632
Asp Gln Gln Ser His Leu Glu Phe Arg Val Asn Arg Asn Asn Leu Glu
    530                 535                 540 ttg tcg aca cca ctt aaa ata gaa acc atc tcc cat gaa gac ctt caa          1680
Leu Ser Thr Pro Leu Lys Ile Glu Thr Ile Ser His Glu Asp Leu Gln
545                 550                 555                 560 aga caa ctt gcc gtc ttg gac aaa gca atg aaa gca aaa gtg gcc aca          1728
Arg Gln Leu Ala Val Leu Asp Lys Ala Met Lys Ala Lys Val Ala Thr
                565                 570                 575 tac ctg ggt ggc ctt cca gat gtt cca ttc agt gcc aca cca gtg aat          1776
Tyr Leu Gly Gly Leu Pro Asp Val Pro Phe Ser Ala Thr Pro Val Asn
            580                 585                 590 gcc ttt tat aat ggc tgc atg gaa gtg aat att aat ggt gta cag ttg          1824
Ala Phe Tyr Asn Gly Cys Met Glu Val Asn Ile Asn Gly Val Gln Leu
        595                 600                 605 gat ctg gat gaa gcc att tct aaa cat aat gat att aga gct cac tca          1872
Asp Leu Asp Glu Ala Ile Ser Lys His Asn Asp Ile Arg Ala His Ser
    610                 615                 620 tgt cca tca gtt tgg aaa aag aca aag aat tct taa                          1908
Cys Pro Ser Val Trp Lys Lys Thr Lys Asn Ser
625                 630                 635

<210> SEQ ID NO 8
<211> LENGTH: 635
<212> TYPE: PRT
<213> ORGANISM: Homo sapiens

<400> SEQUENCE: 8

Ala Asn Ser Leu Leu Glu Glu Thr Lys Gln Gly Asn Leu Glu Arg Glu
1               5                   10                  15

Cys Ile Glu Glu Leu Cys Asn Lys Glu Glu Ala Arg Glu Val Phe Glu
            20                  25                  30

Asn Asp Pro Glu Thr Asp Tyr Phe Tyr Pro Lys Tyr Leu Val Cys Leu
        35                  40                  45

Arg Ser Phe Gln Thr Gly Leu Phe Thr Ala Ala Arg Gln Ser Thr Asn
    50                  55                  60

Ala Tyr Pro Asp Leu Arg Ser Cys Val Asn Ala Ile Pro Asp Gln Cys
65                  70                  75                  80

Ser Pro Leu Pro Cys Asn Glu Asp Gly Tyr Met Ser Cys Lys Asp Gly
                85                  90                  95

Lys Ala Ser Phe Thr Cys Thr Cys Lys Pro Gly Trp Gln Gly Glu Lys
            100                 105                 110
```

```
Cys Glu Phe Asp Ile Asn Glu Cys Lys Asp Pro Ser Asn Ile Asn Gly
        115                 120                 125

Gly Cys Ser Gln Ile Cys Asp Asn Thr Pro Gly Ser Tyr His Cys Ser
    130                 135                 140

Cys Lys Asn Gly Phe Val Met Leu Ser Asn Lys Lys Asp Cys Lys Asp
145                 150                 155                 160

Val Asp Glu Cys Ser Leu Lys Pro Ser Ile Cys Gly Thr Ala Val Cys
                165                 170                 175

Lys Asn Ile Pro Gly Asp Phe Glu Cys Glu Cys Pro Glu Gly Tyr Arg
            180                 185                 190

Tyr Asn Leu Lys Ser Lys Ser Cys Glu Asp Ile Asp Glu Cys Ser Glu
        195                 200                 205

Asn Met Cys Ala Gln Leu Cys Val Asn Tyr Pro Gly Gly Tyr Thr Cys
    210                 215                 220

Tyr Cys Asp Gly Lys Lys Gly Phe Lys Leu Ala Gln Asp Gln Lys Ser
225                 230                 235                 240

Cys Glu Val Val Ser Val Cys Leu Pro Leu Asn Leu Asp Thr Lys Tyr
                245                 250                 255

Glu Leu Leu Tyr Leu Ala Glu Gln Phe Ala Gly Val Val Leu Tyr Leu
            260                 265                 270

Lys Phe Arg Leu Pro Glu Ile Ser Arg Phe Ser Ala Glu Phe Asp Phe
        275                 280                 285

Arg Thr Tyr Asp Ser Glu Gly Val Ile Leu Tyr Ala Glu Ser Ile Asp
    290                 295                 300

His Ser Ala Trp Leu Leu Ile Ala Leu Arg Gly Gly Lys Ile Glu Val
305                 310                 315                 320

Gln Leu Lys Asn Glu His Thr Ser Lys Ile Thr Thr Gly Gly Asp Val
                325                 330                 335

Ile Asn Asn Gly Leu Trp Asn Met Val Ser Val Glu Glu Leu Glu His
            340                 345                 350

Ser Ile Ser Ile Lys Ile Ala Lys Glu Ala Val Met Asp Ile Asn Lys
        355                 360                 365

Pro Gly Pro Leu Phe Lys Pro Glu Asn Gly Leu Leu Glu Thr Lys Val
    370                 375                 380

Tyr Phe Ala Gly Phe Pro Arg Lys Val Glu Ser Glu Leu Ile Lys Pro
385                 390                 395                 400

Ile Asn Pro Arg Leu Asp Gly Cys Ile Arg Ser Trp Asn Leu Met Lys
                405                 410                 415

Gln Gly Ala Ser Gly Ile Lys Glu Ile Ile Gln Glu Lys Gln Asn Lys
            420                 425                 430

His Cys Leu Val Thr Val Glu Lys Gly Ser Tyr Tyr Pro Gly Ser Gly
        435                 440                 445

Ile Ala Gln Phe His Ile Asp Tyr Asn Asn Val Ser Ser Ala Glu Gly
    450                 455                 460

Trp His Val Asn Val Thr Leu Asn Ile Arg Pro Ser Thr Gly Thr Gly
465                 470                 475                 480

Val Met Leu Ala Leu Val Ser Gly Asn Asn Thr Val Pro Phe Ala Val
                485                 490                 495

Ser Leu Val Asp Ser Thr Ser Glu Lys Ser Gln Asp Ile Leu Leu Ser
            500                 505                 510

Val Glu Asn Thr Val Ile Tyr Arg Ile Gln Ala Leu Ser Leu Cys Ser
        515                 520                 525

Asp Gln Gln Ser His Leu Glu Phe Arg Val Asn Arg Asn Asn Leu Glu
    530                 535                 540
```

-continued

```
Leu Ser Thr Pro Leu Lys Ile Glu Thr Ile Ser His Glu Asp Leu Gln
545                 550                 555                 560

Arg Gln Leu Ala Val Leu Asp Lys Ala Met Lys Ala Lys Val Ala Thr
                565                 570                 575

Tyr Leu Gly Gly Leu Pro Asp Val Pro Phe Ser Ala Thr Pro Val Asn
            580                 585                 590

Ala Phe Tyr Asn Gly Cys Met Glu Val Asn Ile Asn Gly Val Gln Leu
        595                 600                 605

Asp Leu Asp Glu Ala Ile Ser Lys His Asn Asp Ile Arg Ala His Ser
            610                 615                 620

Cys Pro Ser Val Trp Lys Lys Thr Lys Asn Ser
625                 630                 635
```

RECOMBINANT PROTEIN S COMPOSITION

BACKGROUND OF THE INVENTION

1. Field of the Invention

The present invention relates to a Protein S composition comprising recombinant Protein S molecules having complex type N-glycoside-linked sugar chains, having a higher binding activity to a receptor for advanced glycation end products (hereinafter referred to as "RAGE") than native Protein S present in healthy human blood, and having a high ratio of sugar chains in which fucose is not bound to the complex type N-glycoside-linked sugar chains bound to Protein S than native Protein S present in healthy human blood; and a therapeutic use using the composition.

2. Brief Description of the Background Art

Protein S is a glycoprotein isolated from human plasma, having a molecular weight of about $8 \times 10^4$ daltons and being responsible for an anticoagulant activity in plasma (Non-Patent Document 1, and Patent Document 1). It is known that mRNA expression of Protein S is confirmed in the liver, vascular endothelium, megakaryocytes, testis, and brain and the main production organ of the protein is the liver (Non-Patent Document 2).

The protein moiety of mature Protein S secreted into plasma is a multi-domain type single-chain polypeptide consisting of 635 amino acid residues (SEQ ID NO:8) and containing 17 disulfide bonds in the molecule. Protein S is classified as a vitamin K-dependent protein family, similar to blood coagulation factor VII, factor IX, prothrombin, Protein C, and the like. Native Protein S is known to have four types of domain structures in the molecule thereof, specifically, a γ-carboxylglutamic acid (hereinafter referred to as "Gla") domain, a thrombin sensitive region, four consecutive epidermal growth factor (EGF)-like domains and a sex hormone-binding globulin (SHBG)-like domain from the amino terminal.

It is known that an asparagine-linked sugar chain contained in the native Protein S molecule is bound to three asparagine residues of Asn458, Asn468 and Asn489 in the SHBG-like domain. Further, it is known that Heerlen mutation, a type of congenital Protein S deficiency, has a replacement of Ser460 with Pro, which results in no addition of a sugar chain to the position of Asn458, thereby decreasing a half-life of Protein S in blood (Non-Patent Documents 3 and 4).

Regarding main physiological functions of Protein S, it is known that Protein S has an inhibitory activity of blood coagulation by promoting the degradation of blood coagulation factors since the Protein S functions as a cofactor which enhances an activity of the APC enzyme by about 20-folds by binding to activated protein C (APC), a serine protease present in human plasma. This anticoagulation activity of Protein S is known as APC cofactor activity.

Further, it is known that Protein S has diverse biological activities, such as a phospholipid binding activity (Non-Patent Document 5), a prothrombinase formation inhibitory activity (Non-Patent Documents 6 and 7), a tenase formation inhibitory activity, a complement C4BP binding activity (Non-Patent Documents 8 and 9), a tissue factor pathway inhibitor (TFPI) cofactor activity (Non-Patent Document 10), and a macrophage surface receptor Axl/Mer/Tyro binding activity (Non-Patent Document 11). It is known that the APC cofactor activity and the phospholipid binding activity among the above-mentioned activities are directly affected by γ-carboxylation of glutamic acid (Glu-to-Gla conversion), a type of post-translational modifications occurring in Protein S molecules in a cell, and by conformational changes of the Gla domain due to coordination of calcium ions in the Gla domain. However, little is known about the relationship between sugar chain structures of Protein S and a variety of biological responses in which Protein S is involved, except the above-mentioned example of the Heerlen mutant.

According to the results of analysis of pathological mechanisms at a molecular level, a role of inflammatory mediator molecules which increases in the bodies of patients has been recently become clear in a variety of human diseases where an excessive increase of blood coagulation and inflammation leads to multi-organ failure, such as sepsis or disseminated intravascular coagulation (DIC).

The receptor for advanced glycation end products (hereinafter referred to as "RAGE") is a membrane-bound protein known for a long period of time, and is known to be expressed mainly on surfaces of the vascular endothelium, and RAGE functions as a receptor of glycated proteins (AGEs) whose level is increased in blood of diabetic patients. Interestingly, the RAGE protein has been recently detected as a soluble protein (hereinafter referred to as "soluble RAGE") in peripheral blood of sepsis or DIC patients, and it is clear that a concentration of RAGE in blood is elevated concomitant with poor prognosis (Non-Patent Document 12). It is known that such a soluble RAGE is not only produced by cleavage of RAGE expressed on the membrane (hereinafter referred to as "membrane-type RAGE"), but also is extracellularly secreted as soluble RAGE (Non-Patent Document 13). It has been recently demonstrated that soluble RAGE activates lymphocytes as a result of specific binding to a certain type of integrin molecule (Mac-1) being expressed on the surface of lymphocytes, which consequently promotes the secretion of inflammatory cytokines such as tumor necrosis factor α (TNFα) or interleukin-6 (IL-6) (Non-Patent Document 14). In addition, in a lipopolysaccharide (LPS)-treated mouse sepsis model, administration of anti-RAGE neutralizing antibody has shown to result in significant improvements in a survival rate of mice (Non-Patent Document 15).

From these findings, soluble RAGE is recognized as a mediator molecule of inflammation, so it is considered as a target molecule in the development of inflammatory disease therapeutics. On the other hand, it is known that a membrane-type RAGE not only functions as a receptor of glycated proteins (AGEs), but also serves as a receptor of soluble inflammatory mediator molecules such as high mobility group box chromosomal protein (HMGB) family or S100 (soluble in 100% saturated ammonium sulfate) peptide family (Non-Patent Document 16). It is known that a variety of events relating to the enhanced inflammation, such as cellular chemotaxis, the enhanced cellular secretion of inflammatory cytokines, the elevated expression levels of adhesion molecules such as ICAM or VCAM, are introduced by the binding of HMGB or S100 to cells expressing membrane-type RAGE (Non-Patent Documents 17 and 18).

Meanwhile, an anti-inflammatory response of Protein S has not yet been known up to date, and further, there is no finding relating to the interaction between Protein S and RAGE.

CITATION LIST

Non-Patent Document

[Non-Patent Document 1] *Biochemistry* 16, 698 (1977)
[Non-Patent Document 2] *Journal of Thrombosis and Haemostasis* 12, 235 (2001)
[Non-Patent Document 3] *Blood* 76, 538 (1990)
[Non-Patent Document 4] *Thromb Res* 100, 81 (2000)

[Non-Patent Document 5] *JBC* 261, 5116 (1986)
[Non-Patent Document 6] *JBC* 268, 2872 (1993)
[Non-Patent Document 7] *PNAS* 91, 2728 (1994)
[Non-Patent Document 8] *Blood* 103, 1192 (2004)
[Non-Patent Document 9] *J Immunol* 169, 2580 (2002)
[Non-Patent Document 10] *PNAS* 103, 3106 (2006)
[Non-Patent Document 11] *Biol Chem* 381, 199 (2000)
[Non-Patent Document 12] *J Surgical Res* 147, 79 (2008)
[Non-Patent Document 13] *Current Molecular Medicine* 7, 777 (2007)
[Non-Patent Document 14] *Arthritis Rheumatism* 54, 3898 (2006)
[Non-Patent Document 15] *Critical Care* 11, R122 (2007)
[Non-Patent Document 16] *Current Molecular Medicine* 7, 743 (2007)
[Non-Patent Document 17] *Cell* 97, 889 (1999)
[Non-Patent Document 18] *J Immunol* 170, 3233 (2003)

Patent Document

[Patent Document 1] Japanese Patent No. 2557385

SUMMARY OF THE INVENTION

An object of the present invention is to provide a Protein S preparation having remarkably higher anti-inflammatory effect than conventional existing Protein S preparations, from the point of view of developing a therapeutic agent having high effects on a variety of human diseases arising from the excessive inflammatory reaction or formation of thrombi, associated with a decrease of Protein S in vivo. The present invention provides a Protein S composition comprising recombinant Protein S molecules having complex type N-glycoside-linked sugar chains, wherein the Protein S has a higher binding activity to a receptor for advanced glycation end products (hereinafter referred to as "RAGE") than native Protein S present in healthy human blood, and also has a higher ratio of sugar chains in which fucose is not bound to complex type N-glycoside-linked sugar chains bound to Protein S than native Protein S present in healthy human blood; and a therapeutic use using the same composition.

DETAILED DESCRIPTION OF THE INVENTION

Figure 1:
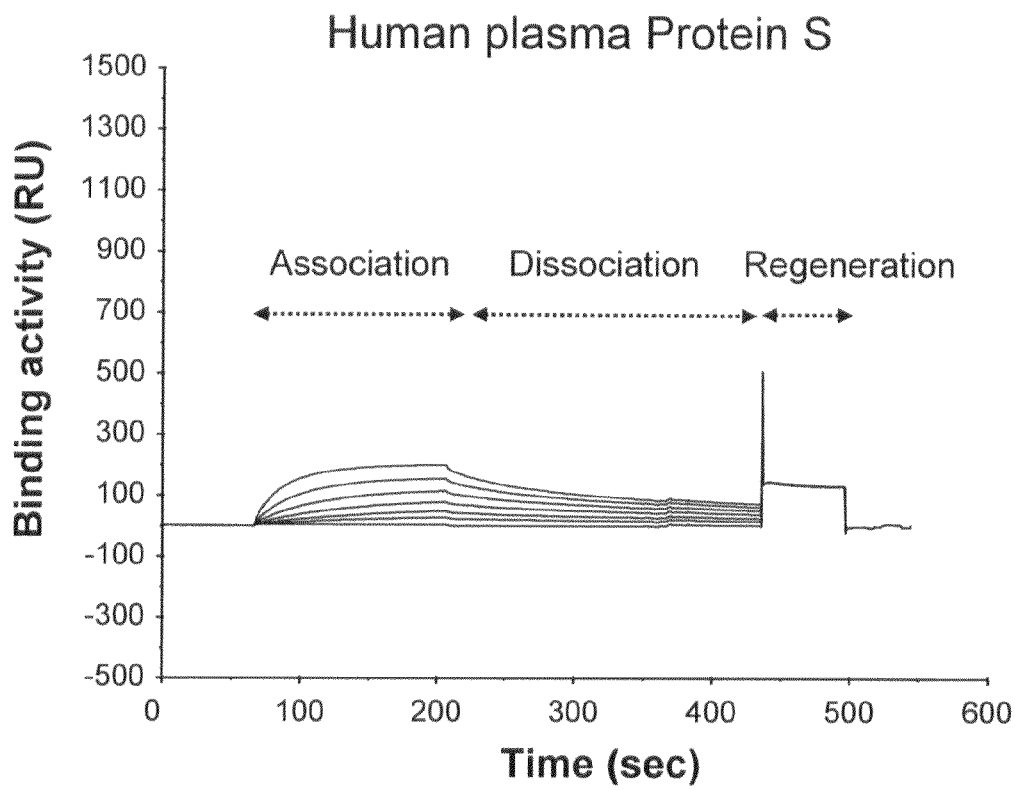
FIG. 1 shows the analysis results of a binding activity of *Lens culinaris* agglutinin (LCA) lectin to human plasma-derived Protein S or human plasma antithrombin III, as measured by surface plasmon resonance. The abscissa represents time (seconds), and the ordinate represents a binding activity of LCA to a glycoprotein on a sensor chip of Biacore T100. From the top, each sensorgram represents a value obtained when LCA was allowed to run at concentrations of 50000, 25000, 12500, 6250, 3125 and 0 ng/mL. The top represents the binding between human plasma Protein S and LCA, and the bottom represents the binding between human plasma antithrombin III and LCA.
Figure 1:
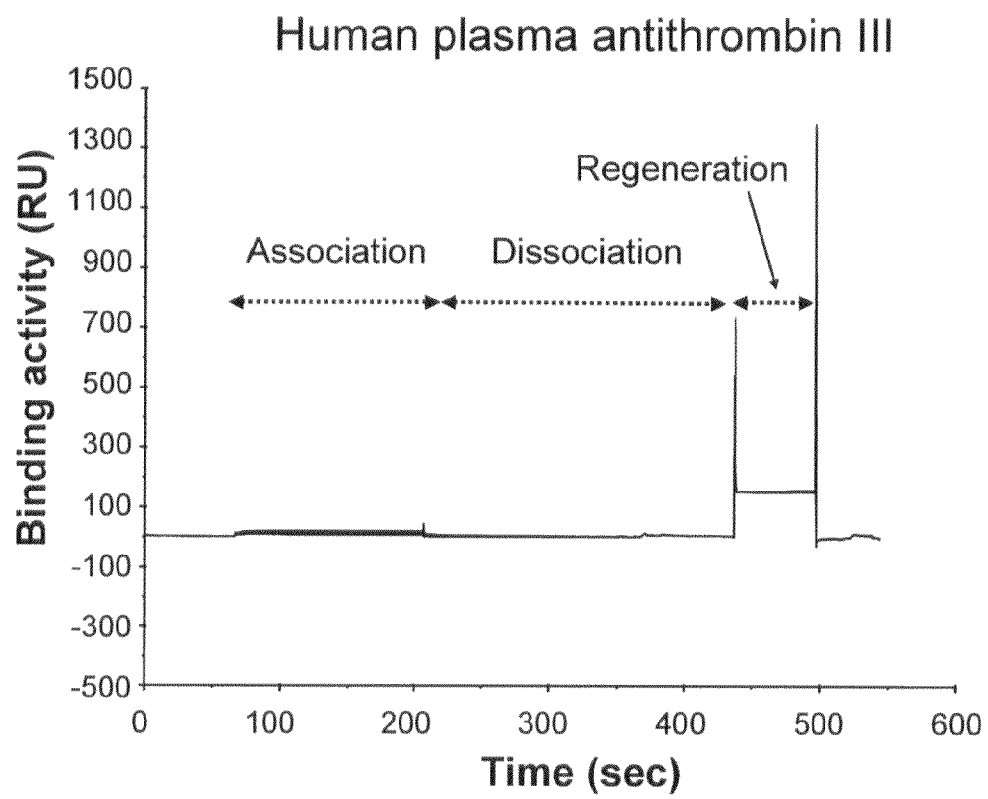

Specifically, the present invention relates to the following (1) to (25):

(1) A Protein S composition comprising recombinant Protein S molecules having complex type N-glycoside-linked sugar chains, wherein the Protein S has a higher binding activity to a receptor for advanced glycation end products (hereinafter referred to as "RAGE") than native Protein S present in the healthy human blood, and has a higher ratio of sugar chains in which fucose is not bound to the complex type N-glycoside-linked sugar chains bound to Protein S than native Protein S present in healthy human blood;

(2) The Protein S composition described in the above (1), wherein the complex type N-glycoside-linked sugar chains are sugar chains in which fucose is not bound to N-acetylglucosamine in the reducing end in the sugar chains;

(3) The Protein S composition described in the above (1) or (2), wherein the complex type N-glycoside-linked sugar chains are sugar chains in which sialic acid is bound to galactose in the non-reducing end in the sugar chains;

(4) The Protein S composition described in any one of the above (1) to (3), wherein the complex type N-glycoside-linked sugar chains are sugar chains which bind to at least one asparagine residue at positions 458, 468 and 489 from the N-terminal of Protein S;

(5) The Protein S composition described in any one of the above (1) to (4), wherein a sequence of amino acids at positions 1 to 45 from the N-terminal of Protein S is an amino acid sequence in which a side chain of at least one glutamic acid residue in the amino acid sequence is subjected to γ-carboxylation;

(6) The Protein S composition described in any one of the above (1) to (5), wherein the Protein S is a protein selected from the group consisting of the following (a), (b) and (c):
   (a) a protein comprising the amino acid sequence represented by SEQ ID NO:8 (human wild type Protein S);
   (b) a protein consisting of an amino acid sequence wherein one or more amino acid residue(s) is/are deleted, substituted, inserted and/or added in the amino acid sequence represented by SEQ ID NO:8, and having a binding activity to RAGE; and
   (c) a protein consisting of an amino acid sequence having 80% or more homology to the amino acid sequence of SEQ ID NO:8, and having a binding activity to RAGE;

(7) The Protein S composition described in any one of the above (1) to (6), wherein the Protein S is a protein encoded by a DNA selected from the following (a) or (b):
   (a) a DNA comprising the nucleotide sequence of SEQ ID NO:7 (human wild type Protein S);
   (b) a DNA which hybridizes with a DNA consisting of the nucleotide sequence of SEQ ID NO:7 under stringent conditions and encodes a protein having a binding activity to RAGE;

(8) A cell which produces the Protein S described in any one of the above (1) to (7);

(9) The cell described in the above (8), wherein the cell is a cell in which genome is modified so as to delete the activity of an enzyme relating to the synthesis of an intracellular sugar nucleotide, GDP-fucose;

(10) The cell described in the above (9), wherein the enzyme relating to the synthesis of the intracellular sugar nucleotide, GDP-fucose is an enzyme selected from the group consisting of GDP-mannose 4,6-dehydratase and GDP-4-keto-6-deoxy-D-mannose-3,5-epimerase;

(11) The cell described in the above (8), wherein the cell is a cell in which genome is modified so as to delete the activity of an enzyme relating to the modification of a sugar chain in which fucose is bound to N-acetylglucosamine in the reducing end through α-bond in a complex type N-glycoside-linked sugar chain;

(12) The cell described in the above (11), wherein the enzyme relating to the modification of a sugar chain in which fucose is bound to N-acetylglucosamine in the reducing end through α-bond in a complex type N-glycoside-linked sugar chain is α1,6-fucosyltransferase;

(13) The cell described in the above (11), wherein the enzyme relating to the modification of a sugar chain in which fucose is bound to N-acetylglucosamine in the reducing end through α-bond in a complex type N-glycoside-linked sugar chain is α1,3-fucosyltransferase;

(14) The cell described in the above (8), wherein the cell is a cell which is resistant to a lectin recognizing a sugar chain structure in which 1-position of fucose is bound to 6-position of N-acetylglucosamine in the reducing end through α-bond in a complex type N-glycoside-linked sugar chain;

(15) A transgenic animal which produces the Protein S described in the above (1) to (7);

(16) The transgenic animal described in the above (15), which is an animal in which genome is modified so as to delete the activity of an enzyme relating to the synthesis of an intracellular sugar nucleotide, GDP-fucose;

(17) The transgenic animal described in the above (15), wherein the enzyme relating to the synthesis of the intracellular sugar nucleotide, GDP-fucose is an enzyme selected from the group consisting of GDP-mannose 4,6-dehydratase and GDP-4-keto-6-deoxy-D-mannose-3,5-epimerase;

(18) The transgenic animal described in the above (15), which is an animal in which genome is modified so as to delete the activity of an enzyme relating to the modification of a sugar chain in which fucose is bound to N-acetylglucosamine in the reducing end through α-bond in a complex type N-glycoside-linked sugar chain;

(19) The transgenic animal described in the above (15), wherein the enzyme relating to the modification of a sugar chain in which fucose is bound to N-acetylglucosamine in the reducing end through α-bond in a complex type N-glycoside-linked sugar chain is α1,6-fucosyltransferase;

(20) A process for producing the Protein S composition described in any one of the above (1) to (7), comprising culturing the cell described in any one of the above (8) to (14) in a medium to produce and accumulate the Protein S composition described in any one of the above (1) to (7) in the culture, and collecting the Protein S composition from the culture;

(21) A process for producing the Protein S composition described in the above (1) to (7), comprising breeding the transgenic animal described in any one of the above (15) to (19) to produce and accumulate the Protein S composition described in any one of the above (1) to (7) in milk of the transgenic animal, and collecting the Protein S composition from the milk after expression;

(22) A pharmaceutical composition comprising the Protein S composition described in any one of the above (1) to (7) as an active ingredient;

(23) An anti-inflammatory agent comprising the Protein S composition described in any one of the above (1) to (7) as an active ingredient;

(24) An agent for treating sepsis comprising the Protein S composition described in any one of the above (1) to (7) as an active ingredient; and

(25) An agent for preventing or treating thrombosis comprising the Protein S composition described in any one of the above (1) to (7) as an active ingredient.

In the present invention, the term "Protein S composition comprising recombinant Protein S molecules having complex type N-glycoside-linked sugar chains, wherein the Protein S has a higher binding activity to a receptor for advanced glycation end products (hereinafter referred to as "RAGE") than native Protein S present in healthy human blood, and has a higher ratio of sugar chains in which fucose is not bound to the complex N-glycoside-linked sugar chains bound to Protein S than native Protein S present in healthy human blood" (hereinafter referred to often as "fucose-free Protein S composition") includes any composition, so long as it is a Protein S composition having a higher binding activity to the pattern recognition receptor (PRR) family such as RAGE than native Protein S present in healthy human blood, and also having a higher ratio of sugar chains in which fucose is not bound to the complex type N-glycoside-linked sugar chains bound to Protein S than native Protein S present in healthy human blood.

In the present invention, the term "native Protein S" includes any protein, so long as it is Protein S which is a single-chain glycoprotein present in healthy human blood, is responsible for the activated protein C (APC) cofactor activity in blood, belongs to the vitamin K-dependent protein family, and has a lower ratio of sugar chains to which fucose contained in a composition is not bound than the Protein S composition of the present invention.

In the present invention, the native Protein S is intracellularly produced as a precursor Protein S (SEQ ID NO:2) to which a secretory signal peptide is bound, next a secretory signal peptide is cleaved from the precursor in the endoplasmic reticulum and further a propeptide at the N-terminal of precursor Protein S(SEQ ID NO:6) is cleaved in the Golgi apparatus to be synthesized and secreted as mature Protein S(SEQ ID NO:8). The native Protein S has four types of domain structures in its molecule, i.e., a γ-carboxyl glutamic acid (Gla) domain, a thrombin sensitive region, four consecutive epidermal growth factor (EGF)-like domains, and a sex hormone-binding globulin (SHBG)-like domain from the N-terminal. Glutamic acid residues are modified to γ-carboxyl glutamic acid in the Gla domain, asparagine residues or aspartic residues are subjected to β-hydroxylation modification in the EGF-like domain, asparagine residues are post-translationally modified to a complex type asparagine-linked sugar chain in the SHBG-like domain of Protein S, respectively.

Examples of the Protein S composition of the present invention include a composition comprising recombinant Protein S molecules having complex type N-glycoside-linked sugar chains, which has a higher ratio of a sugar chain in which fucose is not bound to the complex type N-glycoside-linked sugar chains bound to Protein S than native Protein S present in healthy human blood.

In the present invention, the term "Protein S" includes any protein, so long as it is a glycoprotein which has a higher binding activity to RAGE than native Protein S, and also has a Gla domain subjected to γ-carboxylglutamic acid modification and a SHBG-like domain to which a complex type N-glycoside-linked sugar chain is added, and in which fucose is not bound to N-acetylglucosamine in the reducing end in the sugar chain.

The term "Gla domain subjected to γ-carboxylglutamic acid modification" refers to a domain in which a side chain of at least one glutamic acid residue is subjected to a γ-carboxylation modification in the amino acid sequence corresponding to positions 1 to 45 from the N-terminal of an amino acid sequence of Protein S.

The term "SHBG-like domain to which a complex type N-glycoside-linked sugar chain is added" refers to a domain in which a complex type N-linked sugar chain is added to a side chain of at least one asparagine residue at positions 458, 468 and 489, starting from the N-terminal of an amino acid sequence of Protein S.

Specific examples of the Protein S may include proteins encoded by the following DNAs (a) and (b), or the following proteins (c), (d), and (e).

(a) a DNA comprising the nucleotide sequence of SEQ ID NO:7;

(b) a DNA encoding a protein which hybridizes with a DNA consisting of the nucleotide sequence of SEQ ID NO:7 under stringent conditions, and has a binding activity to RAGE;

(c) a protein comprising the amino acid sequence of SEQ ID NO:8;

(d) a protein consisting of an amino acid sequence wherein one or more amino acid residue(s) is/are deleted, substituted, inserted and/or added in the amino acid sequence of SEQ ID NO:8, and having a binding activity to RAGE; and (e) a protein consisting of an amino acid sequence having 80% or more homology to the amino acid sequence of SEQ ID NO:8, and having a binding activity to RAGE.

In the present invention, the Protein S composition may be any one, so long as it is a glycoprotein composition comprising Protein S described in the above paragraphs as a main ingredient.

In the present invention, the DNA which hybridizes under stringent conditions refers to a DNA which is obtained by colony hybridization, plaque hybridization, Southern hybridization or the like using, for example, a DNA consisting of the nucleotide sequence of SEQ ID NO:7 or a fragment thereof as a probe. A specific example of such DNA is a DNA which can be identified by performing hybridization at 65° C. in the presence of 0.7 to 1.0 M sodium chloride using a filter with colony- or plaque-derived DNA immobilized thereon, and then washing the filter at 65° C. with a 0.1 to 2-fold concentration SSC solution (1-fold concentration SSC solution: 150 mM sodium chloride and 15 mM sodium citrate). Hybridization can be carried out according to the methods described in *Molecular Cloning, A Laboratory Manual*, Second Edition, Cold Spring Harbor Laboratory Press (1989) (hereinafter referred to as "*Molecular Cloning*, Second Edition"), *Current Protocols in Molecular Biology*, John Wiley & Sons (1987-1997) (hereinafter referred to as "*Current Protocols in Molecular Biology*"), *DNA Cloning 1: Core Techniques, A Practical Approach*, Second Edition, Oxford University (1995), etc. Specifically, the DNA capable of hybridization under stringent conditions includes DNA having at least 60% or more homology, preferably 70% or more homology, more preferably 80% or more homology, further preferably 90% or more homology, particularly preferably 95% or more homology, most preferably 98% or more homology to the nucleotide sequence of SEQ ID NO:7.

In the present invention, the protein consisting of an amino acid sequence wherein one or more amino acid residue(s) is/are deleted, substituted, inserted and/or added in the amino acid sequence of SEQ ID NO:8 and having the binding activity to RAGE can be obtained, for example, by introducing a site-directed mutation into DNA having the nucleotide sequence encoding the amino acid sequence of SEQ ID NO:8 by site-directed mutagenesis described in *Molecular Cloning*, Second Edition, *Current Protocols in Molecular Biology*, *Nucleic Acids Research*, 10, 6487 (1982), *Proc. Natl. Acad. Sci., USA*, 79, 6409 (1982), *Gene*, 34, 315 (1985), *Nucleic Acids Research*, 13, 4431 (1985), *Proc. Natl. Acad. Sci. USA*, 82, 488 (1985), etc. The number of amino acid residues which are deleted, substituted, inserted and/or added is one or more, and is not specifically limited, but it is within the range where deletion, substitution or addition is possible by known methods such as the above site-directed mutagenesis. The suitable number is 1 to dozens, preferably 1 to 20, more preferably 1 to 10, further preferably 1 to 5.

The protein consisting of an amino acid sequence which has 80% or more homology to the amino acid sequence of SEQ ID NO:8 and having the binding activity to RAGE includes a protein having at least 80% or more homology, preferably 85% or more homology, more preferably 90% or more homology, further preferably 95% or more homology, particularly preferably 97% or more homology, most preferably 99% or more homology to the amino acid sequence of SEQ ID NO:8, respectively, when calculated by use of analysis software such as BLAST [*J. Mol. Biol.*, 215, 403 (1990)] or FASTA [*Methods in Enzymology*, 183, 63 (1990)].

Preferably, the Protein S composition of the present invention may be a Protein S composition comprising recombinant Protein S molecules having complex type N-glycoside-linked sugar chains, which has a higher binding activity to RAGE than native Protein S present in healthy human blood, and also a higher ratio of sugar chains in which fucose is not bound to the complex type N-glycoside-linked sugar chain bound to the Protein S than native Protein S present in healthy human blood.

More preferably, the Protein S composition of the present invention may be a Protein S composition comprising recombinant Protein S molecules having complex type N-glycoside-linked sugar chains, wherein the complex type N-glycoside-linked sugar chains are sugar chains in which fucose is not bound to N-acetylglucosamine in the reducing end in the sugar chain.

In the present invention, the N-glycoside-linked sugar chain bound to Protein S has a common core structure of the following structural formula (I), even though it has a variety of structures.

[Chem 1]

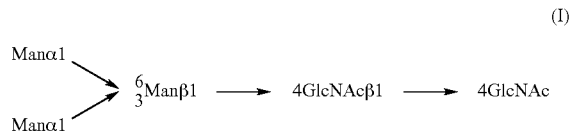

(I)

In structural formula (I), the sugar chain terminus which binds to asparagine is referred to as a reducing end, and the opposite side is referred to as a non-reducing end. The N-glycoside-linked sugar chain is classified into the following exemplified three types, depending on structural characteristics: a high mannose type in which mannose alone binds to the non-reducing end of the core structure; a complex type in which the non-reducing end side of the core structure has one or more parallel branches, specifically 2 to 4 branches, containing a lactosamine structure formed of galactose-N-acetylglucosamine (hereinafter referred to as "Gal-GlcNAc") and the non-reducing end side of Gal-GlcNAc has a structure of sialic acid, bisecting N-acetylglucosamine or the like; and a hybrid type in which the non-reducing end side of the core structure has branches of both of the high mannose type and complex type.

In the present invention, at least three sites of N-glycoside-linked sugar chain addition sequences exist in Protein S molecules constituting the Protein S composition, and an N-glycoside-linked sugar chain binds to at least one site of them. Specific examples of the binding site of the complex type N-glycoside-linked sugar chain may include asparagine residues at positions 458, 468 and 489 from the N-terminal of the amino acid sequence of the Protein S.

A specific example of the N-glycoside-linked sugar chain which binds to Protein S molecules contained in the Protein S composition of the present invention may include the above-mentioned complex type N-glycoside-linked sugar chain, preferably a complex type sugar chain in which sialic acid is bound to galactose in the non-reducing end thereof.

Examples of the sugar chain in which sialic acid is bound to galactose in the non-reducing end of sugar chain may include a sugar chain in which 2-position of sialic acid is bound to 6-position of galactose through α-bond, a sugar chain in which 2-position of sialic acid is bound to 3-position of galactose through α-bond, and the like.

As the complex type N-glycoside-linked sugar chain that binds to Protein S molecule includes any sugar chain containing the core structure represented by the above-described structural formula (I), there are a large number of combinations of sugar chains.

Accordingly, if the Protein S composition of the present invention is a Protein S composition having a higher binding activity to RAGE than the native Protein S and also having a higher ratio of a sugar chain in which fucose is not bound to a complex type N-glycoside-linked sugar chain bound to Protein S than native Protein S present in healthy human blood, Protein S molecules contained in the composition may consist of Protein S molecules having a single sugar chain structure or may consist of Protein S molecules having a plurality of different sugar chain structures.

The term "sugar chains in which fucose is not bound to N-acetylglucosamine in the reducing end in the complex type N-glycoside-linked sugar chains" includes any one, so long as they are sugar chains in which fucose is not bound to N-acetylglucosamine in the complex type N-glycoside-linked sugar chains. In this case, the structures of the sugar chains in the non-reducing end may have variety. Examples include a sugar chain in which 1-position of fucose is not bound to 6-position of N-acetylglucosamine of the complex type N-glycoside-linked sugar chain through α-bond, a sugar chain in which 1-position of fucose is not bound to 3-position of N-acetylglucosamine of the complex type N-glycoside-linked sugar chain through α-bond, and the like.

The term "Protein S composition of the present invention having a higher ratio of sugar chains in which fucose is not bound to the complex type N-glycoside-linked sugar chains bound to the Protein S than native Protein S present in healthy human blood" means that the ratio of Protein S having complex type N-glycoside-linked sugar chains to which fucose is not bound present in the composition is higher than the ratio of native Protein S having complex type N-glycoside-linked sugar chains to which fucose is not bound present in healthy human blood.

Since the ratio of fucose-free Protein S present in healthy human blood is less than about 70%, the ratio of fucose-free Protein S in the Protein S composition of the present invention is 70% or more, preferably 74% or more, 75% or more, 80% or more, 85% or more, more preferably 90% or more, 95% or more, 96% or more, 97% or more, 98% or more, 99% or more, and most preferably 100%.

The structural analysis of a sugar chain in a composition comprising Protein S molecules having complex type N-glycoside-linked sugar chains can be determined by releasing the sugar chain from Protein S molecules by known methods such as hydrazinolysis and enzyme digestion [*Seibutsukagaku Jikkenho (Biochemical Experimentation Methods)* 23—*Totanpakushitsu Tosa Kenkyuho (Methods of Studies on Glycoprotein Sugar Chains)*, Gakkai Shuppan Center, edited by Reiko Takahashi (1989)], labeling the released sugar chains with a fluorescent substance or radioisotope, and separating the labeled sugar chains by chromatography. Alternatively, the released sugar chains may be analyzed by the HPAED-PAD method [*J. Liq. Chromatogr.*, 6, 1577 (1983)] to determine the ratio.

The term "fucose is not bound to the N-acetylglucosamine in the reducing end in the sugar chains" of the present invention means that fucose is not substantially bound thereto, preferably means that the content rate of fucose is 0%. The term "Protein S composition in which fucose is not substantially bound" specifically refers to an antibody composition in which fucose is not substantially detected, when subjected to the sugar chain analysis described in 4 below. The level which fucose is not substantially detected means that the content of fucose is below the detection limit under analysis of sugar chain.

The Protein S composition of the present invention exhibits a higher affinity for the pattern recognition receptor family such as RAGE than the Protein S in which fucose is bound to N-acetylglucosamine in the reducing end of a complex type N-glycoside-linked sugar chain, such as conventionally known human plasma-derived or recombinant Protein S, and also exerts a potent anti-inflammatory effect by inhibiting the secretion of inflammatory cytokines from lymphocytes or vascular endothelial cells.

In the present invention, the receptor for advanced glycation end products (RAGE), isolated in 1992 by Stem et al., and also called another name AGER (Advanced glycosylation end product-specific receptor), is a protein belonging to the immunoglobulin superfamily (*J Biol Chem* 267, 14998 (1992)), and includes any protein, so long as it has a binding activity to advanced glycation end products (AGEs), high mobility group box chromosomal protein (HMGB), S100 (soluble in 100% saturated ammonium sulfate) peptide (Calgranulin) family, Amphoterin, β-amyloid, carboxyl methylidene/modification protein, and the like. Further, RAGE belongs to the pattern recognition receptor (PRR) family, similar to Toll-like receptor, and is directly and/or indirectly involved alone or in combination with other PRR families in natural immunity or acquired immunity. Specific examples of RAGE may include the following proteins (a), (b), (c) and (d), and the like.

(a) Full-length membrane-bound RAGE having an immunoglobulin-like V-type domain and two C-type domains, a transmembrane domain, and an intracellular domain in the extracellular region thereof;

(b) Dominant negative RAGE (dnRAGE) having an immunoglobulin-like V-type domain and two C-type domains, and a transmembrane domain in the extracellular region thereof, and lacking an intracellular domain;

(c) Secretory (soluble) RAGE (esRAGE) having an immunoglobulin-like V-type domain and two C-type domains, and a transmembrane domain in the extracellular region thereof, and lacking a transmembrane domain and an intracellular domain;

(d) N-truncated RAGE (ntRAGE) having two immunoglobulin-like C-type domains, a transmembrane domain, and an intracellular domain in the extracellular region thereof, and lacking an extracellular V-type domain.

Further, the fucose-free Protein S composition of the present invention exhibits a higher binding activity to CD14 (Science 239, 497-500, 1988, NCBI reference sequence: NP_000582.1) than native Protein S present in healthy human blood.

In the present invention, CD14 (Lipopolysaccharide/LPS binding protein-receptor; LPS/LBP-R) belongs to the PRR family, similar to RAGE or Toll-like receptors, is a single transmembrane glycoprotein consisting of 356 amino acids, is expressed on the surface of vascular endothelium, monocytes, neutrophils or dendritic cells activated under inflammatory conditions, and is known as a monocyte differentiation antigen (NCBI reference sequence: NP_000582.1). Further, it is also known that the concentration of soluble CD14 in plasma of patients is significantly elevated, when inflammation is excessively increased to cause multi-organ failure in the human. In addition, it is known that when a ligand, i.e., lipopolysaccharide (LPS)-LPS binding protein complex, binds to CD14, signals causing intracellular inflammatory responses are transferred to increase the production of HMGB-1 and the like. From these facts, similar to RAGE, CD14 is also known as an inflammatory mediator in inflammatory diseases such as sepsis.

A cell producing the Protein S composition of the present invention includes any type of cells, so long as it is a cell that can produce the Protein S composition of the present invention. Specifically, it may be a cell that is obtained by introducing a DNA encoding a Protein S molecule into a host cell of the following (a) to (c):

(a) a cell in which genome is modified so as to delete the activity of an enzyme relating to the synthesis of an intracellular sugar nucleotide, GDP-fucose;

(b) a cell in which genome is modified so as to delete the activity of an enzyme relating to the modification of a sugar chain in which 1-position of fucose is bound to 6-position of N-acetylglucosamine in the reducing end through α-bond in a complex type N-glycoside-linked sugar chain; and (c) a cell in which genome is modified so as to delete the activity of a protein relating to the transportation of an intracellular sugar nucleotide, GDP-fucose to the Golgi apparatus.

Examples of the enzymes relating to the synthesis of the intracellular sugar nucleotide, GDP-fucose may include GDP-mannose 4,6-dehydratase (GMD), GDP-4-keto-6-deoxy-D-mannose-3,5-epimerase (Fx), and the like. Examples of the enzymes relating to the modification of a sugar chain in which 1-position of fucose is bound to 6-position of N-acetylglucosamine in the reducing end through α-bond in a complex type N-glycoside-linked sugar chain may include α1,6-fucosyltransferase, and the like. Examples of the protein relating to the transportation of an intracellular sugar nucleotide, GDP-fucose to the Golgi apparatus may include GDP-fucose transporter, and the like.

The host cell may be preferably a host cell in which a gene encoding host intracellular α1,6-fucosyltransferase was knocked out (WO02/31140 and WO03/85107).

Further, a cell producing the Protein S composition of the present invention can be obtained by introducing a DNA encoding Protein S molecule to host cell which delete activity of the above-mentioned enzymes, i.e., the cell in which genome is modified so as to delete the activity of an enzyme relating to the synthesis of intracellular sugar nucleotide, GDP-fucose, an enzyme relating to the modification of a sugar chain in which 1-position of fucose is bound to 6-position of N-acetylglucosamine in the reducing end through α-bond in a complex type N-glycoside-linked sugar chain, or a protein relating to the transportation of an intracellular sugar nucleotide, GDP-fucose to the Golgi apparatus.

As used herein, the term "genome is modified so as to delete the activity of an enzyme relating to the synthesis of intracellular sugar nucleotide, GDP-fucose, an enzyme relating to the modification of a sugar chain in which 1-position of fucose is bound to 6-position of N-acetylglucosamine in the reducing end through α-bond in a complex type N-glycoside-linked sugar chain, or a protein relating to the transportation of an intracellular sugar nucleotide, GDP-fucose to the Golgi apparatus" refers to introduction of mutation into an expression regulation region of a gene encoding the enzyme so as to delete the expression of the enzyme or introduction of mutation in the amino acid sequence of a gene encoding the enzyme so as to inactivate functions of the enzyme. The "introduction of mutation" refers to carrying out modification of the nucleotide sequence on the genome such as deletion, substitution, insertion and/or addition in the nucleotide sequence. Complete suppression of the expression or function of the thus modified genomic gene is referred to as "knock out". Specific examples of genomic gene knockout may include complete or partial depletion of a target gene from the genome. Knockout may be carried out by eliminating a genomic region of an exon containing an initiation codon of the target gene from the chromosome.

For example, the following techniques can be employed for deleting the above enzyme activity:
(a) gene disruption targeting at a gene encoding the enzyme;
(b) introduction of a dominant-negative mutant of a gene encoding the enzyme;
(c) introduction of a mutation into the enzyme;
(d) suppression of transcription or translation of a gene encoding the enzyme;
(e) selection of a cell line resistant to a lectin which recognizes a sugar chain structure in which 1-position of fucose is bound to 6-position of N-acetylglucosamine in the reducing end through α-bond in a complex type N-glycoside-linked sugar chain.

As the lectin which recognizes a sugar chain structure in which 1-position of fucose is bound to 6-position of N-acetylglucosamine in the reducing end through α-bond in a complex type N-glycoside-linked sugar chain, any lectin capable of recognizing the sugar chain structure can be used. Specific examples include lentil lectin LCA (lentil agglutinin derived from *Lens culinaris*), pea lectin PSA (pea lectin derived from *Pisum sativum*), broad bean lectin VFA (agglutinin derived from *Vicia faba*), *Aleuria aurantia* lectin AAL (lectin derived from *Aleuria aurantia*) and the like.

The term "cell resistant to a lectin" refers to a cell in which growth is not inhibited by presence of a lectin at an effective concentration. The "effective concentration" is a concentration higher than the lowest concentration that does not allow the normal growth of a cell prior to the genome modification (hereinafter referred to also as parent cell line), preferably equal to the concentration that does not allow the normal growth of a cell prior to the genome modification, more preferably 2 to 5 times, further preferably 10 times, most preferably 20 or more times as much as the concentration that does not allow the normal growth of a cell prior to the modification of the genomic gene.

The effective concentration of lectin that does not inhibit growth may be appropriately determined according to each cell line. It is usually 10 μg/mL to 10 mg/mL, preferably 0.5 mg/mL to 2.0 mg/mL.

The host cell for producing the Protein S composition of the present invention may be any of the above host cells capable of expressing the Protein S composition of the present invention. For example, yeast cells, animal cells, insect cells and plant cells can be used. Examples of the cells include those described in 2 below. Specifically, examples of animal cells include CHO cell derived from Chinese hamster ovary tissue, rat myeloma cell line YB2/3HL.P2.G11.16Ag.20, mouse myeloma cell line NS0, mouse myeloma cell line SP2/0-Ag14, BHK cell derived from Syrian hamster kidney tissue, an antibody-producing hybridoma cell, human leukemia cell line Namalwa, PER.C6 cell derived from human retinoblastoma, HEK293 cell derived from human embryonic kidney, NM-F9 cell human myelocytic leukemia, an embryonic stem cell and a fertilized egg cell and the like. Preferable examples include a host cell for the production of pharmaceutical recombinant glycoprotein products, an embryonic stem cell or fertilized egg cell employed for preparing a non-human transgenic animal producing pharmaceutical recombinant glycoprotein products, a plant cell employed for preparing a transgenic plant producing pharmaceutical recombinant glycoprotein products and the like.

The parent cell includes a cell prior to the application of a technique to modify a genomic gene of an enzyme relating to the synthesis of intracellular sugar nucleotide, GDP-fucose, an enzyme relating to the modification of a sugar chain in which 1-position of fucose is bound to 6-position of N-acetylglucosamine in the reducing end through α-bond in a complex type N-glycoside-linked sugar chain, or a protein relating to the transportation of an intracellular sugar nucleotide, GDP-fucose to the Golgi apparatus. For example, the following cells may be appropriately exemplified.

The parent cell of NS0 cell includes NS0 cells described in literatures such as *BIO/TECHNOLOGY*, 10, 169 (1992) and *Biotechnol. Bioeng.*, 73, 261 (2001). Also, it includes cell line NS0 (RCB0213) registered at RIKEN Cell Bank, The Institute of Physical and Chemical Research, sub-cell lines obtained by adapting these cell lines to various serum-free media in which they can grow, and the like.

The parent cell of SP2/0-Ag14 cell includes SP2/0-Ag14 cells described in literatures such as J. Immunol., 126, 317 (1981), Nature, 276, 269 (1978) and Human Antibodies and Hybridomas, 3, 129 (1992). Also, it includes SP2/0-Ag14 cell (ATCC CRL-1581) registered at ATCC, sub-cell lines obtained by adapting these cell lines to various serum-free media in which they can grow (ATCC CRL-1581.1) and the like.

The parent cell of CHO cell derived from Chinese hamster ovary tissue includes CHO cells described in literatures such as *Journal of Experimental Medicine*, 108, 945 (1958), *Proc. Natl. Acad. Sci. USA,* 60, 1275 (1968), *Genetics,* 55, 513 (1968), *Chromosoma,* 41, 129 (1973), Methods in Cell Science, 18, 115 (1996), *Radiation Research,* 148, 260 (1997), *Proc. Natl. Acad. Sci. USA,* 77, 4216 (1980), *Proc. Natl. Acad. Sci. USA,* 60, 1275 (1968), Cell, 6, 121 (1975) and *Molecular Cell Genetics*, Appendix I, II (p. 883-900). Also, it includes cell line CHO-K1 (ATCC CCL-61), cell line DUXB11 (ATCC CRL-9096) and cell line Pro-5 (ATCC CRL-1781) registered at ATCC, commercially available cell line CHO-S (Cat # 11619 of Lifetechnologies), sub-cell lines obtained by adapting these cell lines to various serum-free media in which they can grow, and the like.

The parent cell of a rat myeloma cell line YB2/3HL.P2.G11.16Ag.20 cell includes cell lines established from Y3/Ag1.2.3 cell (ATCC CRL-1631) such as YB2/3HL.P2.G11.16Ag.20 cell described in literatures such as J.

Cell. Biol., 93, 576 (1982) and Methods Enzymol., 73B, 1 (1981). Also, it includes YB2/3HL.P2.G11.16Ag.20 cell (ATCC CRL-1662) registered at ATCC, sub-lines obtained by adapting these cell lines to various serum-free media in which they can grow, and the like.

Specific examples of the cell producing the Protein S composition of the present invention may include a cell line after serum-free medium adaptation of the transformant obtained by the introduction of the Protein S-encoding gene into a CHO cell in which the α1,6-fucosyltransferase-encoding gene is knocked out, a cell line after serum-free medium adaptation of the transformant obtained by the introduction of the Protein S-encoding gene into a CHO cell in which the GDP-mannose 4,6-dehydratase-encoding gene is knocked out, a cell line after serum-free medium adaptation of the transformant obtained by the introduction of the Protein S-encoding gene into a CHO cell in which the GDP-fucose transporter encoding gene is knocked out, or the like.

Examples of the transgenic animal of the present invention may include transgenic animals in which a genomic gene is modified so as to delete the activity of an enzyme relating to the synthesis of intracellular sugar nucleotide, GDP-fucose, an enzyme relating to the modification of a sugar chain in which 1-position of fucose is bound to 6-position of N-acetylglucosamine in the reducing end through α-bond in a complex type N-glycoside-linked sugar chain, or a protein relating to the transportation of an intracellular sugar nucleotide, GDP-fucose to the Golgi apparatus.

Specific examples may include an animal in which the Protein S-encoding gene is introduced into a transgenic animal in which the α1,6-fucosyltransferase-encoding gene is knocked out, an animal in which the Protein S-encoding gene is introduced into a transgenic animal in which the GDP-mannose 4,6-dehydratase-encoding gene is knocked out, an animal in which the Protein S-encoding gene is introduced into a transgenic animal in which the GDP-fucose transporter encoding gene is knocked out, or the like.

The transformant of the present invention can be produce the Protein S composition having a high affinity for RAGE and also exerting a remarkably higher anti-inflammatory effect than the Protein S composition obtained from the parent cell.

The blood coagulation inhibitory activity, half-life in blood, binding activity to RAGE, and anti-inflammatory effect of the Protein S composition can be measured by already known in vitro tests or in vivo tests using an animal model such as mice, rats, or rabbits, or clinical tests employing a human [*JBC* 256, 11128 (1981), *JBC* 270, 27852 (1995), *JBC* 272, 20678 (1997), *JBC* 261, 12022 (1986), Thromb Haemost 85, 761 (2001), *JBC* 268, 2872 (1993), *PNAS* 91, 2728 (1994), *Blood* 86, 1062 (1995), *Thromb Haemost* 80, 930 (1998), *Thromb Haemost* 82, 80 (1999), *Arterioscler Thromb Vasc Biol* 25, 2209 (2005), Eur J Immunol 38, 809 (2008), *Arthritis Rheumatism* 54, 3898 (2006), *Critical Care* 11, R122 (2007), *Blood* 86, 2642 (1995), *J Clin Invest* 95, 1987 (1995), *Thromb Haemost* 90, 227 (2003)].

The present invention is described below in detail.

1. Preparation of a Cell for Producing the Protein S Composition of the Present Invention The cell producing the Protein S composition of the present invention can be prepared by the following manner.

(1) Gene Disruption Technique Targeting at a Gene Encoding an Enzyme

The host cell used for the production of the Protein S composition of the present invention can be prepared by a gene disruption technique targeting a gene encoding an enzyme relating to the synthesis of an intracellular sugar nucleotide, GDP-fucose or an enzyme relating to the modification of a sugar chain in which 1-position of fucose is bound to 6-position of N-acetylglucosamine in the reducing end through α-bond in a complex type N-glycoside-linked sugar chain or an protein relating the transportation of an intracellular sugar nucleotide, GDP-fucose to the Golgi apparatus (hereinafter referred to as enzyme relating to a fucose modification). Examples of the enzymes relating to the synthesis of an intracellular sugar nucleotide, GDP-fucose include GDP-mannose 4,6-dehydratase (hereinafter referred to as GMD) and GDP-4-keto-6-deoxy-D-mannose-3,5-epimerase (hereinafter referred to as Fx). Examples of the enzymes relating to the modification of a sugar chain in which 1-position of fucose is bound to 6-position of N-acetylglucosamine in the reducing end through α-bond in a complex type N-glycoside-linked sugar chain include α1,6-fucosyltransferase, α-L-fucosidase and the like. In addition, examples of the protein relating the transportation of an intracellular sugar nucleotide, GDP-fucose to the Golgi apparatus include GDP-fucose transporter and the like.

The gene as used herein includes DNA and RNA.

The method of gene disruption may be any method capable of disrupting the gene encoding the target enzyme. Useful methods include the antisense method, the ribozyme method, the homologous recombination method, the RNA-DNA oligonucleotide method (hereinafter referred to as the RDO method), the RNA interference method (hereinafter referred to as the RNAi method), the method using a retrovirus and the method using a transposon. These methods are specifically described below.

(a) Preparation of the Host Cell for Producing the Protein S Composition of the Present Invention by the Antisense Method or the Ribozyme Method The host cell used for the production of the Protein S composition of the present invention can be prepared by the antisense method or the ribozyme method described in *Cell Technology*, 12, 239 (1993); *BIO/TECHNOLOGY*, 17, 1097 (1999); *Hum. Mol. Genet.*, 5, 1083 (1995); *Cell Technology*, 13, 255 (1994); *Proc. Natl. Acad. Sci. U.S.A.*, 96, 1886 (1999); etc. targeting at a gene encoding an enzyme relating to the synthesis of an intracellular sugar nucleotide, GDP-fucose or an enzyme relating to the modification of a sugar chain in which 1-position of fucose is bound to 6-position of N-acetylglucosamine in the reducing end through α-bond in a complex type N-glycoside-linked sugar chain, for example, in the following manner. A cDNA or a genomic DNA encoding an enzyme relating to the fucose modification is prepared. The nucleotide sequence of the prepared cDNA or genomic DNA is determined. Based on the determined DNA sequence, an antisense gene or a ribozyme of appropriate length is designed which comprises a DNA moiety encoding the enzyme relating to the fucose modification, non-translated regions or introns. In order to express the antisense gene or ribozyme in a cell, a recombinant vector is prepared by inserting a fragment or full-length of the prepared DNA into a site downstream of a promoter in an appropriate expression vector. The recombinant vector is introduced into a host cell suited for the expression vector to obtain a transformant.

The host cell used for the production of the Protein S composition of the present invention can be obtained by selecting a transformant using, as an index, the activity of the enzyme relating to the fucose modification. The host cell used for the production of the Protein S composition of the present invention can also be obtained by selecting a transformant using, as an index, the sugar chain structure of a glycoprotein on the cell membrane or the sugar chain structure of the produced Protein S molecule.

As the host cell used for the production of the Protein S composition of the present invention, any yeast cell, animal cell, insect cell, plant cell, or the like can be used so long as it has a gene encoding the target enzyme relating to the fucose modification. Examples of the host cells include those described in 3 below.

The expression vectors that can be employed are those capable of autonomous replication or integration into the chromosome in the above host cells and comprising a promoter at a position appropriate for the transcription of the designed antisense gene or ribozyme. Examples of the expression vectors include those described in 3 below.

Introduction of a gene into various host cells can be carried out by the methods suitable for introducing a recombinant vector into various host cells described in 3 below.

Selection of a transformant using, as an index, the activity of an enzyme relating to the fucose modification can be carried out, for example, by the following methods.
Methods for Selecting a Transformant A cell in which the activity of an enzyme relating to the fucose modification is deleted can be selected by measuring the activity of the enzyme relating to the fucose modification using biochemical methods or genetic engineering techniques described in the literature [*Shin Seikagaku Jikken Koza* (*New Lectures on Experiments in Biochemistry*) 3—*Saccharides I, Glycoprotein* (Tokyo Kagaku Dojin), edited by The Japanese Biochemical Society (1988)]; the literature [*Cell Technology, Extra Edition, Experimental Protocol Series, Glycobiology Experimental Protocol, Glycoprotein, Glycolipid and Proteoglycan* (Shujunsha), edited by Naoyuki Taniguchi, Akemi Suzuki, Kiyoshi Furukawa and Kazuyuki Sugawara (1996)]; *Molecular Cloning*, Second Edition, *Current Protocols in Molecular Biology*; and the like. An example of the biochemical methods is a method in which the enzyme activity is evaluated using an enzyme-specific substrate. Examples of the genetic engineering techniques include Northern analysis and RT-PCR in which the amount of mRNA for a gene encoding the enzyme is measured.

Selection of a transformant using, as an index, the sugar chain structure of a glycoprotein on the cell membrane can be carried out, for example, by the method described in 5 below. Selection of a transformant using, as an index, the sugar chain structure of a produced glycoprotein molecule can be carried out, for example, by the methods described in 5 below.

Preparation of a cDNA encoding an enzyme relating to the fucose modification can be carried out, for example, by the following method.
Preparation Method of cDNA Total RNA or mRNA is prepared from various tissues of host cells or cell. A cDNA library is prepared from the total RNA or mRNA. Degenerative primers are prepared based on the amino acid sequence of an enzyme relating to the synthesis of an intracellular sugar nucleotide, GDP-fucose or an enzyme relating to the modification of a sugar chain in which 1-position of fucose is bound to 6-position of N-acetylglucosamine in the reducing end through α-bond in a complex type N-glycoside-linked sugar chain, and a gene fragment encoding the enzyme relating to the fucose modification is obtained by PCR using the prepared cDNA library as a template.

A DNA encoding the enzyme relating to the fucose modification can be obtained by screening the cDNA library using the obtained gene fragment as a probe.

As the mRNA of a human or non-human animal tissues or cells, commercially available one (for example, manufactured by Clontech) may be used, or it may be prepared from a human or non-human animal tissues or cells in the following manner.

The methods for preparing total RNA from a human or non-human animal tissue or cell include the guanidine thiocyanate-cesium trifluoroacetate method [*Methods in Enzymology*, 154, 3 (1987)], the acidic guanidine thiocyanate-phenol-chloroform (AGPC) method [*Analytical Biochemistry*, 162, 156 (1987); *Experimental Medicine*, 9, 1937 (1991)] and the like.

The methods for preparing mRNA as poly(A)$^+$RNA from the total RNA include the oligo (dT) immobilized cellulose column method [*Molecular Cloning*, Second Edition, Cold Spring Harbor Laboratory Press (1989)].

It is also possible to prepare mRNA by using a commercially available kit such as Fast Track mRNA Isolation Kit (manufactured by Invitrogen) or Quick Prep mRNA Purification Kit (manufactured by Pharmacia).

A cDNA library is prepared from the obtained mRNA of a human or non-human animal tissue or cell. The methods for preparing the cDNA library include the methods described in *Molecular Cloning*, Second Edition, *Current Protocols in Molecular Biology, A Laboratory Manual*, 2nd Ed. (1989); etc., and methods using commercially available kits such as SuperScript Plasmid System for cDNA Synthesis and Plasmid Cloning (manufactured by Life Technologies) and ZAP-cDNA Synthesis Kit (manufactured by STRATAGENE).

As the cloning vector for preparing the cDNA library, any vector, e.g. phage vectors and plasmid vectors, can be used so long as they are autonomously replicable in *Escherichia coli* K12. Examples of suitable vectors include ZAP Express [manufactured by STRATAGENE; *Strategies*, 5, 58 (1992)], pBluescript II SK(+) [*Nucleic Acids Research*, 17, 9494 (1989)], λZAP II (manufactured by STRATAGENE), λgt10, λgt11 [*DNA Cloning, A Practical Approach*, 1, 49 (1985)], λTriplEx (manufactured by Clontech), λExCell (manufactured by Pharmacia), pT7T318U (manufactured by Pharmacia), pcD2 [*Mol. Cell. Biol.*, 3, 280 (1983)] and pUC18 [*Gene*, 33, 103 (1985)].

Any microorganism can be used as the host microorganism for preparing the cDNA library, but *Escherichia coli* is preferably used. Examples of suitable host microorganisms are *Escherichia coli* XL1-Blue MRF' [manufactured by STRATAGENE; *Strategies*, 5, 81 (1992)], *Escherichia coli* C600 [*Genetics*, 39, 440 (1954)], *Escherichia coli* Y1088 [*Science*, 222, 778 (1983)], *Escherichia coli* Y1090 [*Science*, 222, 778 (1983)], *Escherichia coli* NM522 [*J. Mol. Biol.*, 166, 1 (1983)], *Escherichia coli* K802 [*J. Mol. Biol.*, 16, 118 (1966)] and *Escherichia coli* JM105 [*Gene*, 38, 275 (1985)].

The cDNA library may be used as such in the following analysis. Alternatively, in order to efficiently obtain full-length cDNAs by decreasing the ratio of partial cDNAs, a cDNA library prepared using the oligo-cap method developed by Sugano, et al. [*Gene*, 138, 171 (1994); *Gene*, 200, 149 (1997); *Protein, Nucleic Acid and Enzyme*, 41, 603 (1996); *Experimental Medicine*, 11, 2491 (1993); *cDNA Cloning* (Yodosha) (1996); *Methods for Preparing Gene Libraries* (Yodosha) (1994)] may be used in the following analysis.

Degenerative primers specific for the 5'-terminal and 3'-terminal nucleotide sequences of a nucleotide sequence presumed to encode the amino acid sequence of an enzyme relating to the fucose modification are prepared based on the amino acid sequence of the enzyme. A gene fragment encoding the enzyme relating to the fucose modification can be obtained by DNA amplification by PCR [*PCR Protocols*, Academic Press (1990)] using the prepared cDNA library as a template.

It can be confirmed that the obtained gene fragment is a DNA encoding the enzyme relating to the fucose modification by analyzing the nucleotide sequence by generally employed nucleotide sequence analyzing methods such as the dideoxy method of Sanger, et al. [*Proc. Natl. Acad. Sci. U.S.A.*, 74, 5463 (1977)] or by use of nucleotide sequence analyzers such as ABI PRISM 377 DNA Sequencer (manufactured by Applied Biosystems).

A DNA encoding the enzyme relating to the fucose modification can be obtained from the cDNA or cDNA library synthesized from the mRNA contained in a human or non-human animal tissue or cell by colony hybridization or plaque hybridization [*Molecular Cloning*, Second Edition, Cold Spring Harbor Laboratory Press (1989)] using the above gene fragment as a probe.

A cDNA encoding the enzyme relating to the fucose modification can also be obtained by amplification by PCR using the cDNA or cDNA library synthesized from the mRNA contained in a human or non-human animal tissue or cell as a template and using the primers used for obtaining the gene fragment encoding the enzyme relating to the fucose modification.

The nucleotide sequence of the obtained DNA encoding the enzyme relating to the fucose modification can be determined by generally employed nucleotide sequence analyzing methods such as the dideoxy method of Sanger, et al. [*Proc. Natl. Acad. Sci. U.S.A.*, 74, 5463 (1977)] or by use of nucleotide sequence analyzers such as ABI PRISM 377 DNA Sequencer (manufactured by Applied Biosystems).

By carrying out a search of nucleotide sequence databases such as GenBank, EMBL or DDBJ using a homology search program such as BLAST based on the determined nucleotide sequence of the cDNA, it can be confirmed that the obtained DNA is a gene encoding the enzyme relating to the fucose modification among the genes in the nucleotide sequence database.

Examples of the nucleotide sequences of the genes encoding the enzyme relating to the synthesis of an intracellular sugar nucleotide, GDP-fucose obtained by the above methods include the nucleotide sequences of GDP-mannose 4,6-dehydratase, and GDP-4-keto-6-deoxy-D-mannose-3,5-epimerase described in WO2005/035741.

Examples of the nucleotide sequences of the genes encoding the enzyme relating to the modification of a sugar chain in which 1-position of fucose is bound to 6-position of N-acetylglucosamine in the reducing end through α-bond in a complex type N-glycoside-linked sugar chain obtained by the above methods include the nucleotide sequence of α1,6-fucosyltransferase described in U.S. Pat. No. 7,393,683.

Examples of the protein relating the transportation of an intracellular sugar nucleotide, GDP-fucose to the Golgi apparatus obtained by the above methods include the nucleotide sequence of GDP-fucose transporter described in US2004/0110282.

The cDNA encoding the enzyme relating to the synthesis of an intracellular sugar nucleotide, GDP-fucose or the enzyme relating to the fucose modification can also be obtained by chemical synthesis with a DNA synthesizer such as DNA Synthesizer Model 392 (manufactured by Perkin Elmer) utilizing the phosphoamidite method based on the determined nucleotide sequence of the DNA.

Preparation of a Genomic DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing end through α-bond in a complex type N-glycoside-linked sugar chain can be carried out, for example, by the following method.

Method for Preparing Genomic DNA

The genomic DNA can be prepared by known methods described in *Molecular Cloning*, Second Edition, *Current Protocols in Molecular Biology*; etc. In addition, the genomic DNA encoding the enzyme relating to the fucose modification can be obtained by using a kit such as Genomic DNA Library Screening System (manufactured by Genome Systems) or Universal GenomeWalker™ Kits (manufactured by CLONTECH).

The nucleotide sequence of the obtained DNA encoding the enzyme relating to the fucose modification can be determined by generally employed nucleotide analyzing methods such as the dideoxy method of Sanger, et al. [*Proc. Natl. Acad. Sci. U.S.A.*, 74, 5463 (1977)] or by use of nucleotide sequence analyzers such as ABI PRISM 377 DNA Sequencer (manufactured by Applied Biosystems).

By carrying out a search of nucleotide sequence databases such as GenBank, EMBL or DDBJ using a homology search program such as BLAST based on the determined nucleotide sequence of the genomic DNA, it can be confirmed that the obtained DNA is a gene encoding the enzyme relating to the fucose modification among the genes in the nucleotide sequence database.

The genomic DNA encoding the enzyme relating to the fucose modification can also be obtained by chemical synthesis with a DNA synthesizer such as DNA Synthesizer Model 392 (manufactured by Perkin Elmer) utilizing the phosphoamidite method based on the determined nucleotide sequence of the DNA.

The host cell used for the production of the Protein S composition of the present invention can also be obtained without using an expression vector by directly introducing into a host cell an antisense oligonucleotide or ribozyme designed based on the nucleotide sequence encoding the enzyme relating to the fucose modification.

The antisense oligonucleotide or ribozyme can be prepared by known methods or by using a DNA synthesizer. Specifically, based on the sequence information on an oligonucleotide having a sequence corresponding to 5 to 150, preferably 5 to 60, more preferably 10 to 40 contiguous nucleotides in the nucleotide sequence of the cDNA and genomic DNA encoding the enzyme relating to the fucose modification, an oligonucleotide corresponding to the sequence complementary to the above oligonucleotide (antisense oligonucleotide) or a ribozyme comprising the oligonucleotide sequence can be synthesized.

The oligonucleotide includes oligo RNA and derivatives of the oligonucleotide (hereinafter referred to as oligonucleotide derivatives).

The oligonucleotide derivatives include an oligonucleotide derivative wherein the phosphodiester bond in the oligonucleotide is converted to a phosophorothioate bond, an oligonucleotide derivative wherein the phosphodiester bond in the oligonucleotide is converted to an N3'-P5' phosphoamidate bond, an oligonucleotide derivative wherein the ribose-phosphodiester bond in the oligonucleotide is converted to a peptide-nucleic acid bond, an oligonucleotide derivative wherein the uracil in the oligonucleotide is substituted with C-5 propynyluracil, an oligonucleotide derivative wherein the uracil in the oligonucleotide is substituted with C-5 thiazolyluracil, an oligonucleotide derivative wherein the cytosine in the oligonucleotide is substituted with C-5 propynylcytosine, an oligonucleotide derivative wherein the cytosine in the oligonucleotide is substituted with phenoxazine-modified cytosine, an oligonucleotide derivative wherein the ribose in the oligonucleotide is substituted with 2'-O-propylribose, and an oligonucleotide derivative wherein the ribose in the oligonucleotide is substituted with 2'-methoxyethoxyribose [*Cell Technology*, 16, 1463 (1997)].

(b) Preparation of the Host Cell for the Production of the Protein S Composition of the Present Invention by the Homologous Recombination Method The host cell used for the production of the Protein S composition of the present invention can be prepared by modifying a target gene on the chromosome by the homologous recombination method targeting a gene encoding an enzyme relating to the fucose modification.

Modification of the target gene on the chromosome can be carried out by using the methods described in *Manipulating the Mouse Embryo, A Laboratory Manual*, Second Edition, Cold Spring Harbor Laboratory Press (1994) (hereinafter referred to as *Manipulating the Mouse Embryo, A Laboratory Manual*), *Gene Targeting, A Practical Approach*, IRL Press at Oxford University Press (1993); *Biomanual Series* 8, *Gene Targeting Preparation of Mutant Mice Using ES Cells*, Yodosha (1995) (hereinafter referred to as *Preparation of Mutant Mice Using ES Cells*); etc., for example, in the following manner.

A genomic DNA encoding an enzyme relating to the fucose modification is prepared.

Based on the nucleotide sequence of the genomic DNA, a target vector is prepared for homologous recombination of a target gene to be modified (e.g., the structural gene or promoter gene for the enzyme relating to the fucose modification).

The host cell used for the preparation of the cell producing the Protein S composition of the present invention can be prepared by introducing the prepared target vector into a host cell and selecting a cell in which homologous recombination occurred between the target gene on the chromosome and the target vector.

As the host cell, any yeast cell, animal cell, insect cell, plant cell, or the like can be used so long as it has a gene encoding the target enzyme relating to the fucose modification. Examples of the host cells include those described in 3 below.

The genomic DNA encoding the enzyme relating to the fucose modification can be prepared by the methods for preparing a genomic DNA described in the above 1 (a), etc.

The target vector for use in the homologous recombination of the target gene on the chromosome can be prepared according to the methods described in *Gene Targeting, A Practical Approach*, IRL Press at Oxford University Press (1993); *Biomanual Series* 8, *Gene Targeting Preparation of Mutant Mice Using ES Cells*, Yodosha (1995); etc. The target vector may be either a replacement-type or an insertion-type.

Introduction of the target vector into various host cells can be carried out by the methods suitable for introducing a recombinant vector into various host cells described in 3 below.

The methods for efficiently selecting a homologous recombinant include positive selection, promoter selection, negative selection and polyA selection described in *Gene Targeting, A Practical Approach*, IRL Press at Oxford University Press (1993); *Biomanual Series* 8, *Gene Targeting, Preparation of Mutant Mice Using ES Cells*, Yodosha (1995); etc. The methods for selecting the desired homologous recombinant from the selected cell lines include Southern hybridization [*Molecular Cloning*, Second Edition, Cold Spring Harbor Laboratory Press (1989)] and PCR [*PCR Protocols*, Academic Press (1990)] with the genomic DNA.

(c) Preparation of the Host Cell for the Production of the Protein S Composition of the Present Invention by the RDO Method The host cell used for the production of the Protein S composition of the present invention can be prepared by the RDO method targeting a gene encoding an enzyme relating to the fucose modification, for example, in the following manner.

A cDNA or a genomic DNA encoding an enzyme relating to the synthesis of the intracellular sugar nucleotide, GDP-fucose or an enzyme relating to the modification of a sugar chain in which 1-position of fucose is bound to 6-position of N-acetylglucosamine in the reducing end through α-bond in a complex type N-glycoside-linked sugar chain is prepared by the methods described in the above 1.

The nucleotide sequence of the prepared cDNA or genomic DNA is determined.

Based on the determined DNA sequence, an RDO construct of appropriate length which comprises a DNA moiety encoding the enzyme relating to the fucose modification, non-translated regions or introns is designed and synthesized.

The host cell of the present invention can be obtained by introducing the synthesized RDO into a host cell and then selecting a transformant in which a mutation occurred in the target enzyme, that is, the enzyme relating to the fucose modification.

As the host cell, any yeast cell, animal cell, insect cell, plant cell, or the like can be used so long as it has a gene encoding the target enzyme relating to the fucose modification. Examples of the host cells include those described in 3 below.

Introduction of the RDO into various host cells can be carried out by the methods suitable for introducing a recombinant vector into various host cells described in 3 below.

The cDNA encoding the enzyme relating to the fucose modification can be prepared by the methods for preparing a cDNA described in the above 1 (a) or the like.

The genomic DNA encoding the enzyme relating to the fucose modification can be prepared by the methods for preparing a genomic DNA described in the above 1 (a) or the like.

After DNA is cleaved with appropriate restriction enzymes, the nucleotide sequence of the DNA can be determined by subcloning the DNA fragments into a plasmid such as pBluescript SK(−) (manufactured by Stratagene), subjecting the clones to the reaction generally used as a method for analyzing a nucleotide sequence such as the dideoxy method of Sanger et al. [*Proc. Natl. Acad. Sci. USA*, 74, 5463 (1977)] or the like, and then analyzing the clones by using an automatic nucleotide sequence analyzer such as ABI PRISM 377 DNA Sequencer (manufactured by Applied Biosystems) or the like.

The RDO can be prepared by conventional methods or by using a DNA synthesizer.

The methods for selecting a cell in which a mutation occurred by introducing the RDO into the host cell, in the gene encoding the target enzyme, that is, the enzyme relating to the fucose modification include the methods for directly detecting mutations in chromosomal genes described in *Molecular Cloning*, Second Edition, *Current Protocols in Molecular Biology*; etc.

For the selection of the transformant, the following methods can also be employed: the method using, as an index, the activity of the enzyme relating to the fucose modification described above; the method using, as an index, the sugar chain structure of a glycoprotein on the cell membrane described below; and the method using, as an index, the sugar chain structure of a produced glycoprotein molecule described above.

The RDO can be designed according to the descriptions in *Science*, 273, 1386 (1996); *Nature Medicine*, 4, 285 (1998); *Hepatology*, 25, 1462 (1997); *Gene Therapy*, 5, 1960 (1999); *J. Mol. Med.*, 75, 829 (1997); *Proc. Natl. Acad. Sci. USA*, 96, 8774 (1999); *Proc. Natl. Acad. Sci. USA*, 96, 8768 (1999); *Nuc. Acids Res.*, 27, 1323 (1999); *Invest. Dermatol.*, 111, 1172 (1998); *Nature Biotech.*, 16, 1343 (1998); *Nature Biotech.*, 18, 43 (2000); *Nature Biotech.*, 18, 555 (2000); etc.

(d) Preparation of the Host Cell for the Production of the Protein S Composition of the Present Invention by the RNAi Method The host cell used for the production of the Protein S composition of the present invention can be prepared by the RNAi method targeting a gene encoding an enzyme relating to the fucose modification, for example, in the following manner.

A cDNA encoding an enzyme relating to the fucose modification is prepared by the methods described in the above 1.

The nucleotide sequence of the prepared cDNA is determined.

Based on the determined cDNA sequence, an RNAi gene of appropriate length is designed which comprises a moiety encoding the enzyme relating to the fucose modification, or non-translated regions.

In order to express the RNAi gene in a cell, a recombinant vector is prepared by inserting a fragment or full-length of the prepared cDNA into a site downstream of a promoter in an appropriate expression vector.

The recombinant vector is introduced into a host cell suited for the expression vector to obtain a transformant.

The host cell used for the preparation of the cell of the present invention can be obtained by selecting a transformant using, as an index, the activity of the enzyme relating to the fucose modification, or the sugar chain structure of a produced glycoprotein molecule or a glycoprotein on the cell membrane.

As the host cell, any yeast cell, animal cell, insect cell, plant cell, or the like can be used so long as it has a gene encoding the target enzyme relating to the fucose modification. Examples of the host cells include those described in 3 below.

The expression vectors that can be employed are those capable of autonomous replication or integration into the chromosome in the above host cells and comprising a promoter at a position appropriate for the transcription of the designed RNAi gene. Examples of the expression vectors include those described in 3 below.

Introduction of a gene into various host cells can be carried out by the methods suitable for introducing a recombinant vector into various host cells described in 3 below.

The methods for selecting the transformant using, as an index, the activity of the enzyme relating to the fucose modification include the methods described in the above 1.

The methods for selecting the transformant using, as an index, the sugar chain structure of a glycoprotein on the cell membrane include the method described in the above 1. The methods for selecting the transformant using, as an index, the sugar chain structure of a produced glycoprotein molecule include the methods described in 5 below.

The methods for preparing cDNA encoding the enzyme relating to the fucose modification without using an expression vector include the methods for preparing a cDNA described in the above 1 (a), etc.

The host cell used for the preparation of the cell of the present invention can also be obtained without using an expression vector by directly introducing into a host cell the RNAi gene designed based on the nucleotide sequence encoding the enzyme relating to the fucose modification.

The RNAi gene can be prepared by known methods or by using a DNA synthesizer. The RNAi gene construct can be designed according to the descriptions in *Nature*, 391, 806 (1998); *Proc. Natl. Acad. Sci. USA*, 95, 15502 (1998); *Nature*, 395, 854 (1998); *Proc. Natl. Acad. Sci. USA*, 96, 5049 (1999); *Cell*, 95, 1017 (1998); *Proc. Natl. Acad. Sci. USA*, 96, 1451 (1999); *Proc. Natl. Acad. Sci. USA*, 95, 13959 (1998); *Nature Cell Biol.*, 2, 70 (2000); etc.

(e) Preparation of the Host Cell for the Production of the Protein S Composition of the Present Invention by the Method Using a Transposon The host cell used for the production of the Protein S composition of the present invention can be prepared by using the transposon system described in *Nature Genet.*, 25, 35 (2000), etc., and then selecting a mutant using, as an index, the activity of the enzyme relating to the fucose modification, or the sugar chain structure of a produced glycoprotein molecule or a glycoprotein on the cell membrane.

The transposon system is a system for inducing a mutation by random insertion of an exogenous gene into the chromosome, wherein usually an exogenous gene inserted into a transposon is used as a vector for inducing a mutation and a transposase expression vector for randomly inserting the gene into the chromosome is introduced into the cell at the same time.

Any transposase can be used so long as it is suitable for the sequence of the transposon to be used.

As the exogenous gene, any gene can be used so long as it can induce a mutation in the DNA of a host cell.

As the host cell, any yeast cell, animal cell, insect cell, plant cell, or the like can be used so long as it has a gene encoding the target enzyme relating to the fucose modification. Examples of the host cells include those described in 3 below. Introduction of the gene into various host cells can be carried out by the methods suitable for introducing a recombinant vector into various host cells described in 3 below.

The methods for selecting the mutant using, as an index, the activity of the enzyme relating to the fucose modification include the methods described in the above 1 (a).

The methods for selecting the mutant using, as an index, the sugar chain structure of a glycoprotein on the cell membrane include the method described in the above 1. The methods for selecting the mutant using, as an index, the sugar chain structure of a produced glycoprotein molecule include the methods described in 5 below.

(2) Technique of Introducing a Dominant-Negative Mutant of a Gene Encoding an Enzyme The host cell used for the production of the Protein S composition of the present invention can be prepared by using the method of introducing a dominant-negative mutant of a target gene, i.e., a gene encoding an enzyme relating to the synthesis of the intracellular sugar nucleotide, GDP-fucose or an enzyme relating to the modification of a sugar chain in which 1-position of fucose is bound to 6-position of N-acetylglucosamine in the reducing end through α-bond in a complex type N-glycoside-linked sugar chain. Examples of the enzymes relating to the synthesis of the intracellular sugar nucleotide, GDP-fucose include GMD and Fx. Examples of the enzymes relating to the modification of a sugar chain in which 1-position of fucose is bound to 6-position of N-acetylglucosamine in the reducing end through α-bond in a complex type N-glycoside-linked sugar chain include, in particular, α1,6-fucosyltransferase, α-L-fucosidase and the like. Examples of a protein relating to the transportation of GDP-fucose to the Golgi apparatus include, in particular, GDP-fucose transporter and the like.

These enzymes have substrate specificity and catalyze specific reactions. By disrupting the active center of such enzymes having substrate specificity and catalytic action, their dominant-negative mutants can be prepared. Preparation of a dominant-negative mutant is described in detail below, using for an example GMD among the target enzymes.

As a result of the analysis of the tertiary structure of GMD derived from *Escherichia coli*, it has been found that four amino acids (threonine at position 133, glutamic acid at position 135, tyrosine at position 157 and lysine at position 161) have an important function for the enzyme activity (*Structure*, 8, 2, 2000). That is, the mutants prepared by substituting the above four amino acids by other amino acids based on the tertiary structure information all showed significantly decreased enzyme activity. On the other hand, little change was observed in the ability of the mutants to bind to the GMD coenzyme NADP or the substrate GDP-mannose. Accordingly, a dominant-negative mutant can be prepared by substituting the four amino acids which are responsible for the enzyme activity of GMD. On the basis of the result of preparation of a dominant-negative mutant of GMD derived from *Escherichia coli*, dominant-negative mutants can be prepared by performing homology comparison and tertiary structure prediction using the amino acid sequence information. For example, in the case of GMD derived from CHO cell, a dominant-negative mutant can be prepared by substituting threonine at position 155, glutamic acid at position 157, tyrosine at position 179 and lysine at position 183 by other amino acids. Preparation of such a gene carrying introduced amino acid substitutions can be carried out by site-directed mutagenesis described in *Molecular Cloning*, Second Edition, *Current Protocols in Molecular Biology*; etc.

The host cell used for the production of the Protein S composition of the present invention can be prepared according to the method of gene introduction described in *Molecular Cloning*, Second Edition, *Current Protocols in Molecular Biology*, *Manipulating the Mouse Embryo A Laboratory Manual*, Second Edition; etc. using a gene encoding a dominant-negative mutant of a target enzyme (hereinafter abbreviated as dominant-negative mutant gene) prepared as above, for example, in the following manner.

A dominant-negative mutant gene encoding the enzyme relating to the fucose modification is prepared.

Based on the full-length DNA of the prepared dominant-negative mutant gene, a DNA fragment of appropriate length containing a region encoding the protein is prepared according to need.

A recombinant vector is prepared by inserting the DNA fragment or full-length DNA into a site downstream of a promoter in an appropriate expression vector.

The recombinant vector is introduced into a host cell suited for the expression vector to obtain a transformant.

The host cell used for the preparation of the cell for producing the Protein S composition of the present invention can be obtained by selecting a transformant using, as an index, the activity of the enzyme relating to the fucose modification, or the sugar chain structure of a produced Protein S molecule or a glycoprotein on the cell membrane.

As the host cell, any yeast cell, animal cell, insect cell, plant cell, or the like can be used so long as it has a gene encoding the target enzyme relating to the fucose modification. Examples of the host cells include those described in 3 below.

The expression vectors that can be employed are those capable of autonomous replication or integration into the chromosome in the above host cells and comprising a promoter at a position appropriate for the transcription of the DNA encoding the desired dominant-negative mutant. Examples of the expression vectors include those described in 3 below.

Introduction of a gene into various host cells can be carried out by the methods suitable for introducing a recombinant vector into various host cells described in 3 below.

The methods for selecting the transformant using, as an index, the activity of the enzyme relating to the synthesis of an intracellular sugar nucleotide, GDP-fucose or the activity of the enzyme relating to the fucose modification include the methods described in the above method.

The methods for selecting the transformant using, as an index, the sugar chain structure of a glycoprotein on the cell membrane include the method described in 1 (5) below. The methods for selecting the transformant using, as an index, the sugar chain structure of a produced glycoprotein molecule include the methods described in 5 below.

(3) Technique of Introducing a Mutation into an Enzyme

The host cell used for the production of the Protein S composition of the present invention can be prepared by introducing a mutation into a gene encoding an enzyme relating to the fucose modification, and then selecting a desired cell line in which the mutation occurred in the enzyme.

Examples of the enzymes relating to the synthesis of the intracellular sugar nucleotide, GDP-fucose include GMD and Fx. Examples of the enzymes relating to the modification of a sugar chain in which 1-position of fucose is bound to 6-position of N-acetylglucosamine in the reducing end through α-bond in a complex type N-glycoside-linked sugar chain include, in particular, α1,6-fucosyltransferase, α-L-fucosidase and the like. Examples of a protein relating to the transportation of GDP-fucose to the Golgi apparatus include, in particular, GDP-fucose transporter and the like.

The methods for introducing a mutation into the enzyme relating to the fucoase modification include: 1) a method in which a desired cell line is selected from mutants obtained by subjecting a parent cell line to mutagenesis or by spontaneous mutation using, as an index, the activity of the fucose modification; 2) a method in which a desired cell line is selected from mutants obtained by subjecting a parent cell line to mutagenesis or by spontaneous mutation using, as an index, the sugar chain structure of a produced glycoprotein molecule; and 3) a method in which a desired cell line is selected from mutants obtained by subjecting a parent cell line to mutagenesis or by spontaneous mutation using, as an index, the sugar chain structure of a glycoprotein on the cell membrane.

Mutagenesis may be carried out by any method capable of inducing a point mutation, a deletion mutation or a frameshift mutation in DNA of a cell of a parent cell line.

Suitable methods include treatment with ethyl nitrosourea, nitrosoguanidine, benzopyrene or an acridine dye and radiation treatment. Various alkylating agents and carcinogens are also useful as mutagens. A mutagen is allowed to act on a cell by the methods described in *Soshiki Baiyo no Gijutsu* (*Tissue Culture Techniques*), Third Edition (Asakura Shoten), edited by The Japanese Tissue Culture Association (1996); *Nature Genet.*, 24, 314 (2000); etc.

Examples of the mutants generated by spontaneous mutation include spontaneous mutants obtained by continuing subculture under usual cell culture conditions without any particular treatment for mutagenesis.

The methods for measuring the activity of the enzyme relating to the fucose modification include the methods described in the above 1 (a). The methods for determining the sugar chain structure of a produced glycoprotein molecule include the methods described in 5 below. The methods for determining the sugar chain structure of a glycoprotein on the cell membrane include the method described in the above 1 (5).

(4) Technique of suppressing transcription or translation of a gene encoding an enzyme The host cell used for the production of the Protein S composition of the present invention can be prepared by suppressing transcription or translation of a target gene, i.e., a gene encoding an enzyme relating to the synthesis of the intracellular sugar nucleotide, GDP-fucose or an enzyme relating to the modification of a sugar chain in which 1-position of fucose is bound to 6-position of N-acetylglucosamine in the reducing end through α-bond in a complex type N-glycoside-linked sugar chain using the antisense RNA/DNA technique [*Bioscience and Industry*, 50, 322 (1992); *Chemistry*, 46, 681 (1991); *Biotechnology*, 9, 358 (1992); *Trends in Biotechnology*, 10, 87 (1992); *Trends in Biotechnology*, 10, 152 (1992); *Cell Technology*, 16, 1463 (1997)], the triple helix technique [*Trends in Biotechnology*, 10, 132 (1992)], etc.

Examples of the enzymes relating to the synthesis of the intracellular sugar nucleotide, GDP-fucose include GMD and Fx. Examples of the enzymes relating to the modification of a sugar chain in which 1-position of fucose is bound to 6-position of N-acetylglucosamine in the reducing end through α-bond in a complex type N-glycoside-linked sugar chain include α1,6-fucosyltransferase, α-L-fucosidase and the like.

(5) Technique of Selecting a Cell Line Resistant to a Lectin which Recognizes a Sugar Chain Structure in which 1-Position of Fucose is Bound to 6-Position of N-Acetylglucosamine in the Reducing End Through α-Bond in a Complex Type N-Glycoside-Linked Sugar Chain The host cell used for the production of the Protein S composition of the present invention can be prepared by selecting a cell line resistant to a lectin which recognizes a sugar chain structure in which 1-position of fucose is bound to 6-position of N-acetylglucosamine in the reducing end through α-bond in a complex type N-glycoside-linked sugar chain.

Selection of a cell line resistant to a lectin which recognizes a sugar chain structure in which 1-position of fucose is bound to 6-position of N-acetylglucosamine in the reducing end through α-bond in a complex type N-glycoside-linked sugar chain can be carried out, for example, by the method using a lectin described in *Somatic Cell Mol. Genet.*, 12, 51 (1986), etc.

As the lectin, any lectin can be used so long as it recognizes a sugar chain structure in which 1-position of fucose is bound to 6-position of N-acetylglucosamine in the reducing end through α-bond in a complex type N-glycoside-linked sugar chain. Specific examples include lentil lectin LCA (lentil agglutinin derived from *Lens culinaris*), pea lectin PSA (pea lectin derived from *Pisum sativum*), broad bean lectin VFA (agglutinin derived from *Vicia faba*) and *Aleuria aurantia* lectin AAL (lectin derived from *Aleuria aurantia*).

Specifically, the cell line of the present invention resistant to a lectin which recognizes a sugar chain structure in which 1-position of fucose is bound to 6-position of N-acetylglucosamine in the reducing end through α-bond in a complex type N-glycoside-linked sugar chain can be selected by culturing cells in a medium containing the above lectin at a concentration of 1 µg/mL to 1 mg/mL for one day to 2 weeks, preferably one day to one week, subculturing surviving cells or picking up a colony and transferring it into a culture vessel, and subsequently continuing the culturing using the medium containing the lectin.

2. Preparation of a Transgenic Non-Human Animal or Plant or the Progenies Thereof of the Present Invention The transgenic non-human animal or plant or the progenies thereof of the present invention in which a genomic gene is modified so that the activity of an enzyme relating to the modification of a sugar chain of a Protein S molecule can be controlled can be prepared from the embryonic stem cell, fertilized egg cell, or plant callus cell of the present invention prepared in accordance with the above 1, by using a gene encoding an enzyme relating to the synthesis of an intracellular sugar nucleotide, GDP-fucose, or an enzyme relating to the modification of a sugar chain wherein 1-position of fucose is bound to 6-position of N-acetylglucosamine in the reducing end through α-bond in the complex type N-glycoside-linked sugar chain, or a protein relating to the transportation of an intracellular sugar nucleotide, GDP-fucose to the Golgi apparatus as the target, according to, for example, the following procedure.

In the case of transgenic non-human animal, the embryonic stem cell of the present invention in which the activity of an enzyme relating to the synthesis of an intracellular sugar nucleotide, GDP-fucose; an enzyme relating to the modification of a sugar chain wherein 1-position of fucose is bound to 6-position of N-acetylglucosamine in the reducing end through α-bond in the complex type N-glycoside-linked sugar chain; or a protein relating to the transportation of an intracellular sugar nucleotide, GDP-fucose to the Golgi apparatus can be controlled, can be prepared from an embryonic stem cell of a desired non-human animal, for example cattle, sheep, goat, pig, horse, mouse, rat, fowl, monkey, rabbit and the like, by using the technique described in the above 1 (Nature Biotechnology, vol. 21, 157-162 (2003), Nature Biotechnology, vol. 174, 56-461 (1999), and Glycobiology, vol. 14, 51-64 (2004)).

Specifically, a mutant clone is prepared in which a gene encoding an enzyme relating to the synthesis of an intracellular sugar nucleotide, GDP-fucose, an enzyme relating to the modification of a sugar chain wherein 1-position of fucose is bound to 6-position of N-acetylglucosamine in the reducing end through α-bond in the complex type N-glycoside-linked sugar chain, or a protein relating to the transportation of an intracellular sugar nucleotide, GDP-fucose to the Golgi apparatus, present on the chromosome, is inactivated or substituted with any sequence, by a known homologous recombination technique [for example, Nature 326, 6110, 295 (1987); Cell, 51, 3, 503 (1987); or the like]. Using the prepared embryonic stem cell (for example, that mutant clone), a chimeric individual consisting of an embryonic stem cell clone and a normal cell can be prepared by an injection chimera method into blastocyst of fertilized egg of an animal or by an aggregation chimera method. The chimeric individual is crossed with a normal individual, so that a transgenic non-human animal in which the activity of an enzyme relating to the synthesis of an intracellular sugar nucleotide, GDP-fucose, the activity of an enzyme relating to the modification of a sugar chain wherein 1-position of fucose is bound to 6-position of N-acetylglucosamine in the reducing end through α-bond in the complex type N-glycoside-linked sugar chain, or the activity of a protein relating to the transportation of an intracellular sugar nucleotide, GDP-fucose to the Golgi apparatus is decreased in the whole body cells can be obtained.

Also, a fertilized egg cell of the present invention in which the activity of an enzyme relating to the synthesis of an intracellular sugar nucleotide, GDP-fucose, the activity of an enzyme relating to the modification of a sugar chain wherein 1-position of fucose is bound to 6-position of N-acetylglucosamine in the reducing end through α-bond in the complex type N-glycoside-linked sugar chain, or the activity of a protein relating to the transportation of an intracellular sugar nucleotide, GDP-fucose to the Golgi apparatus is decreased can be prepared by applying the method similar to that in Section 1 to a fertilized egg of a non-human animal of interest such as cattle, sheep, goat, pig, horse, mouse, rat, fowl, monkey, rabbit or the like.

A transgenic non-human animal in which the activity of an enzyme relating to the synthesis of an intracellular sugar nucleotide, GDP-fucose, the activity of an enzyme relating to the modification of a sugar chain wherein 1-position of fucose is bound to 6-position of N-acetylglucosamine in the reducing end through α-bond in the complex type N-glycoside-linked sugar chain, or the activity of a protein relating to the transportation of an intracellular sugar nucleotide, GDP-fucose to the Golgi apparatus is decreased can be prepared by transplanting the prepared fertilized egg cell into the oviduct or uterus of a pseudopregnant female using the embryo transplantation method described in Manipulating Mouse Embryo, Second Edition or the like, followed by childbirth by the animal.

In a transgenic plant, the callus of the present invention in which the activity of an enzyme relating to the synthesis of an intracellular sugar nucleotide, GDP-fucose, the activity of an enzyme relating to the modification of a sugar chain wherein 1-position of fucose is bound to 6-position of N-acetylglucosamine in the reducing end through α-bond in the complex type N-glycoside-linked sugar chain, or the activity of a protein relating to the transportation of an intracellular sugar nucleotide, GDP-fucose to the Golgi apparatus is decreased can be prepared by applying the method similar to that in the above 1 to a callus or cell of the plant of interest.

A transgenic plant in which the activity of an enzyme relating to the synthesis of an intracellular sugar nucleotide, GDP-fucose, the activity of an enzyme relating to the modification of a sugar chain wherein 1-position of fucose is bound to 6-position of N-acetylglucosamine in the reducing end through α-bond in the complex type N-glycoside-linked sugar chain, or the activity of a protein relating to the transportation of an intracellular sugar nucleotide, GDP-fucose to the Golgi apparatus is decreased can be prepared by culturing the prepared callus in a medium containing auxin and cytokinin to redifferentite it in accordance with a known method [Tissue Culture, 20 (1994); Tissue Culture, 21 (1995); and Trends in Biotechnology, 15, 45 (1997)].

3. Process for Producing the Protein S Composition

The Protein S composition of the present invention can be obtained by expressing it in a host cell using the methods described in *Molecular Cloning*, Second Edition, *Current Protocols in Molecular Biology, Antibodies, A Laboratory manual*, Cold Spring Harbor Laboratory (1988) (hereinafter referred to as *Antibodies*), *Monoclonal Antibodies: Principles and Practice*, Third Edition, Acad. Press (1993) (hereinafter referred to as *Monoclonal Antibodies*), *Antibody Engineering, A Practical Approach*, IRL Press at Oxford University Press (1996) (hereinafter referred to as *Antibody Engineering*) etc., for example, in the following manner.

A full-length cDNA encoding a Protein S molecule is prepared, and a DNA fragment of appropriate length comprising a region encoding Protein S molecule is prepared.

A recombinant vector is prepared by inserting the DNA fragment or full-length DNA into a site downstream of a promoter in an appropriate expression vector.

The recombinant vector is introduced into a host cell suited for the expression vector to obtain a transformant producing the Protein S composition.

As the host cell, any yeast cell, animal cell, insect cell, plant cell, etc. can be used so long as a cell can express the desired gene.

Also useful as the host cell are cells obtained by selecting cells in which the activity of an enzyme relating to the modification of an N-glycoside-linked sugar chain bound to Protein S molecule, i.e., an enzyme relating to the fucose modification is deleted, or cells obtained by various artificial techniques described in the above 1.

The expression vectors that can be employed are those capable of autonomous replication or integration into the chromosome in the above host cells and comprising a promoter at a position appropriate for the transcription of the DNA encoding the desired Protein S molecule.

The cDNA can be prepared from a human or non-human animal tissue or cell according to the methods for preparing a cDNA described in the above 1 using, e.g., a probe or primers specific for cDNA encoding the desired Protein S molecule.

When yeast is used as the host cell, YEP13 (ATCC 37115), YEp24 (ATCC 37051), YCp50 (ATCC 37419), etc. can be used as the expression vector.

As the promoter, any promoter capable of expressing in yeast strains can be used. Suitable promoters include promoters of genes of the glycolytic pathway such as hexosekinase, PHO5 promoter, PGK promoter, GAP promoter, ADH promoter, gal 1 promoter, gal 10 promoter, heat shock protein promoter, MFα1 promoter and CUP 1 promoter.

Examples of suitable host cells are microorganisms belonging to the genera *Saccharomyces, Schizosaccharomyces, Kluyveromyces, Trichosporon, Schwanniomyces* and *Pichia*, and specifically, *Saccharomyces cerevisiae, Schizosaccharomyces pombe, Kluyveromyces lactis, Trichosporon pullulans, Schwanniomyces alluvius* and *Pichia pastoris*.

Introduction of the recombinant vector can be carried out by any method for introducing DNA into yeast, for example, electroporation [*Methods Enzymol.*, 194, 182 (1990)], the spheroplast method [*Proc. Natl. Acad. Sci. USA*, 84, 1929 (1978)], the lithium acetate method [*J. Bacteriology*, 153, 163 (1983)] and the method described in *Proc. Natl. Acad. Sci. USA*, 75, 1929 (1978).

When an animal cell is used as the host cell, pcDNAI, pcDM8 (commercially available from Funakoshi Co., Ltd.), pAGE107 [Japanese Published Unexamined Patent Application No. 22979/91; *Cytotechnology*, 3, 133 (1990)], pAS3-3 (Japanese Published Unexamined Patent Application No. 227075/90), pCDM8 [*Nature*, 329, 840 (1987)], pcDNAI/Amp (manufactured by Invitrogen Corp.), pREP4 (manufactured by Invitrogen Corp.), pAGE103 [*J. Biochemistry*, 101, 1307 (1987)], pAGE210, etc. can be used as the expression vector.

As the promoter, any promoter capable of expressing in animal cells can be used. Suitable promoters include the promoter of IE (immediate early) gene of cytomegalovirus (CMV), SV40 early promoter, the promoter of a retrovirus, metallothionein promoter, heat shock promoter, SRα promoter, etc. The enhancer of IE gene of human CMV may be used in combination with the promoter.

Examples of suitable host cells include human-derived Namalwa cells, monkey-derived COS cells, Chinese hamster-derived CHO cells, HBT5637 (Japanese Published Unexamined Patent Application No. 299/88), rat myeloma cells, mouse myeloma cells, cells derived from Syrian hamster kidney, embryonic stem cells, fertilized egg cells and the like.

Introduction of the recombinant vector can be carried out by any method for introducing DNA into animal cells, for example, electroporation [*Cytotechnology*, 3, 133 (1990)], the calcium phosphate method (Japanese Published Unexamined Patent Application No. 227075/90), lipofection [*Proc. Natl. Acad. Sci. USA*, 84, 7413 (1987)], the injection method [*Manipulating the Mouse Embryo, A Laboratory Manual*], the method using particle gun (gene gun) (Japanese Patent Nos. 2606856 and 2517813), the DEAE-dextran method [*Biomanual Series 4—Methods of Gene Transfer, Expression and Analysis* (Yodosha), edited by Takashi Yokota and Kenichi Arai (1994)] and the virus vector method [*Manipulating the Mouse Embryo, A Laboratory Manual*, Second Edition].

When an insect cell is used as the host cell, the protein can be expressed by the methods described in *Current Protocols in Molecular Biology; Baculovirus Expression Vectors, A Laboratory Manual*, W.H. Freeman and Company, New York (1992); *Bio/Technology*, 6, 47 (1988), etc.

That is, the expression vector and a baculovirus are cotransfected into insect cells to obtain a recombinant virus in the culture supernatant of the insect cells, and then insect cells are infected with the recombinant virus, whereby the Protein S composition of the present invention can be expressed.

The gene introducing vectors useful in this method include pVL1392, pVL1393, pBlueBacIII (products of Invitrogen Corp. and the like).

An example of the baculovirus is *Autographa californica* nuclear polyhedrosis virus, which is a virus infecting insects belonging to the family Barathra.

Examples of the insect cells are *Spodoptera frugiperda* ovarian cells Sf9 and Sf21 [*Current Protocols in Molecular Biology; Baculovirus Expression Vectors, A Laboratory Manual*, W.H. Freeman and Company, New York (1992)] and *Trichoplusia ni* ovarian cell High 5 (manufactured by Invitrogen Corp.).

Cotransfection of the above expression vector and the above baculovirus into insect cells for the preparation of the recombinant virus can be carried out by the calcium phosphate method (Japanese Published Unexamined Patent Application No. 227075/90), lipofection [*Proc. Natl. Acad. Sci. USA*, 84, 7413 (1987)], etc.

When a plant cell is used as the host cell, Ti plasmid, tobacco mosaic virus vector, etc. can be used as the expression vector.

As the promoter, any promoter capable of expressing in plant cells can be used. Suitable promoters include $^{35}$S promoter of cauliflower mosaic virus (CaMV), rice actin 1 promoter, etc.

Examples of suitable host cells are cells of plants such as tobacco, potato, tomato, carrot, soybean, rape, alfalfa, rice, wheat and barley.

Introduction of the recombinant vector can be carried out by any method for introducing DNA into plant cells, for example, the method using *Agrobacterium* (Japanese Published Unexamined Patent Application Nos. 140885/84 and 70080/85, WO94/00977), electroporation (Japanese Published Unexamined Patent Application No. 251887/85) and the method using particle gun (gene gun) (Japanese Patent Nos. 2606856 and 2517813).

Expression of the Protein S composition can be carried out not only by direct expression but also by secretory production, etc. according to the methods described in *Molecular Cloning*, Second Edition, etc.

When the gene is expressed in a yeast cell, an animal cell, an insect cell or a plant cell carrying an introduced gene relating to the synthesis of a sugar chain, an Protein S molecule to which a sugar or a sugar chain is added by the introduced gene can be obtained.

The Protein S composition of the present invention can be produced by culturing the transformant obtained as above in a medium, allowing the Protein S composition to produce and accumulate in the culture, and recovering them from the culture. Culturing of the transformant in a medium can be carried out by conventional methods for culturing the host cell.

For the culturing of the transformant obtained by using a eucaryote such as yeast as the host cell, any of natural media and synthetic media can be used insofar as it is a medium suitable for efficient culturing of the transformant which contains carbon sources, nitrogen sources, inorganic salts, etc. which can be assimilated by the host used. However, it is known that a commonly used yeast as a host cell for producing a recombinant protein which completely lacks γ-carboxylation activity of glutamic acid residue located at the N-terminal region of Protein S protein.

As the carbon sources, any carbon source that can be assimilated by the host can be used. Examples of suitable carbon sources include carbohydrates such as glucose, fructose, sucrose, molasses containing them, starch and starch hydrolyzate; organic acids such as acetic acid and propionic acid; and alcohols such as ethanol and propanol.

As the nitrogen sources, ammonia, ammonium salts of organic or inorganic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate, and various fermented microbial cells and digested products thereof.

Examples of the inorganic salts include potassium dihydrogenphosphate, dipotassium hydrogenphosphate, magnesium phosphate, magnesium sulfate, sodium chloride, ferrous sulfate, manganese sulfate, copper sulfate and calcium carbonate.

Culturing is usually carried out under aerobic conditions, for example, by shaking culture or submerged spinner culture under aeration. The culturing temperature is preferably 15 to 40° C., and the culturing period is usually 16 hours to 7 days. The pH is maintained at 3.0 to 9.0 during the culturing. The pH adjustment is carried out by using an organic or inorganic acid, an alkali solution, urea, calcium carbonate, ammonia, etc.

If necessary, antibiotics such as ampicillin and tetracycline may be added to the medium during the culturing.

When a microorganism transformed with a recombinant vector comprising an inducible promoter is cultured, an inducer may be added to the medium, if necessary. For example, in the case of a microorganism transformed with a recombinant vector comprising lac promoter, isopropyl-β-D-thiogalactopyranoside or the like may be added to the medium; and in the case of a microorganism transformed with a recombinant vector comprising trp promoter, indoleacrylic acid or the like may be added.

For the culturing of the transformant obtained by using an animal cell as the host cell, generally employed media such as RPMI1640 medium [*The Journal of the American Medical Association*, 199, 519 (1967)], Eagle's MEM medium [*Science*, 122, 501 (1952)], Dulbecco's modified MEM medium [*Virology*, 8, 396 (1959)], 199 medium [*Proceeding of the Society for the Biological Medicine*, 73, 1 (1950)] and Whitten's medium [*Developmental Engineering Experimentation Manual—Preparation of Transgenic Mice* (Kodansha), edited by Motoya Katsuki (1987)], media prepared by adding fetal calf serum or the like to these media, etc. can be used as the medium.

Culturing is usually carried out under conditions of pH 6 to 8 at 30 to 40° C. for 1 to 7 days in the presence of 5% $CO_2$.

If necessary, antibiotics such as kanamycin and penicillin may be added to the medium during the culturing.

For the culturing of the transformant obtained by using an insect cell as the host cell, generally employed media such as TNM-FH medium (manufactured by Pharmingen, Inc.), Sf-900 II SFM medium (manufactured by Life Technologies, Inc.), ExCell 400 and ExCell 405 (manufactured by JRH Biosciences, Inc.) and Grace's Insect Medium [*Nature*, 195, 788 (1962)] can be used as the medium. Culturing is usually carried out under conditions of pH 6 to 7 at 25 to 30° C. for 1 to 5 days.

If necessary, antibiotics such as gentamicin may be added to the medium during the culturing.

The transformant obtained by using a plant cell as the host cell may be cultured in the form of cells as such or after differentiation into plant cells or plant organs. For the culturing of such transformant, generally employed media such as Murashige-Skoog (MS) medium and White medium, media prepared by adding phytohormones such as auxin and cytokinin to these media, etc. can be used as the medium.

Culturing is usually carried out under conditions of pH 5 to 9 at 20 to 40° C. for 3 to 60 days.

If necessary, antibiotics such as kanamycin and hygromycin may be added to the medium during the culturing.

As described above, the Protein S composition of the present invention can be produced by culturing, according to a conventional culturing method, the transformant derived from an animal cell or a plant cell and carrying an expression vector into which DNA encoding Protein S molecule has been inserted, allowing the Protein S composition to produce and accumulate, and recovering the Protein S composition from the culture.

The Protein S composition may be produced intracellularly in host cells, may be secreted extracellularly in host cells or may be produced on outer membranes of host cells. A desirable production method can be adopted by changing the kind of the host cells used or the structure of Protein S molecule to be produced.

When the Protein S composition is produced in host cells or on outer membranes of host cells, it is possible to force the Protein S composition to be mainly secreted outside the host cells by applying the method of Paulson, et al. [*J. Biol. Chem.*, 264, 17619 (1989)], the method of Lowe, et al. [*Proc. Natl. Acad. Sci. USA*, 86, 8227 (1989); *Genes Develop.*, 4, 1288 (1990)], or the methods described in Japanese Published Unexamined Patent Application No. 336963/93, 823021/94, etc.

That is, it is possible to force the desired Protein S molecule to be secreted mainly outside the host cells by inserting DNA encoding Protein S molecule and DNA encoding a signal peptide suitable for the expression of Protein S molecule into an expression vector, introducing the expression vector into the host cells, and then expressing Protein S molecules by use of recombinant DNA techniques.

It is also possible to increase the production of the Protein S composition by utilizing a gene amplification system using a dihydrofolate reductase gene or the like according to the method described in Japanese Published Unexamined Patent Application No. 227075/90.

Further, the Protein S composition can be produced using an animal individual having an introduced gene (non-human transgenic animal) or a plant individual having an introduced gene (transgenic plant) constructed by redifferentiation of animal or plant cells carrying the introduced gene.

When the transformant is an animal individual or plant individual, the Protein S composition can be produced by raising or culturing the animal or plant in a usual manner, allowing the Protein S composition to produce and accumulate therein, and recovering the Protein S composition from the animal individual or plant individual.

Production of the Protein S composition using an animal individual can be carried out, for example, by producing the desired Protein S composition in an animal constructed by introducing the gene according to known methods [*American Journal of Clinical Nutrition*, 63, 639S (1996); *American Journal of Clinical Nutrition*, 63, 627S (1996); *Bio/Technology*, 9, 830 (1991)].

In the case of an animal individual, the Protein S composition can be produced, for example, by raising a non-human transgenic animal carrying the introduced DNA encoding Protein S molecule, allowing the Protein S composition to produce and accumulate in the animal, and recovering the Protein S composition from the animal. The places where the Protein S composition is formed and accumulated include milk (Japanese Published Unexamined Patent Application No. 309192/88), egg, etc. of the animal. As the promoter in this process, any promoter capable of expressing in an animal can be used. Preferred promoters include mammary gland cell-specific promoters such as a casein promoter, β casein promoter, β lactoglobulin promoter, whey acidic protein promoter and the like.

Production of the Protein S composition using a plant individual can be carried out, for example, by culturing a transgenic plant carrying the introduced DNA encoding Protein S molecule according to known methods [*Soshiki Baiyo (Tissue Culture)*, 20 (1994); *Soshiki Baiyo (Tissue Culture)*, 21 (1995); *Trends in Biotechnology*, 15, 45 (1997)], allowing the Protein S composition to produce and accumulate in the plant, and recovering the Protein S composition from the plant.

When the Protein S composition produced by the transformant into which the DNA encoding Protein S molecule is introduced is expressed in a soluble form in cells, the cells are collected by centrifugation after the completion of culturing and suspended in an aqueous buffer, followed by disruption using a sonicator, French press, Manton Gaulin homogenizer, Dynomill or the like to obtain a cell-free extract. A purified preparation of the Protein S composition can be obtained by centrifuging the cell-free extract to obtain the supernatant and then subjecting the supernatant to ordinary means for isolating and purifying enzymes, e.g., extraction with a solvent, salting-out with ammonium sulfate, etc., desalting, precipitation with an organic solvent, anion exchange chromatography using resins such as diethylaminoethyl (DEAE)-Sepharose and DIAION HPA-75 (manufactured by Mitsubishi Chemical Corporation), cation exchange chromatography using resins such as S-Sepharose FF (manufactured by Pharmacia), hydrophobic chromatography using resins such as butyl Sepharose and phenyl Sepharose, gel filtration using a molecular sieve, affinity chromatography, chromatofocusing, and electrophoresis such as isoelectric focusing, alone or in combination. Specifically, examples include the method using immobilized heparin affinity chromatography developed by Miller-Anderson in 1974 (Thromb. Res. 5, 439, 1974; *Zoku Seikagaku Jikken Koza (Sequel of Lectures on Experiments in Biochemistry)* 8, *Blood, Second volume*, edited by The Japanese Biochemical Society, pp. 569-574, Tokyo Kagaku Dojin, 1985).

When the Protein S composition is expressed as an inclusion body in cells, the cells are similarly recovered and disrupted, followed by centrifugation to recover the inclusion body of the Protein S composition as a precipitate fraction. The recovered inclusion body of the Protein S composition is solubilized with a protein-denaturing agent. The solubilized Protein S solution is diluted or dialyzed, whereby the Protein S composition is renatured to have normal conformation. Then, a purified preparation of the Protein S composition can be obtained by the same isolation and purification steps as described above.

When the Protein S composition is extracellularly secreted, the Protein S composition or its derivative can be recovered in the culture supernatant. That is, the culture is treated by the same means as above, e.g., centrifugation, to obtain the culture supernatant. A purified preparation of the Protein S composition can be obtained from the culture supernatant by using the same isolation and purification methods as described above.

when a host cell already has an ability to express Protein S molecules, the Protein S composition of the present invention can be produced by preparing a cell having the ability to express Protein S molecules in a manner described in the above 1 and then culturing the cell, followed by purifying the desired Protein S composition from the culture.

4. Evaluation of Activity of Protein S Composition

Biological activities of a purified Protein S composition, including APC cofactor activity or binding activity to RAGE, can be measured using a variety of already known methods. Specifically, in vivo tests using pathological animal models of APC cofactor activity, prothrombinase (tenase) inhibitory activity, binding activity to RAGE or cytokine inhibitory activity of Protein S, sepsis, acute lung injury, infertility or thrombosis may be carried out in accordance with known methods described in literature [*JBC* 256, 11128 (1981), *JBC* 270, 27852 (1995), *JBC* 272, 20678 (1997), *JBC* 261, 12022 (1986), *Thromb Haemost* 85, 761 (2001), *JBC* 268, 2872 (1993), *PNAS* 91, 2728 (1994), *Blood* 86, 1062 (1995), *Thromb Haemost* 80, 930 (1998), *Thromb Haemost* 82, 80 (1999), *Eur J Immunol* 38, 809 (2008), *Arthritis Rheumatism* 54, 3898 (2006), *Critical care* 11, R122 (2007), *Blood* 86, 2642 (1995), *J Clin Invest* 95, 1987 (1995), *J Immunol* 165, 2950 (2000), *Seminars in Thrombosis and Hemostasis* 27, 99 (2001), and *Thromb Haemost* 90, 227 (2003)], and the like. Further, a half-life of the Protein S composition in blood can be measured using the purified Protein S composition, by carrying out in vivo tests in accordance with already known methods (*Arterioscler Thromb Vasc Biol* 25, 2209 (2005)). Hereinafter, specific examples thereof will be given.

(1) Measurement of Binding Activity to RAGE

The purified Protein S composition as a test substance, and commercially available Protein S having a known concentration and the specific activity as a standard are each serially diluted in Dulbecco's phosphate buffer (pH 7.0) (*Journal of Experimental Medicine* 98, 167 (1954), hereinafter referred to as "PBS") containing 1% (v/v) bovine serum albumin (hereinafter referred to often as "BSA"). Further, a commercially available recombinant soluble receptor for advanced glycation end products (RAGE)-human IgG1 Fc chimeric protein (manufactured by R&D Systems) is dissolved at a concentration of 100 ng/mL in PBS, the obtained solution is dispensed into a flat-bottomed 96-well ELISA plate at a volume of 100 µL/well and allowed to stand at room temperature for 4 hours to prepare a plate in which RAGE is immobilized. The plate is blocked with PBS containing 1% (v/v) bovine serum albumin (hereinafter referred to as "1% BSA-PBS"), and the serially diluted test substance and the standard are dispensed thereto at a volume of 100 µL/well, followed by incubation at room temperature for 1 hour. Each well is washed several times with PBS containing 0.01% (v/v) Tween20 (hereinafter referred to as "0.01% Tween-PBS") to remove RAGE-Fc which is not bound to the plate, and Protein S dissolved in 1% BSA-PBS is dispensed thereto at a volume of 100 µL/well. After incubation at room temperature for 1 hour, each well is washed several times with 0.01% Tween-PBS to remove Protein S which is not bound to the plate, and a commercially available HRP-labeled anti-Protein S antibody (manufactured by DAKO) dissolved in 1% BSA-PBS is dispensed thereto at a volume of 100 µL/well. After incubation at room temperature for 1 hour, each well is washed several times with 0.01% Tween-PBS to remove the anti-Protein S antibody which is not bound to the plate, and 100 µL/well of a 3,3',5,5'-tetramethylbenzidine (TMB) liquid substrate (manufactured by Sigma) is added to the plate, followed by color development at room temperature for several minutes. At the time point where appropriate color development is obtained, 0.5N $H_2SO_4$ is added to stop the reaction. Thereafter, the absorbance at 450 nm in the reaction solution is measured, and the absorbance of the reaction solution with the addition of the test substance or standard of each dilution step is subtracted from the absorbance of the control reaction solution with no addition of the test substance Protein S. The semi-logarithmic plot is made by applying the obtained value as an amount of Protein S bound to RAGE to the ordinate, and applying a dilution ratio of the test substance or standard to the abscissa. From the plotted measurement values, the relationship between the amount of the RAGE-bound Protein S and the dilution ratio is subjected to straight-line approximation. Through the comparison between approximate expressions obtained by measurement of the test substance and the standard, a magnification ratio of the test substance to the standard sample can be calculated, and the titer can be determined. Further, as a means to measure the binding affinity between Protein S and RAGE, surface plasmon resonance (hereinafter referred to simply as "SPR") using Biacore T100 (Biacore) or the like may also be used in accordance with the method described in literature [*Eur J Immunol* 38, 809 (2008)] or the like.

(2) Measurement of Inflammatory Cytokine-Inhibitory Activity

The inflammatory cytokine-inhibitory activity of the purified Protein S composition can be calculated by measuring an inhibitory activity of Protein S against the secretion of inflammatory cytokines from lymphocytes or vascular endothelial cells, in accordance with the method of Pullerits et al. (*Arthritis and Rheumatism.* 54, 3898 (2006)) or the method of Treutiger et al. (*J Internal Medicine* 254, 375 (2003)). Specifically, the purified Protein S composition as a test substance, and human plasma-derived Protein S having a known concentration as a standard are each serially diluted with 1% BSA-PBS, or the like. Then, the serial dilutions of Protein S are added to each well for human-derived lymphocytes or vascular endothelial cells cultured in a 96-well tissue culture plate, and subsequently an inflammation-inducing substance, for example, lipopolysaccharide (hereinafter referred to as "LPS") or HMGB-1 protein, S100 peptide, or the like is added thereto. The inflammatory cytokine-inhibitory activity of Protein S can be measured by such a manner that the culture supernatant is collected after culturing for a given period of time and the concentrations of inflammatory cytokines contained in the culture supernatant, for example interleukin 6, interleukin 8, tumor necrosis factor α (TNFα) and the like, are measured by using a commercially available ELISA kit or the like.

(3) In Vivo Test Using Animal Model for Sepsis

The anticoagulant effect and anti-inflammatory effect of the purified Protein S composition can be analyzed by investigating changes of coagulation system parameters or an extension of blood coagulation time, concentrations of inflammatory cytokines in blood, and the like, in an in vivo test using an animal model for hypercoagulation or for sepsis. Examples of the animal model for hypercoagulation include a model in which disseminated intravascular coagulation (DIC) is induced by continuous intravenous administration of 15 mg/kg of tissue thromboplastin to a rabbit over 5 hours, and the like. In this system, a test substance Protein S is continuously intravenously administered, for example, until completion of administration from 15 minutes before the administration of tissue thromboplastin. In addition, through time-course collection of blood before and after DIC induction, coagulation system parameters (platelet counts, fibrinogen quantity, and APTT), fibrinolytic system parameters (fibrin degradation products (FDP), and PAI-1 activity) and the like can be measured. When the administration of tissue thromboplastin is complete, auricular veins were needled to measure the bleeding time, and when the experiment is complete, the kidney is extracted to observe the deposition of fibrin into the glomerulus. As theanimal model for sepsis, exemplified is a peritonitis model by intraperitoneal administration of an endotoxin such as LPS, a model in which peritonitis is induced by cecum perforation, or the like. In this system, the test substance Protein S is intravenously administered continuously, for example, until 60 minutes after administration from 60 minutes before the administration of LPS. For example, when a mouse is used as an animal model, a dose of the Protein S composition may be in the range of 1 μg/animal to 100 μg/animal. For example, through the blood collection from the postorbital region or the like, concentrations of inflammatory cytokines or concentrations of various inflammatory markers in peripheral blood of each mouse can be measured twice a week. In addition, through the collection of a tissue, such as liver or kidney, from a mouse individual after the test was complete, inhibitory effects of inflammation, coagulation or organ failure by administration of the test substance can be analyzed.

(4) Measurement of Blood Half-Life of Protein S Using Animal Model

It is known that Protein S is present at an almost constant concentration of 25 to 30 μg/mL (300 to 350 nM in terms of the molar concentration) in healthy human plasma. This plasma Protein S is categorized into two types depending on existing forms thereof: C4BP-bound Protein S and free Protein S. C4BP is a complement inhibitory factor, which is present at a concentration of about 150 μg/mL (260 nM in terms of molar concentration) in healthy human plasma. Protein S binds with a high affinity ($K_D$ value: 0.1 to 0.6 nM) to the β chain of C4BP. Based on this fact, it is said that all of plasma C4BP are bound to Protein S (Biochemistry 36, 3745 (1997); and *Arch Pathol Lab Med* 126, 1349 (2002)). Therefore, the plasma concentration of free Protein S corresponds to the difference between a concentration of total Protein S and a concentration of C4BP-bound form, and it is said to be about 10 μg/mL (130 nM in terms of molar concentration) (*PNAS* 78, 2512 (1981), *Blood* 79, 3203 (1992)).

The blood half-life using purified recombinant Protein S composition or the like can be measured using an animal model such as rats. Rats are given a test substance or a test substance-free placebo prepared in 0.25% rat serum albumin (PBS containing 0.25% rat serum albumin) in a single dose by intravenous injection using a carotid cannula or subcutaneous injection or the like. In this case, a dose of the Protein S composition/administration may be for example in the range of 1 μg/kg to 50 mg/kg. At a certain point after administration, 300 μL of blood is collected, and a concentration of the test substance in rat blood is measured by ELISA which is capable of specifically detecting and quantifying human Protein S. Based on the obtained data, pharmacokinetic parameters of each rat are measured using nonlinear regression analysis PCNONLIN (*Statistical Consultants*, 1992). In addition, a clearance test of the Protein S composition may be evaluated using an animal model such as rodent other than rats, for example mice, or primate relatively closer to human than rats, for example cynomolgus monkey or the like.

5. Analysis of Sugar Chains in the Protein S Composition

The sugar chain structure of the Protein S compositions expressed in various cells can be analyzed according to general methods of analysis of the sugar chain structure of glycoprotein compositions. For example, a sugar chain bound to a Protein S molecule consists of neutral sugars such as galactose, mannose and fucose, amino sugars such as N-acetylglucosamine, and acidic sugars such as sialic acid, and can be analyzed by techniques such as sugar composition analysis and sugar chain structure analysis using two-dimensional sugar chain mapping.

(1) Analysis of Neutral Sugar and Amino Sugar Compositions

The sugar chain composition of a Protein S composition can be analyzed by carrying out acid hydrolysis of sugar chains with trifluoroacetic acid or the like to release neutral sugars or amino sugars and analyzing the composition ratio.

Specifically, the analysis can be carried out by a method using a carbohydrate analysis system manufactured by Dionex. BioLC is a system for analyzing the sugar composition by HPAEC-PAD (high performance anion-exchange chromatography-pulsed amperometric detection) [*J. Liq. Chromatogr.*, 6, 1577 (1983)].

The composition ratio can also be analyzed by the fluorescence labeling method using 2-aminopyridine. Specifically, the composition ratio can be calculated by fluorescence labeling an acid-hydrolyzed sample by 2-aminopyridylation according to a known method [*Agric. Biol. Chem.*, 55(1), 283 (1991)] and then carrying out the HPLC analysis.

(2) Analysis of Sugar Chain Structure

The sugar chain structure of a Protein S composition can be analyzed by two-dimensional sugar chain mapping [*Anal. Biochem.*, 171, 73 (1988); *Seibutsukagaku Jikkenho* (*Biochemical Experimentation Methods*) 23—*Totanpakushitsu Tosa Kenkyuho* (*Methods of Studies on Glycoprotein Sugar Chains*), Gakkai Shuppan Center, edited by Reiko Takahashi (1989)]. The two-dimensional sugar chain mapping is a method of deducing a sugar chain structure, for example, by plotting the retention time or elution position of a sugar chain by reversed phase chromatography as the X axis and the retention time or elution position of the sugar chain by normal phase chromatography as the Y axis, respectively, and comparing them with the results on known sugar chains.

Specifically, a sugar chain is released from a Protein S composition by hydrazinolysis of the Protein S composition and subjected to fluorescence labeling with 2-aminopyridine (hereinafter referred to as PA) [*J. Biochem.*, 95, 197 (1984)]. After being separated from an excess PA-treating reagent by gel filtration, the sugar chain is subjected to reversed phase chromatography. Then, each fractionated peak of the sugar chain is subjected to normal phase chromatography. The sugar chain structure can be deduced by plotting the obtained results on a two-dimensional sugar chain map and comparing them with the spots of a sugar chain standard (manufactured by Takara Shuzo Co., Ltd.) or those in the literature [*Anal. Biochem.*, 171, 73 (1988)].

The structure deduced by the two-dimensional sugar chain mapping can be confirmed by carrying out mass spectrometry, e.g., MALDI-TOF-MS, of each sugar chain.

6. Immunoassay for Determining the Sugar Chain Structure of a Protein S Molecule A Protein S composition comprises a Protein S molecules having different sugar chain structures binding to Protein S. The Protein S composition of the present invention, in which the ratio of a sugar chain in which fucose is not bound to the N-acetylglucosamine in the reducing end, such a Protein S composition can be determined using the method for analyzing the sugar chain structure of a Protein S composition described in the above 5. Further, it can also be determined by immunoassays using lectins.

Determination of the sugar chain structure of a Protein S composition by immunoassays using lectins can be made according to the immunoassays such as Western staining, RIA (radioimmunoassay), VIA (viroimmunoassay), EIA (enzymeimmunoassay), FIA (fluoroimmunoassay) and MIA (metalloimmunoassay) described in the literature [*Monoclonal Antibodies: Principles and Applications*, Wiley-Liss, Inc. (1995); *Enzyme Immunoassay*, 3rd Ed., Igaku Shoin (1987); *Enzyme Antibody Technique*, Revised Edition, Gakusai Kikaku (1985); etc.], for example, in the following manner.

A lectin recognizing the sugar chain structure of Protein S molecules constituting the Protein S composition is labeled, and the labeled lectin is subjected to reaction with a sample Protein S composition, followed by measurement of the amount of a complex of the labeled lectin with Protein S molecule.

Examples of lectins useful for determining the sugar chain structure of a Protein S molecule include WGA (wheat-germ agglutinin derived from *T. vulgaris*), ConA (concanavalin A derived from *C. ensiformis*), RIC (toxin derived from *R. communis*), L-PHA (leukoagglutinin derived from *P. vulgaris*), LCA (lentil agglutinin derived from *L. culinaris*), PSA (pea lectin derived from *P. sativum*), AAL (*Aleuria aurantia* lectin), ACL (*Amaranthus caudatus* lectin), BPL (*Bauhinia purpurea* lectin), DSL (*Datura stramonium* lectin), DBA (*Dolichos biflorus* agglutinin), EBL (Elderberry balk lectin), ECL (*Erythrina cristagalli* lectin), EEL (*Euonymus europaeus* lectin), GNL (*Galanthus nivalis* lectin), GSL (*Griffonia simplicifolia* lectin), HPA (*Helix pomatia* agglutinin), HHL (*Hippeastrum* hybrid lectin), Jacalin, LTL (*Lotus tetragonolobus* lectin), LEL (*Lycopersicon esculentum* lectin), MAL (*Maackia amurensis* lectin), MPL (*Maclura pomifera* lectin), NPL (*Narcissus pseudonarcissus* lectin), PNA (peanut agglutinin), E-PHA (*Phaseolus vulgaris* erythroagglutinin), PTL (*Psophocarpus tetragonolobus* lectin), RCA (*Ricinus communis* agglutinin), STL (*Solanum tuberosum* lectin), SJA (*Sophora japonica* agglutinin), SBA (soybean agglutinin), UEA (*Ulex europaeus* agglutinin), VVL (*Vicia villosa* lectin) and WFA (*Wisteria floribunda* agglutinin).

It is preferred to use lectins specifically recognizing a sugar chain structure wherein fucose is bound to the N-acetylglucosamine in the reducing end in complex type N-glycoside-linked sugar chains. Examples of such lectins include lentil lectin LCA (lentil agglutinin derived from *Lens culinaris*), pea lectin PSA (pea lectin derived from *Pisum sativum*), broad bean lectin VFA (agglutinin derived from *Vicia faba*) and *Aleuria aurantia* lectin AAL (lectin derived from *Aleuria aurantia*).

7. Use of the Protein S Composition of the Present Invention

Since the Protein S composition of the present invention exhibits a higher affinity for the receptor for advanced glycation end products (RAGE) than Protein S in which fucose is bound to N-acetylglucosamine in the reducing end of a complex type N-glycoside-linked sugar chain, such as conventionally known human plasma-derived or recombinant Protein S, it is expected to have high therapeutic effects on inflammatory diseases, and thromboses associated with Protein S deficiency or defect. Further, based on the fact that dose of administration, and frequency of administration can be decreased, adverse side effects such as blood pressure elevation in the treated patients, and the production of anti-Protein S antibodies can also be alleviated in conjunction with a reduction of physical and economic burden on patients or in clinical practice.

A variety of diseases for which the Protein S composition can be used as a therapeutic agent include diseases associated with the lowering of blood Protein S concentration, such as inflammatory diseases and hypercoagulation diseases. Therefore, the Protein S composition of the present invention is applicable to any disease, so long as it is an inflammatory disease or hypercoagulation disease presenting with decrease of Protein S concentration.

The disease associated with decrease of Protein S concentration in blood may include Protein S deficiency, specifically congenital Protein S deficiency, acquired Protein S deficiency and the like.

Congenital Protein S deficiency, also called congenital Protein S defect, is known as a human hereditary disease, and presents with venous thromboembolism (VTE). VTE includes two different diseases, deep vein thrombosis (DVT) and pulmonary embolism (PE).

Example of the disease associated with acquired Protein S deficiency may include abortus habitualis (infertility). Further, acquired Protein S deficiency is known to caused by various diseases such as hepatic diseases, nephrotic syndrome, HIV infections, disseminated intravascular coagulation (DIC), sepsis, acute lung injury, and rheumatoid arthritis, medications such as L-asparaginase preparations, warfarin preparations, and oral contraceptives, lowering of plasma Protein S levels during mid to late pregnancy, and the like (*Br J Opthalmol* 81, 810 (1997), *Thromb Haemost* 93, 853 (2005), *Journal of Thrombosis and Haemostasis* 12, 235 (2001)). The Protein S composition of the present invention can be used for these acquired Protein S deficiencies.

In addition, hypercoagulation diseases relating to Protein S in blood may include systemic inflammatory response syndrome (SIRS), thromboses occurring due to other pathological conditions, VTE including DVT and PE, as described above, and the like.

In the present invention, even though applications of the Protein S composition may include inflammatory diseases and blood coagulation diseases associated with Protein S deficiency as described above, the Protein S composition may also be used for acute thromboses during or immediately after surgical operation or pregnancy or childbirth, or the like of patients with Protein S deficiency, or may also be prophylactically used for the inhibition of thromboses through administration of Protein S prior to the surgery.

A pharmaceutical composition comprising the Protein S composition of the present invention may be administered alone as a therapeutic agent. However, it is preferably mixed with one or more pharmaceutically acceptable carriers and provided as a pharmaceutical preparation produced by an arbitrary method well known in the technical field of pharmaceutics.

It is desirable to administer the pharmaceutical composition by the route that is most effective for the treatment. Suitable administration routes include oral administration and parenteral administration such as intraoral administration, intratracheal administration, intrarectal administration, subcutaneous administration, intramuscular administration and intravenous administration. In the case of a Protein S preparation, intravenous administration is preferable.

The pharmaceutical preparation may be in the form of spray, capsules, tablets, granules, syrup, emulsion, suppository, injection, ointment, tape, and the like.

The pharmaceutical preparations suitable for oral administration include emulsions, syrups, capsules, tablets, powders and granules.

Liquid preparations such as emulsions and syrups can be prepared using, as additives, water, sugars (e.g., sucrose, sorbitol and fructose), glycols (e.g., polyethylene glycol and propylene glycol), oils (e.g., sesame oil, olive oil and soybean oil), antiseptics (e.g., p-hydroxybenzoates), flavors (e.g., strawberry flavor and peppermint), and the like.

Capsules, tablets, powders, granules, etc. can be prepared using, as additives, excipients (e.g., lactose, glucose, sucrose and mannitol), disintegrators (e.g., starch and sodium alginate), lubricants (e.g., magnesium stearate and talc), binders (e.g., polyvinyl alcohol, hydroxypropyl cellulose and gelatin), surfactants (e.g., fatty acid esters), plasticizers (e.g., glycerin), and the like.

The pharmaceutical preparations suitable for parenteral administration include injections, suppositories and sprays.

Injections can be prepared using carriers comprising a salt solution, a glucose solution, or a mixture thereof, etc. It is also possible to prepare powder injections by freeze-drying the Protein S composition according to a conventional method and adding sodium chloride thereto.

Suppositories can be prepared using carriers such as cacao butter, hydrogenated fat and carboxylic acid.

The Protein S composition may be administered as such in the form of spray, but sprays may be prepared using carriers which do not stimulate the oral or airway mucous membrane of a recipient and which can disperse the Protein S composition as fine particles to facilitate absorption thereof.

Suitable carriers include lactose and glycerin. It is also possible to prepare aerosols, dry powders, etc. according to the properties of the Protein S composition and the carriers used. In preparing these parenteral preparations, the above-mentioned additives for the oral preparations may also be added.

The dose and administration frequency will vary depending on the desired therapeutic effect, the administration route, the period of treatment, the patient's age and body weight, etc. However, an appropriate dose of the active ingredient for an adult person is generally 5 µg/kg to 5 mg/kg per day. Furthermore a method of analyzing physiological activity of Protein S such as the binding activity of the Protein S composition to RAGE includes in vitro examination such as analysis of APC cofactor activity, prothrobinase (tenase) inhibitory activity, binding activity of Protein S to RAGE, cytokines inhibitory activity, and in vivo examination using animal models for sepsis or thrombosis, and the like.

Analysis of APC cofactor activity, prothrombinase (tenase) inhibitory activity, binding activity to RAGE or cytokine inhibitory activity of Protein S, and in vivo examination using animal models for sepsis, acute lung injury, infertility or thrombosis may be carried out in accordance with known methods described in literature [*JBC* 256, 11128 (1981), *JBC* 270, 27852 (1995), *JBC* 272, 20678 (1997), *JBC* 261, 12022 (1986), *Thromb Haemost* 85, 761 (2001), *JBC* 268, 2872 (1993), *PNAS* 91, 2728 (1994), *Blood* 86, 1062 (1995), *Thromb Haemost* 80, 930 (1998), *Thromb Haemost* 82, 80 (1999), *Eur J Immunol* 38, 809 (2008), *Arthritis Rheumatism* 54, 3898 (2006), *Critical care* 11, R122 (2007), *Blood* 86, 2642 (1995), *J Clin Invest* 95, 1987 (1995), *J Immunol* 165, 2950 (2000), *Seminars in Thrombosis and Hemostasis* 27, 99 (2001), and *Thromb Haemost* 90, 227 (2003)], and the like.

The present invention is described below based on Examples; however, the present invention is not limited thereto.

EXAMPLES

Example 1

Analysis of Sugar Chain Structures of Human Plasma-Derived Protein S (Native Protein S)

Using Protein S (manufactured by Calbiochem) purified and isolated from human plasma as a native Protein 5, neutral sugar and amino sugar composition analysis and sialic acid analysis, and profiling analysis of N-glycoside-linked sugar chains were carried out. The neutral sugar and amino sugar composition analysis was carried out in accordance with the method of Shinkawa et al. (*Journal of Biological Chemistry* 278, 3466 (2003)). The sialic acid analysis was quantified by fluorescent labeling of sialic acid with 1,2-diamino-4,5-methylenedioxybenzene (DMB) using a sialic acid fluorescence labeling reagent kit (manufactured by Takara Bio), followed by HPLC analysis using a reverse-phase column (PALPAK Type R; manufactured by Takara Bio). The profiling analysis of N-glycoside-linked sugar chain was carried out using matrix-assisted laser ionization time of flight mass spectrometry (MALDI-TOF MS) in accordance with the method of Kanda et al. (*Glycobiology* 17, 104 (2007)).

According to the results of the neutral sugar and amino sugar composition analysis and the sialic acid analysis, composition ratios of individual monosaccharides, calculated based on a composition ratio of mannose=3.00, were 0.26 for fucose, 4.53 for N-acetylglucosamine (GlcNAc), 2.80 for galactose, and 2.11 for sialic acid, respectively. Further, the profiling analysis of N-glycoside-linked sugar chains found that all of the detected sugar chains were complex type sugar chains, a main complex type sugar chain is a biantennary branched sugar chain (complex biantennary oligosaccharide) having sialic acid in the non-reducing end thereof, and also the ratio of complex type sugar chains in which fucose was added to GlcNAc in the reducing end of the sugar chain were about more than 20% of the total complex type sugar chains. Further, according to the sugar chain analysis of respective production lots of commercially available serum-derived Protein S, Protein S in which fucose was added at a ratio of 20% or more was confirmed in any lot, and Protein S in which fucose was added at a higher ratio was confirmed in some lots.

Next, in order to analyze the binding mode of fucose added to the sugar chain of the human plasma-derived Protein S, the binding between core α1,6-fucose-specific lectin, *Lens culinaris* agglutinin (LCA) lectin and Protein S was analyzed by surface plasmon resonance. Using an amine coupling kit (manufactured by Biacore), human plasma-derived Protein S (manufactured by Calbiochem) and human plasma-derived antithrombin III (manufactured by Calbiochem) were respectively immobilized on flow cells of a CM5 sensor chip (manufactured by Biacore). The human plasma-derived antithrombin III is a glycoprotein having four asparagine-linked sugar chains, but these sugar chains are known not to have core α1,6-fucose (WO2005/035563). An immobilized amount of the ligand protein on the respective flow cells was set to the range of 2000 to 3000 resonance units (hereinafter referred to as "RU"). Then, LCA lectin (manufactured by Vector Laboratories) diluted to given concentrations (50000, 25000, 12500, 6250, 3125, and 1562 ng/mL) using HBS-EP+buffer (manufactured by Biacore), as an analyte, was allow to run and bind to the ligand-immobilized flow cells at a temperature of 25° C., a flow rate of 5 μL/min, association time of 140 seconds, and dissociation time of 240 seconds. Regeneration of the chip was carried out by a flow of an aqueous glycine solution (pH 1.5) (manufactured by Biacore) for 60 seconds.

As a result, LCA lectin exhibited no binding property to human plasma-derived antithrombin III, whereas it bound to human plasma-derived Protein S (FIG. 1). From these results, it was demonstrated that human plasma-derived Protein S has core α1,6-fucose in the reducing end side of the asparagine-linked sugar chain.

Example 2

Expression of Recombinant Human Protein S by α1,6-Fucosyltransferase (FUT8) Gene Double Knockout Cell An α1,6-fucosyltransferase (hereinafter referred to as "FUT8") gene double knockout cell line producing recombinant human Protein S was constructed in accordance with the following procedure.

1. Polymerase Chain Reaction (PCR)

For the gene sequence (UniGene: Hs. 64016 SEQ ID NO:1) of human Protein S, two primers (SEQ ID NO:3 and SEQ ID NO:4), each of which contains recognition sequences of two restriction enzymes BsiWI or BamHI at the 5'-end, were prepared, followed by PCR. Then, 20 μL of the reaction solution [KOD plus polymerase (manufactured by Toyobo), KOD plus buffer, 0.2mM dNTP mixture, 2.5 mM MgSO$_4$, 0.5 μM two primers (SEQ ID NO:3 and SEQ ID NO:4)] containing human liver-derived cDNA (manufactured by Invitrogen) as a template was prepared, and PCR was carried out under the following conditions: heating at 94° C. for 2 minutes, and then 35 cycles each consisting of reaction at 94° C. for 15 seconds, reaction at 64° C. for 30 seconds, and reaction at 68° C. for 2 minutes. After PCR was complete, the reaction solution was subjected to 1.5% (w/v) agarose gel electrophoresis to confirm a 2.1-kbp DNA fragment containing the human Protein S gene, and the fragment was then purified using a QIAquick Gel Extraction Kit (manufactured by Qiagen).

2. Construction of Plasmid pCR4-PS

Figure 2:
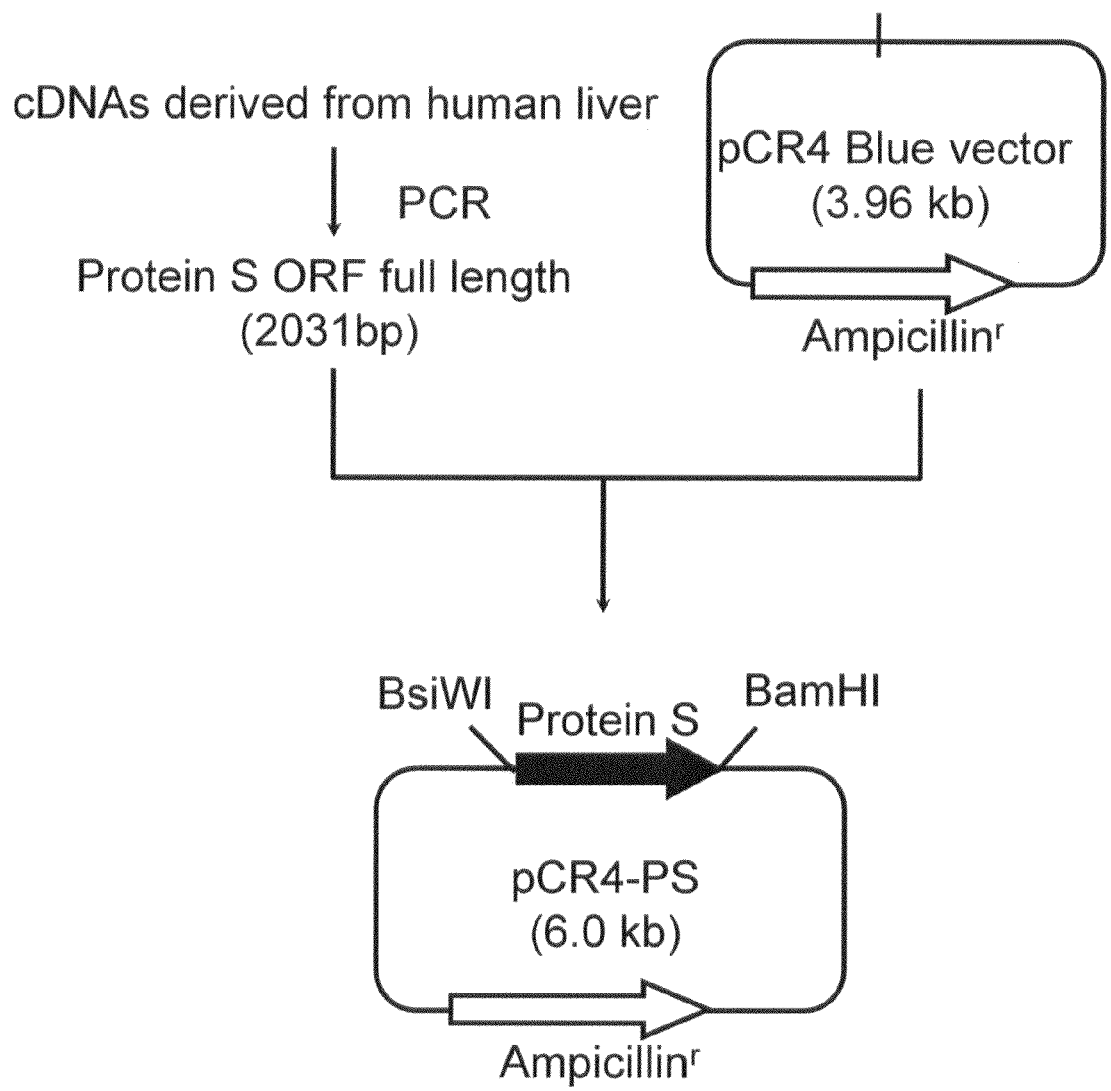
FIG. 2 shows a construction flow of a vector pCR4-PS comprising a gene of human Protein S.

The purified human Protein S cDNA fragment prepared in the above section 1 was cloned into *E. coli* using a Zero Blunt TOPO® PCR cloning kit (manufactured by Invitrogen), thereby obtaining transformed *E. coli*. A plasmid DNA was prepared from the transformant using a QIAprep®Spin Miniprep Kit (manufactured by Qiagen), and the nucleotide sequence thereof was analyzed using a BigDye Terminator Cycle Sequencing FS Ready Reaction Kit (manufactured by Applied Biosystems) and a DNA sequencer ABI PRISM 377 (manufactured by Applied Biosystems). A plasmid clone containing the human Protein S cDNA sequence was designated as pCR4-PS (FIG. 2).

3. Construction of Plasmid pKAN-PS

Figure 3:
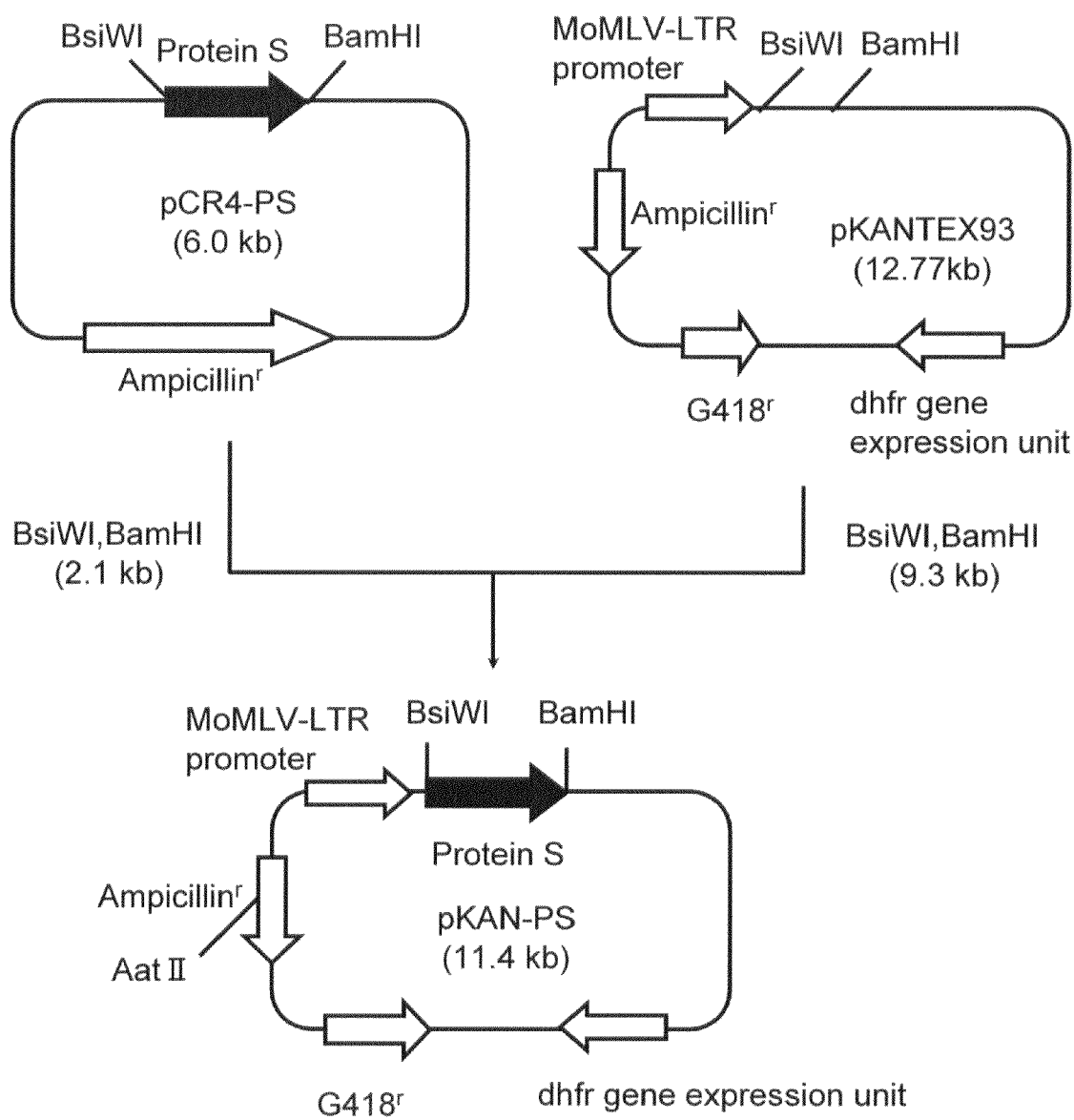
FIG. 3 shows a construction flow of a human Protein S expression vector pKAN-PS.

First, 3 μg of pCR4-PS constructed in the above section 2 was dissolved in 17.5 μL of water. To the solution, 10 units of BsiWI (manufactured by New England Biolabs) and 2 μL of NEBuffer 3 were added to prepare 20 μL of a reaction solution, followed by digestion at 55° C. for 16 hours. In addition, 10 units of BamHI (manufactured by New New England Biolabs) were added thereto to prepare 20 μL of a reaction solution, followed by digestion at 37° C. for 16 hours. Next, 3 μg of a plasmid pKANTEX93 (WO1997/10354) was dissolved in 17.5 μL of water, and BsiWI (manufactured by New England Biolabs) and 2 μL of NEBuffer 3 were added thereto to prepare 20 μL of a reaction solution, followed by digestion at 55° C. for 16 hours. In addition, 10 units of BamHI (manufactured by New England Biolabs) were added thereto to prepare 20 μL of a reaction solution, followed by digestion at 37° C. for 16 hours. The thus obtained pCR4-PS fragment (BsiWI-BamHI) and pKANTEX93 fragment (BsiWI-BamHI) were subjected to 1.5% (w/v) agarose gel electrophoresis, and about 2.1-kbp and 9.3-kbp DNA fragments were recovered and purified using a QIAquick Gel Extraction Kit (manufactured by Qiagen). Thereafter, the purified pCR4-PS fragment (BsiWI-BamHI) and the purified pKANTEX93 fragment (BsiWI-BamHI) were ligated using a Ligation High (manufactured by Toyobo). *E. coli* DH5a (manufactured by Toyo Boseki) was transformed with the obtained recombinant plasmid DNA. A plasmid DNA was prepared from the transformant, and the nucleotide sequence thereof was analyzed using a BigDye Terminator Cycle Sequencing FS Ready Reaction Kit (manufactured by Applied Biosystems) and a DNA sequencer ABI PRISM 377 (manufactured by Applied Biosystems). As a result, a plasmid pKAN-PS containing the human Protein S gene sequence (SEQ ID NO:1) was obtained (FIG. 3).

4. Introduction of Human Protein S-Expressing Plasmid into CHO/DG44 Cell Line where FUT8 Gene on the Genome was Double Knocked Out Plasmid pKAN-PS constructed in Section 3 was gene-introduced into α1,6-fucosyltransferase (FUT8) gene double knockout cell lines CHO/DG44 (WO2002/31140) and CHO/DG44 (*Proc. Natl. Acad. Sci. USA,* 77, 4216 (1980)). The introduction was carried out by electroporation in accordance with the method described in the literature [*Cytotechnology,* 3, 133 (1990)]. The plasmid was linearized by preparing 600 μL of a reaction solution containing 100 μg of plasmid pKAN-PS, 60 μL of NEBuffer 3 (manufactured by New England Biolabs), and 120 units of a restriction enzyme MluI (manufactured by New England Biolabs), followed by digestion at 37° C. for 5 hours. After the reaction was completed, the linearized plasmid was purified and recovered from the reaction solution by phenol/chloroform extraction and ethanol precipitation. Next, the FUT8 gene double knockout CHO/DG44 cells were suspended at a cell density of $8 \times 10^7$ cells/mL in K-PBS buffer (137 mM KCl, 2.7 mM NaCl, 8.1 mM Na$_2$HPO$_4$, 1.5 mM KH$_2$PO$_4$, and 4.0 mM MgCl$_2$). Into a Gene Pulser Cuvette (interelectrode distance: 2 mm) (manufactured by BIO-RAD), 200 μL ($1.6 \times 10^6$ cells) of the cell suspension and 9 μg of the linearized plasmid were mixed, and a total volume of the cell-DNA mixed solution was transferred, and was subjected to gene introduction using an electroporation device GenePulser (manufactured by BIO-RAD) at a pulse voltage of 350 V and an electric capacity of 250 μF. The cell suspension was suspended in 120 mL of IMDM medium (manufactured by Life Technologies) supplemented with fetal bovine serum (manufactured by Life Technologies) at a final concentration of 10% and 50 μg/mL of gentamicin (manufactured by Nacalai Tesque), and seeded at 100 μL/well on an adherent cell culture 96-well plate (manufactured by Greiner) in triplicate. Culturing was carried out at 5% CO$_2$ and 37° C.

5. Obtaining of 500 nM Methotrexate (MTX)-Resistant Cell Line

After the pKAN-PS-introduced cells obtained in the above section 4 were cultured for 6 days, the culture supernatant was discarded and 100 μL/well of IMDM medium supplemented with dialyzed fetal bovine serum at a final concentration of 10%, 50 μg/mL of gentamicin and 50 nM methotrexate (manufactured by Sigma, hereinafter referred to as "MTX") was added thereto. The cells were cultured for 9 days with medium exchange at 3- to 4-day intervals. Thereafter, the cells were cultured for 18 days in IMDM medium supplemented with 10% dialyzed fetal bovine serum at a final concentration of 10%, 50 μg/mL of gentamicin and 200 nM of MTX with medium exchange at 3- to 4-day intervals. The finally formed colonies were scale-up cultured in a 24-well plate (manufactured by Sigma). In addition, the cells were cultured for about 3 weeks in IMDM medium supplemented with dialyzed fetal bovine serum at a final concentration of 10%, 50 μg/mL gentamicin and 500 nM of MTX with medium exchange at 3- to 4-day intervals and with scale-up. Eventually, 500 nM of the MTX-resistant pool lines was obtained.

6. Detection of Recombinant Human Protein S Secreted and Expressed in Culture Supernatant From 500 nM of the plural MTX-resistant pool lines obtained in the above section 5, $1.0 \times 10^6$ cells of each cell line was suspended in IMDM medium supplemented with 5 mL of dialyzed fetal bovine serum at a final concentration of 10%, 50 μg/mL of gentamicin and 500 nM of MTX, and seeded in T25 flasks, followed by culturing. Three days after the culturing, the culture supernatant was recovered, and an amount of recombinant human Protein S contained in the supernatant was measured by ELISA using a Matched-Pair Antibody Set for human Protein S antigen (manufactured by Affinity Biologicals). Phosphate Buffered Saline (PBS) containing 0.05% Tween20 was used as wash buffer, buffer containing 1% bovine serum albumin (BSA) and 0.1% Tween20 as sample dilution buffer, 3,3',5,5'-tetramethyl benzidine (TMB: manufactured by Sigma) as a color development substrate solution, and 1M $H_2SO_4$ as a color development stop solution. As a standard, human plasma-derived Protein S (manufactured by Calbiochem) was used. By such an analysis, it was confirmed that recombinant human Protein S is expressed at a concentration of 1 μg/mL or more in the culture supernatant of 500 nM plural MTX-resistant pool lines.

Example 3

Purification of Recombinant Human Protein S Protein

1. Collection of Culture Supernatant Containing Recombinant Human Protein S

The recombinant human Protein S-producing cell line obtained in Example 2 was suspended in IMDM medium supplemented with 10% dialyzed fetal bovine serum, 50 μg/mL of gentamicin and 500 nM of MTX, and seeded in tissue culture flasks (manufactured by Greiner). The cells were cultured for several days, followed by confirming the growth of cells to confluence, and the supernatant of each flask was discarded and the cells were washed twice with 10 mL of PBS. Immediately thereafter, 30 mL of an EX-CELL302 medium (manufactured by JRH) containing 6 mM L-glutamine and 500 nM MTX was added to the cells which were then cultured. After 5-day culture, the culture supernatant was recovered and filtered through a 0.22 μm bottle top filter (manufactured by Iwaki). As a result, 150 mL of the culture supernatant containing recombinant human Protein S was obtained.

2. Purification of Recombinant Protein S

Purification of Protein S was carried out with reference to the method described in the literature [*Thromb Haemost.*, 91, 1105, 2004] and the literature [*Thromb Haemost.*, 77, 1156, 1997]. For the culture supernatant containing recombinant Protein S obtained in the above 1, the buffer was replaced with PBS by diafiltration method using an ultrafiltration membrane (fraction molecular weight: 10,000, made of polyethersulfone, manufactured by Millipore). EDTA was added to the obtained sample (about 110 mL) so as to be at a final concentration of 5 mM. The sample was purified by calcium an elution anion exchange chromatography. A Q sepharose FF column (1.0 mL, manufactured by GE Healthcare) was used as a purification column. The column was equilibrated with equilibration buffer containing 150 mM NaCl, 5 mM EDTA, and 20 mM Tris (hydroxymethyl)aminomethane (pH 7.4). The sample was adsorbed onto the Q sepharose FF column by supplying 20 mL of the sample at a flow rate of 1.0 mL/min. The column was washed by supplying 15 column volumes (CV) of the equilibration buffer, and also supplying 15 CVs of a buffer containing 150 mM NaCl and 20 mM Tris (pH 7.4). Elution was carried out by supplying 10 CVs of an elution buffer containing 150 mM NaCl, 20 mM $CaCl_2$, and 20 mM Tris (pH 7.4). The column was washed and regenerated by supplying 5 CVs of a buffer containing 500 mM NaCl and 20 mM Tris (pH 7.4), and 5 CVs of a buffer containing 1 mM NaCl and 20 mM Tris (pH 7.4). Using an AKTA purifier system (manufactured by GE Healthcare) as a chromatography equipment, at a pump flow rate of 0.5 mL/min except adsorption of the sample, elution fractions were collected at every 250 μL. The solvent material was detected by measuring the absorbance at 280 nm, 260 nm, and 320 nm. The same procedure was repeated 5 times for the purification of Protein S. Subsequently, the elution fractions were combined, and the buffer exchange with 150 mM NaCl and 20 mM Tris (pH 7.4) and the volume concentration to 1.8 mL were carried out by diafiltration using an ultrafiltration membrane (fraction molecular weight: 10,000, made of polyethersulfone, manufactured by Millipore). In addition, EDTA was added thereto to be a final concentration of 25 mM.

Next, the sample was subjected to salt concentration elution anion exchange chromatography. A Q sepharose FF column (1.0 mL, manufactured by GE Healthcare) was used as a purification column. The column was equilibrated with an equilibration buffer containing 150 mM NaCl, 5 mM EDTA, and 20 mM Tris (pH 7.4). The sample was adsorbed onto the Q sepharose FF column was by supplying 800 μL of the sample. The column was washed by supplying 15 CVs of the equilibration buffer, and also supplying 15 CVs of a buffer containing 150 mM NaCl and 20 mM Tris (pH 7.4). Elution was carried out by supplying 15 CVs of an elution buffer containing 320 mM NaCl and 20 mM Tris (pH 7.4), 15 CVs of an elution buffer containing 400 mM NaCl and 20 mM Tris (pH 7.4), and 15 CVs of an elution buffer containing 500 mM NaCl and 20 mM Tris (pH 7.4). The column was washed and regenerated by supplying 5 CVs of a buffer containing 1M NaCl and 20 mM Tris (pH 7.4). Using an AKTA purifier system (manufactured by GE Healthcare) as a chromatography equipment, at a pump flow rate of 1.0 mL/min, elution fractions were collected at every 15 mL. The solvent material was detected by measuring the absorbance at 280 nm, 260 nm, and 320 nm. Subsequently, the elution fractions were combined, and buffer exchange with 150 mM NaCl and 20 mM Tris (pH 7.4) and the volume concentration to 1.0 mL were carried out by diafiltration using an ultrafiltration membrane (fraction molecular weight: 10,000, made of polyethersulfone, manufactured by Millipore).

Next, the sample was subjected to gel filtration chromatography. A Superdex 75 10/30 column (manufactured by GE Healthcare) was used as a purification column. The column-passing liquid was 150 mM NaCl, 20 mM Tris (pH7.4), and an applied amount of the sample was set to 200 μL. Using an AKTA purifier system (manufactured by GE Healthcare) as a chromatography equipment, at a pump flow rate of 0.5 mL/min, elution fractions were collected at every 15 mL. The solvent material was detected by measuring the absorbance at 280 nm, 260 nm, and 320 nm. The purified product of recombinant human Protein S obtained from the FUT8 knockout CHO/DG44 cells was hereinafter referred to simply as MSPS, and the purified product of recombinant human Protein S obtained from the CHO/DG44 cells was hereinafter referred to simply as KCPS.

Figure 4:
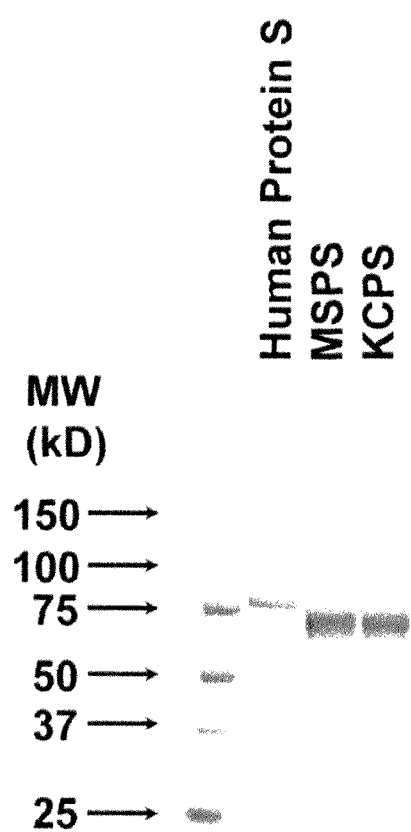
FIG. 4 shows the analysis results of a purified product of recombinant Protein S. Left shows the figure of each sample of MSPS and KCPS obtained by purification which were stained by Coomassie Brilliant Blue (CBB) after SDS-polyacrylamide electrophoresis. Right shows results of Western blotting. As positive control, human serum-derived Protein S was used.
Figure 4:
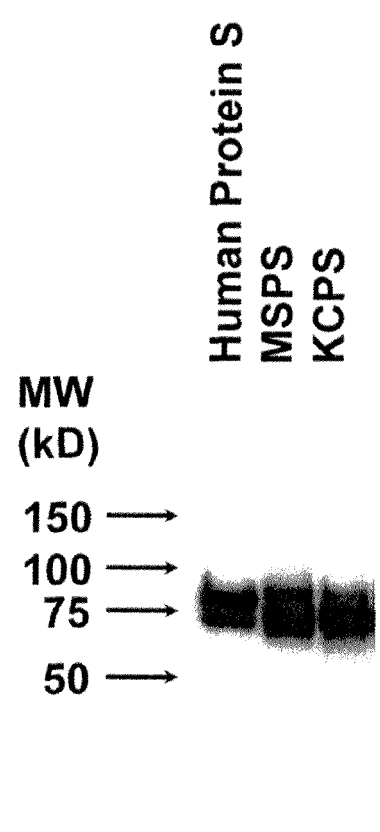

According to the results of SDS-polyacrylamide electrophoresis (PAGE) analysis and Western analysis of the obtained Protein S compositions, it was demonstrated that any sample contains Protein S with a purity of 95% or more (FIG. 4). For Western blotting analysis, the primary antibody was a goat anti-human Protein S antibody (manufactured by R&D Systems), and the secondary antibody was an HRP-labeled donkey anti-goat IgG antibody (manufactured by Chemicon).

Example 4

Analysis of Sugar Chain Structures of Recombinant Protein S

In accordance with the procedure described in Example 1, neutral sugar and amino sugar composition analysis and sialic acid analysis were carried out. In MSPS prepared in Example 3, composition ratios of individual monosaccharides, calculated based on a composition ratio of mannose=3.00, were 4.92 for N-acetylglucosamine (GlcNAc), 3.51 for galactose, and 2.13 for sialic acid, respectively. Fucose was not detected. Further, in KCPS prepared in Example 3, composition ratios of individual monosaccharides, calculated based on a composition ratio of mannose=3.00, were 0.69 for fucose, 4.34 for N-acetylglucosamine (GlcNAc), 3.06 for galactose, and 2.03 for sialic acid, respectively. The analysis results are given in Table 1 below.

TABLE 1

| | Neutral Sugar/ Amino Sugar Anaylsis* | | | | Acidic Sugar Analysis** Sialic Acid Number | N-terminal Analysis Presence/ Absence of Gla |
|---|---|---|---|---|---|---|
| | Fuc | GlcNAc | Gal | Man | | |
| Human Plasma Protein S | 0.26 | 4.53 | 2.80 | 3.00 | 6.3 | Present |
| MSPS | Not Detected | 4.92 | 3.51 | 3.00 | 6.4 | Present |
| KCPS | 0.69 | 4.34 | 3.06 | 3.00 | 6.1 | Present |

*composition ratios of neutral sugar and amino sugar when a composition ratio of mannose = 3.00
**addition number of sialic acid/molecule of Protein S Regarding the sugar chains, Fuc: fucose, GlcNAc: N-acetylglucosamine, Gal: galactose, and Man: mannose, and regarding the amino acid modification, Gla: γ-carboxylated glutamic acid.

Further, the profiling analysis of N-glycoside-linked sugar chains found that all of the sugar chains detected in both of MSPS and KCPS are complex type sugar chains, and a main sugar chain is a biantennary branched sugar chain (complex biantennary oligosaccharide) having sialic acid in the non-reducing end thereof. The MSPS-derived sugar chain exhibited no detection of a complex type sugar chain in which fucose is added to GlcNAc in the reducing end in the sugar chain.

From these results, it can be seen that all of the main complex type N-glycoside-linked sugar chains contained in the human plasma-derived Protein S, MSPS and KCPS, are complex biantennary oligosaccharides having sialic acid in the non-reducing end thereof. Further, an addition ratio of fucose to GlcNAc in the reducing end of the sugar chain was highest in KCPS, followed by human plasma-derived Protein S, and MSPS exhibited a fucose addition ratio of 0%.

In addition, by amino acid sequence analysis using Edman degradation, it was found that MSPS and KCPS, similar to human plasma-derived Protein S, contain γ-carboxylated glutamic acid (Gla) in the Gla domain at the amino terminal (Table 1), and the amino acid sequence of the amino terminal is identical with that of human plasma-derived Protein S.

Example 5

Analysis of Binding Capacity of Human Plasma-Derived Protein S for RAGE (by Surface Plasmon Resonance)

Using an amine coupling kit (manufactured by Biacore), human plasma-derived Protein S (manufactured by Calbiochem), human plasma-derived complement C4 binding protein (C4BP; manufactured by BioMed), and human plasma-derived complement C1 inhibitor Berinert P (manufactured by CSL Behring) were respectively immobilized on flow cells of a CM5 sensor chip (manufactured by Biacore). An immobilized amount of the ligand protein on the respective flow cells was set to the range of 2400 to 3600 resonance units (hereinafter referred to as "RU"). The complement C4 binding protein and the complement C1 inhibitor are known as plasma glycoproteins having the anti-inflammatory effect. Then, a recombinant human RAGE-Fc fusion protein (manufactured by R&D Systems) diluted to given concentrations (50000, 25000, 12500, 6250, 3125, and 1562 ng/mL) using HBS-EP+buffer (manufactured by Biacore), as an analyte, was allowed to run and bind to the ligand-immobilized flow cells at a temperature of 25° C., a flow rate of 5 μL/min, association time of 140 seconds, and dissociation time of 240 seconds. The chip was regenerated by a flow of an aqueous glycine solution (pH 1.5) (manufactured by Biacore) for 60 seconds.

Figure 5:
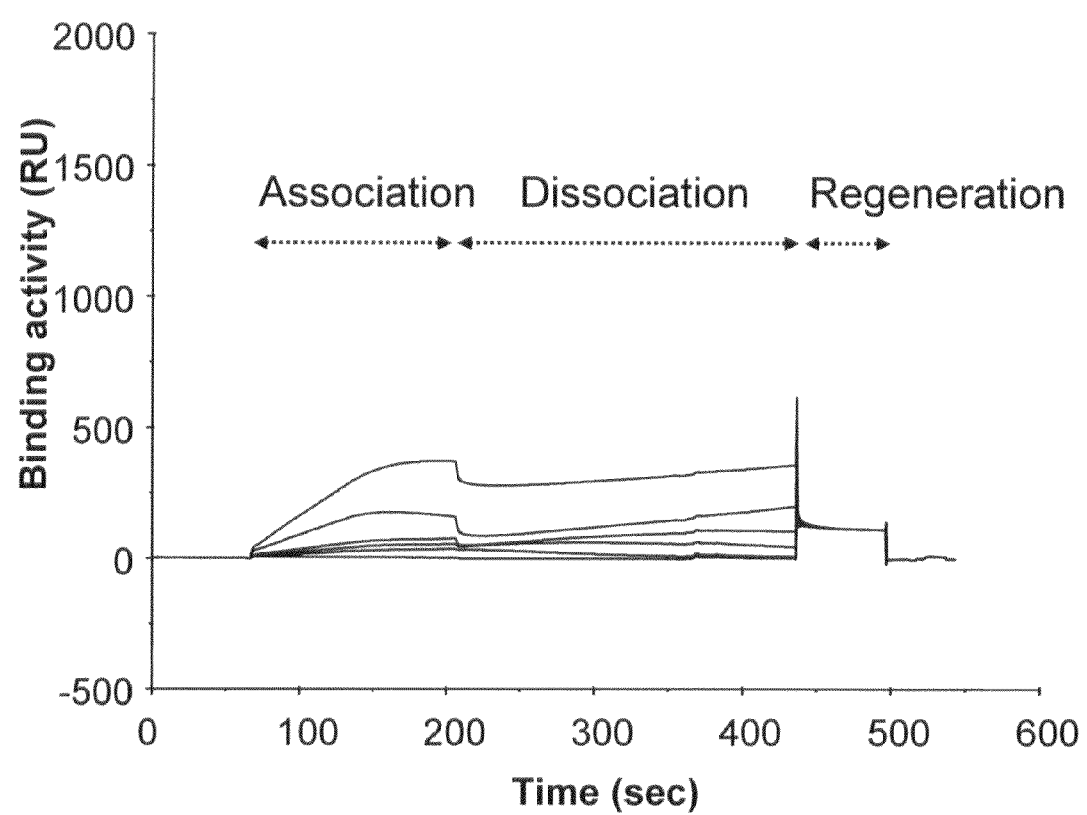
FIG. 5 shows the analysis results of a binding activity of a receptor for advanced glycation end products (RAGE) to human plasma-derived Protein S, as measured by surface plasmon resonance. The abscissa represents time (second), and the ordinate represents a binding activity of RAGE to Protein S on a sensor chip of Biacore T100. From the top, each sensorgram represents a value obtained at the time when RAGE was allowed to run at concentrations of 50000, 25000, 12500, 6250, 3125 and 0 ng/mL.

As a result, it was found that Protein S and human RAGE-Fc fusion protein were bounded (FIG. 5). On the other hand, the human RAGE-Fc fusion protein exhibited no binding to the complement C4 binding protein and the complement C1 inhibitor. Further, similar to Fc of human IgG 1 contained in the human RAGE-Fc fusion protein, an Fc-bearing protein, human E-selectin Fc fusion protein (manufactured by R&D systems), exhibited no binding property to Protein S.

Next, using an amine coupling kit (manufactured by Biacore), human plasma-derived Protein S (manufactured by Calbiochem), recombinant human activated protein C preparation Xigris (manufactured by Eli Lilly), and human plasma-derived sex hormone-binding globulin (SHBG) (manufactured by Scipac) were respectively immobilized on flow cells of a CM5 sensor chip (manufactured by Biacore). An immobilized amount of the ligand protein on the respective flow cells was set to the range of 2000 to 3000 RU. Activated protein C and sex hormone-binding globulin are known as plasma glycoproteins having relatively high homology to Protein S, among the human proteins. Then, a recombinant human RAGE-Fc fusion protein (manufactured by R&D Systems) diluted to given concentrations (50000, 25000, 12500, 6250, 3125, and 1562 ng/mL) using HBS-EP+buffer (manufactured by Biacore), as an analyte, was allowed to run and bind to the ligand-immobilized flow cells at a temperature of 25° C., a flow rate of 5 µL/min, association time of 140 seconds, and dissociation time of 240 seconds. The chip was regenerated by a flow of an aqueous glycine solution (pH 1.5) (manufactured by Biacore) for 60 seconds.

Figure 6:
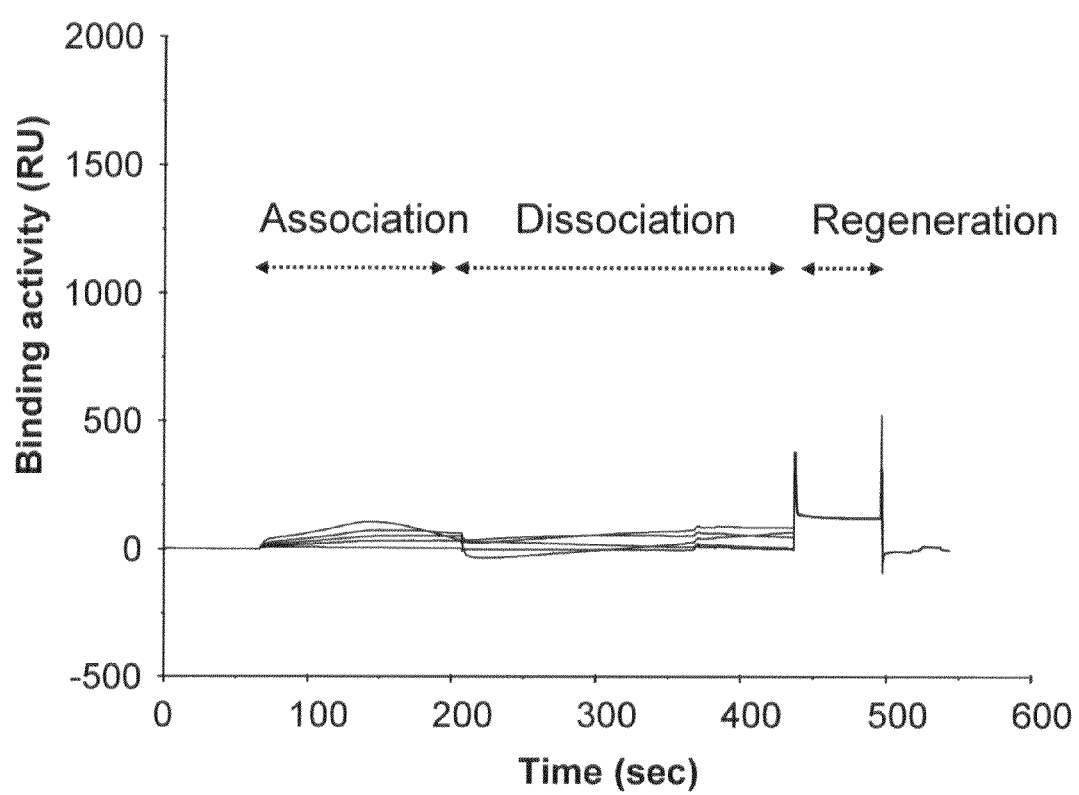
FIG. 6 shows the analysis results of a binding activity of a receptor for advanced glycation end products (RAGE) to human plasma derived-sex hormone-binding globulin (SHBG), as measured by surface plasmon resonance. The abscissa represents time (seconds), and the ordinate represents a binding activity of RAGE to SHBG on a sensor chip of Biacore T100. From the top, the sensorgram represents a value obtained at the time when RAGE was allowed to run at concentrations of 50000, 25000, 12500, 6250, 3125 and 0 ng/mL.

As a result, it was found again that Protein S and human RAGE-Fc fusion protein were bounded. On the other hand, the human RAGE-Fc fusion protein exhibited no binding to the recombinant human activated protein C and the human sex hormone-binding globulin. Typical reaction of SHBG not bound to RAGE is shown in FIG. 6. From these results, it was demonstrated that the binding activity to RAGE is an intrinsic biological activity of Protein S.

Example 6

Analysis of Binding Activity of Recombinant Protein S for RAGE (by Surface Plasmon Resonance)

Figure 7:
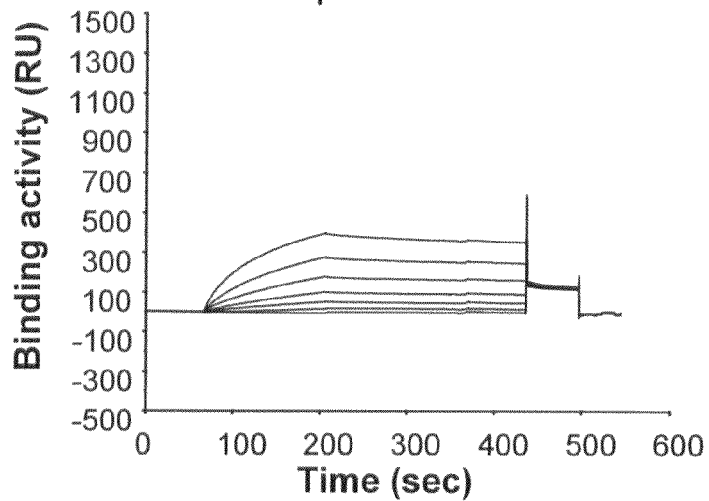
FIG. 7 shows the analysis results of a binding activity of an anti-human Protein S antibody (C-17) to Protein S, as measured by surface plasmon resonance. The abscissa represents time (seconds), and the ordinate represents a binding activity of a C-17 antibody to each Protein S on a sensor chip of Biacore T100. From the top, each sensorgram represents a value obtained at the time when C-17 was allowed to run at concentrations of 50000, 25000, 12500, 6250, 3125, 1562, and 0 ng/mL. The top, middle and bottom represent the binding of the C-17 antibody to human plasma Protein S, MSPS, and KCPS, respectively.
Figure 7:
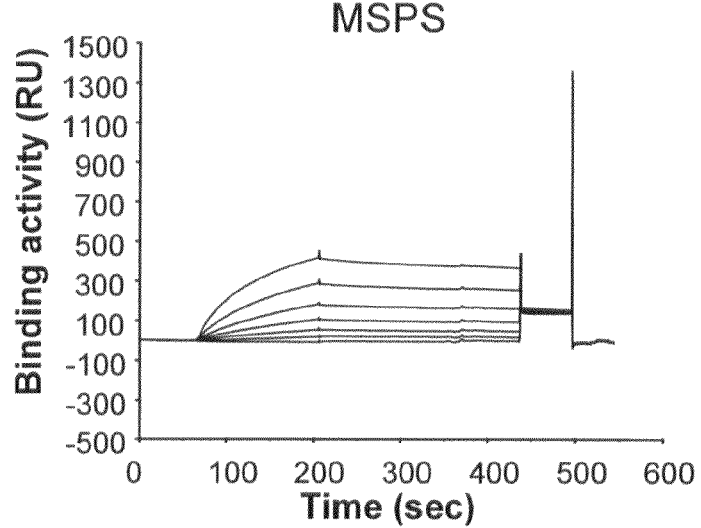
Figure 7:
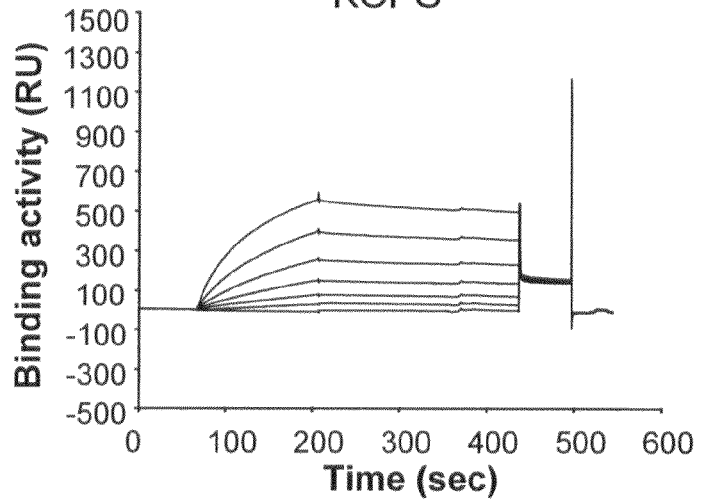

Using an amine coupling kit (manufactured by Biacore), human plasma-derived Protein S (manufactured by Calbiochem), and recombinant human Protein S prepared in Example 4, MSPS and KCPS were respectively immobilized on flow cells of a CM5 sensor chip (manufactured by Biacore). An immobilized amount of the ligand protein on the respective flow cells was set to the range of 1500 to 2000 RU. Then, an anti-human Protein S antibody C-17 (manufactured by Santa Cruz) (FIG. 7), or a human plasma-derived complement C4 binding protein (manufactured by BioMed) diluted to given concentrations (50000, 25000, 12500, 6250, 3125, and 1562 ng/mL) using HBS-EP+buffer (manufactured by Biacore), as an analyte, was allowed to run and bind to the ligand-immobilized flow cells at a temperature of 25° C., a flow rate of 5 µL/min, association time of 140 seconds, and dissociation time of 240 seconds. The anti-human Protein S antibody C-17 and the human plasma-derived complement C4 binding protein are known to bind to the sex hormone-binding globulin-like domain (SHBG domain) at the carboxyl terminal of Protein S. The chip was regenerated by a flow of an aqueous glycine solution (pH 1.5) (manufactured by Biacore) for 60 seconds. Dissociation constants calculated by analysis of the obtained data using Biacore T100 evaluation software ver 1.1 (manufactured by Biacore) are given in Table 2 below.

TABLE 2

|  | C-17 antibody | Human C4BP |
|---|---|---|
| Human plasma Protein S | 2.3 | 10.1 |
| MSPS | 2.4 | 9.2 |
| KCPS | 2.2 | 8.1 |
|  | ×10E−7 [M] | ×10E−8 [M] |

As a result, it was confirmed that both of anti-human Protein S antibody C-17 (FIG. 7) and human plasma-derived complement C4 binding protein exhibit equal binding capacity for three types of Protein S immobilized on the chip.

Figure 8:
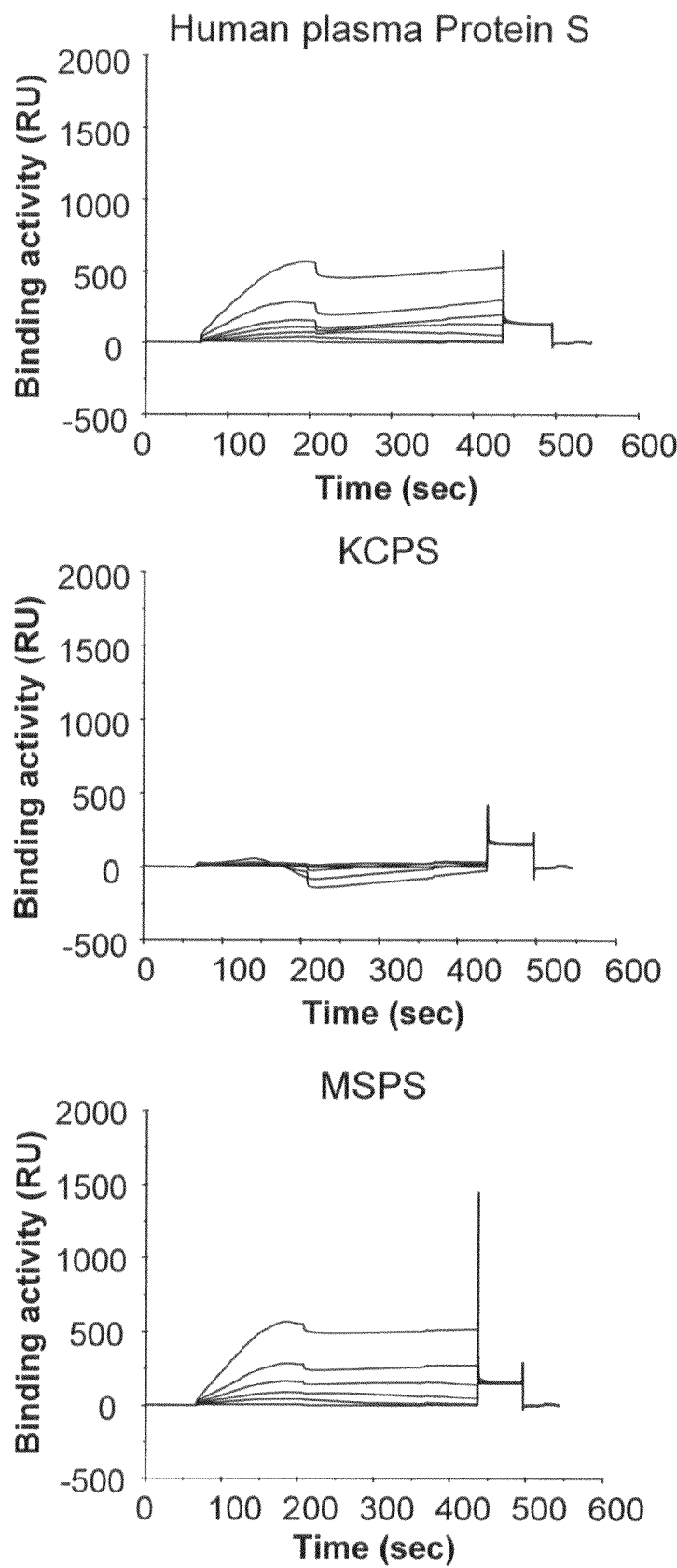
FIG. 8 shows the analysis results of a binding activity of RAGE to Protein S, as measured by surface plasmon resonance. The abscissa represents time (seconds), and the ordinate represents a binding activity of RAGE to each Protein S on a sensor chip of Biacore T100. From the top, the sensorgram represents RAGE concentrations of 50000, 25000, 12500, 6250, 3125, 1562 and 0 ng/mL. The top, middle and bottom represent the binding of RAGE to human plasma Protein S, KCPS, and MSPS, respectively.

Then, a recombinant human RAGE-Fc fusion protein (manufactured by R&D Systems) diluted to given concentrations (50000, 25000, 12500, 6250, 3125, and 1562 ng/mL) using HBS-EP+buffer (manufactured by Biacore), as an analyte, was allowed to run and bind to the ligand-immobilized flow cells at a temperature of 25° C., a flow rate of 5 µL/min, association time of 140 seconds, and dissociation time of 240 seconds (FIG. 8). The chip was regenerated by a flow of an aqueous glycine solution (pH 1.5) (manufactured by Biacore) for 60 seconds.

As a result, MSPS exhibited significantly higher binding property to RAGE than human plasma-derived Protein S. Binding parameters calculated by kinetic analysis of the obtained data using Biacore T100 evaluation software ver 1.1 (manufactured by Biacore) are given in Table 3 below.

TABLE 3

|  | Association Rate Constant ka ×10E5 [1/Ms] | Dissociation Rate Constant kd [1/s] | Dissociation Constant $K_D$ [nM] |
|---|---|---|---|
| Human plasma Protein S | 1.6 | 0.008 | 49 |
| MSPS | 51 | 0.04 | 7.5 |
| KCPS | Not Determined | Not Determined | Not Determined |

It was found that the affinity of MSPS for RAGE was about 7-fold higher than that of human plasma Protein S for RAGE. Further, KCPS exhibited substantially no binding property to the human RAGE-Fc fusion protein (FIG. 8).

From these results, it was demonstrated that the fucose residue bound to GlcNAc in the reducing end of the complex type N-glycoside-linked sugar chain contained in Protein S is a factor which significantly inhibits the binding of Protein S to RAGE.

Example 7

Analysis of Inhibitory Activity of Fucose-Free Recombinant Protein S on Binding Between HMGB-1 and RAGE, and between Mac-1 and Rage (by Surface Plasmon Resonance)

Using an amine coupling kit (manufactured by Biacore), recombinant human HMGB-1 (manufactured by R&D Systems), recombinant human Mac-1 heterodimer (αmβ2 integrin, CD11b/CD18; manufactured by R&D Systems), and recombinant human S100A8/A9 (manufactured by R&D Systems) were respectively immobilized at 200 RU, 1200 RU, and 400 RU on flow cells of a Series S C1 sensor chip (manufactured by Biacore). The measurement was carried out in the same manner as in Example 5, except that the recombinant human RAGE-Fc fusion protein (manufactured by R&D Systems) diluted to given concentrations of 50000, 5000 or 500 ng/mL was used as an analyte. As a result, it was recognized that all of the flow cells, on which HMGB-1, Mac-1 and S100A8/A9 were immobilized, exhibited a significant increase in the reactivity in concentration-dependent manner of RAGE.

Next, using the same sensor chip, the same binding experiment was carried out using a recombinant human RAGE-Fc fusion protein (5000 ng/mL) mixed with MSPS (final concentration of 50000 and 5000 µg/mL), as an analyte.

As a result of this analysis, all of the flow cells, on which HMGB-1, Mac-1 and S100A8/A9 were immobilized, exhibited a significant decrease in the reactivity of RAGE-Fc fusion protein in concentration-dependent manner of MSPS. In addition, the binding activity of MSPS (final concentration of 50000 pg/mL) to each of HMGB-1, Mac-1 and S100A8/A9 was confirmed using the same sensor chip, and a significant binding activity was not recognized.

Taken together, it was demonstrated that MSPS, through the specific binding to RAGE, has an activity to inhibit all the binding of RAGE to HMGB-1, Mac-1 or S100A8/A9 (RAGE neutralizing activity).

Example 8

Analysis of Inhibitory Activity of Recombinant Protein S on Binding Between HMGB-1 and RAGE and Between Mac-1 and Rage (by Surface Plasmon Resonance)

Using an amine coupling kit (manufactured by Biacore), HMGB-1 (manufactured by Wako Pure Chemical), and recombinant human Mac-1 heterodimer ($\alpha m\beta 2$ integrin, CD11b/CD18; manufactured by R&D systems) were respectively immobilized at 160 RU and 620 RU on flow cells of a Series S C1 sensor chip (manufactured by Biacore). Then, the experiment was carried out in the same manner as in Example 5, using the recombinant human RAGE-Fc fusion protein (5000 ng/mL) mixed with MSPS and KCPS (final concentration of 100, 10, and 1 µg/mL) prepared in Example 3, as an analyte.

Figure 9:
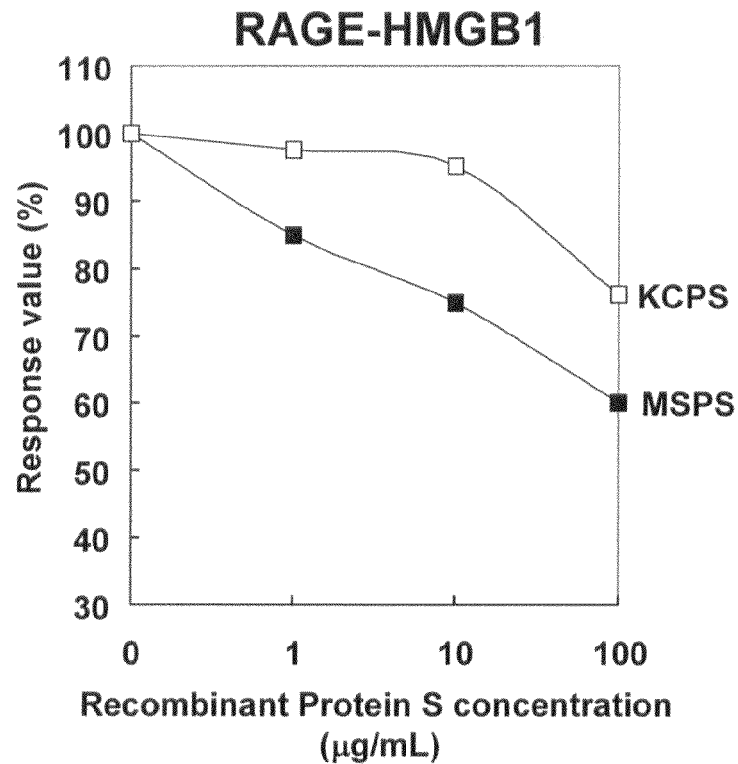
FIG. 9 shows the neutralizing action of recombinant Protein S (MSPS and KCPS) in the binding reaction of RAGE (5000 ng/mL) with HMGB-1 or Mac-1, as measured by surface plasmon resonance. The abscissa represents a concentration of Protein S (µg/mL). The ordinate represents a relative response value (%) when a response value immediately after the injection of an analyte (RAGE) in the absence of Protein S was regarded as 100%. The top and the bottom represent the concentration-dependent neutralizing activity of recombinant Protein S in the binding reaction of RAGE-HMGB1 and RAGE-Mac-1, respectively.
the RAGE-HMGB-1 binding and the bottom represents.
Figure 9:
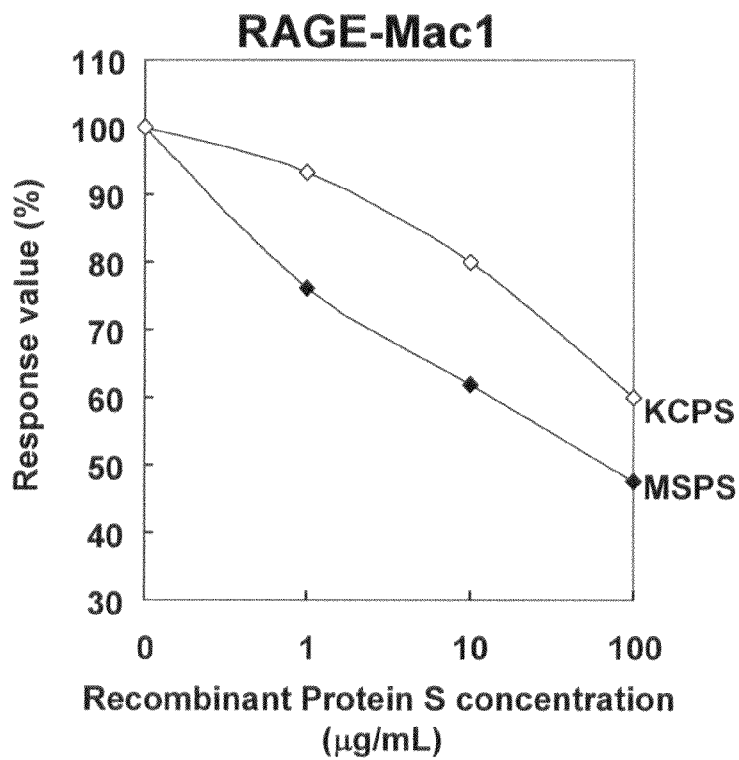

As a result of this analysis, any flow cell of HMGB-1 and Mac-1 exhibited a significant decrease in the binding of recombinant human RAGE-Fc fusion protein in concentration-dependent manner of MSPS and KCPS. FIG. 9 shows the relationship between Protein S concentration and the relative reactivity (%) which is measured by regarding the Biacore reactivity (RU: resonance unit) in the absence of Protein S as 100%. From this result, it was demonstrated that the inhibitory activity of MSPS against RAGE is stronger than the RAGE inhibitory activity of KCPS.

Example 9

Analysis of Binding Capacity of Recombinant Protein S for Cd14 (by Surface Plasmon Resonance)

Human CD14 is a single transmembrane glycoprotein belonging to the pattern recognition receptor family, similar to RAGE. When a ligand, lipopolysaccharide (LPS)-LPS binding protein (LBP) complex, binds to CD14, signals causing intracellular inflammatory responses are transferred to increase the production of HMGB-1 and the like. From these facts, similar to RAGE, CD14 is known as an inflammatory mediator in sepsis and the like. For these reasons, the experiment was carried out using Biacore T100 as described above, in order to confirm the binding activity of Protein S to CD14.

Using an amine coupling kit, human plasma-derived Protein S, and recombinant human Protein S prepared in Example 3, MSPS were respectively immobilized at 700 to 800 RU on flow cells of a Series S C1 sensor chip (manufactured by Biacore). Then, the experiment was carried out in the same manner as in Example 5, using a recombinant human CD14 protein (manufactured by R&D systems) diluted to given concentrations (25000, 12500, 6250, 3125, and 1562 ng/mL) using HBS-EP+buffer (manufactured by Biacore), as an analyte.

As a result, it was demonstrated that MSPS exhibits higher binding property to CD14 than KCPS and human plasma-derived Protein S.

Example 10

Figure 10:
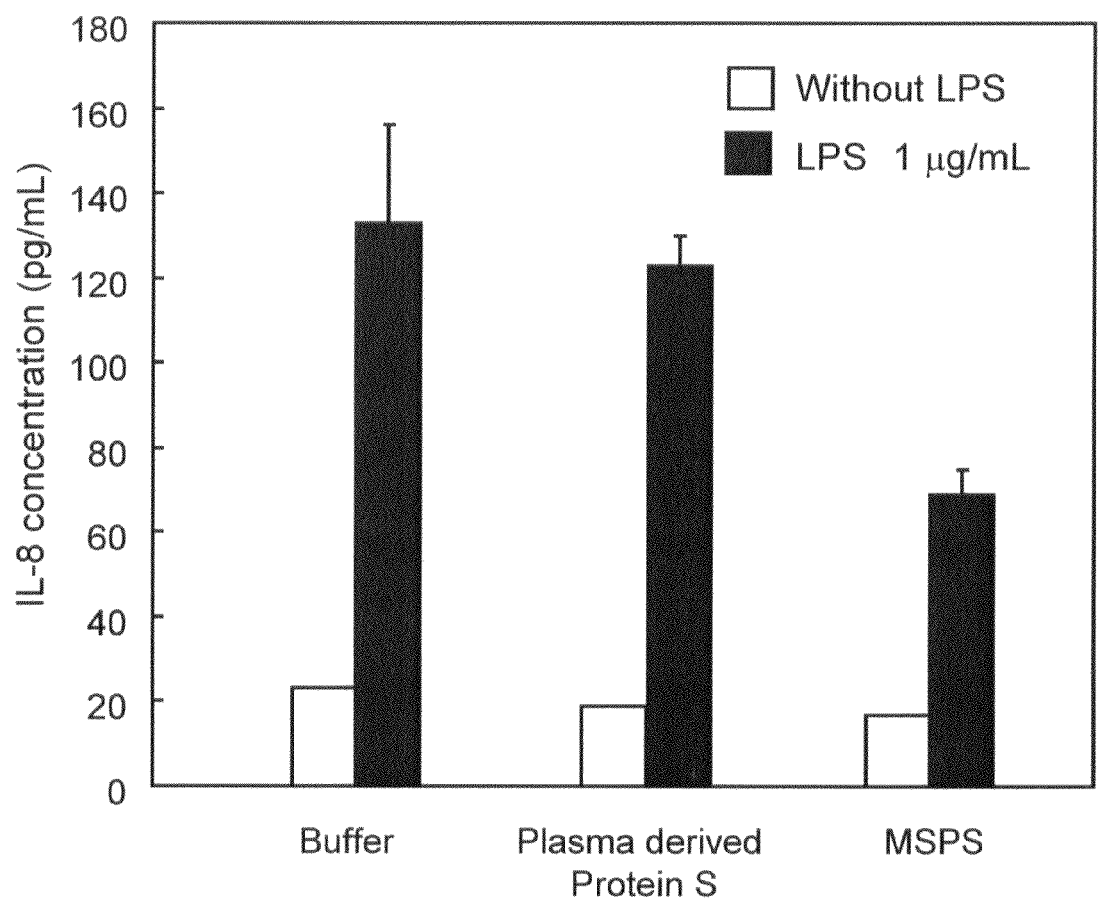
FIG. 10 shows inhibitory effects of recombinant Protein S on production of inflammatory cytokines from the activated vascular endothelium. An open column represents the inhibitory effect without induction with LPS and a solid column represents induction with LPS. The ordinate represents a production quantity of interleukin-8, and the abscissa represents the added Protein S.

Inhibitory Effects on Production of Inflammatory Cytokines from Activated Vascular Endothelium Human interleukin 8 (IL-8) is known as an inflammatory mediator that is produced largely by the activated vascular endothelium in sepsis, disseminated intravascular coagulation (DIC), and thrombosis such as VTE, and takes part in the pathogenic progression. Therefore, analysis was carried out to investigate whether recombinant Protein S has inhibitory effects on the production of IL-8 from vascular endothelial cells. Normal human umbilical vein endothelial cells (HUVECs; manufactured by Lonza) cultured in a low-serum medium for vascular endothelial cells (manufactured by Kurabo) were seeded at a density of $8.3 \times 10^4$ cells/well to a 96-well cell culture plate (manufactured by Becton, Dickinson and Company). After culturing for 48 hours, the culture medium was exchanged with a vascular endothelium cell-directed serum-free medium, and Protein S at a final concentration of 20 µg/mL was added thereto, followed by culturing at 37° C. for 2 hours. Then, *Salmonella*-derived lipopolysaccharide (LPS; manufactured by Sigma) at a final concentration of 1 µg/mL was added thereto, followed by culturing at 37° C. for 20 hours. On next day, 180 µL of the culture supernatant of each well was recovered, and a concentration (unit: pg/mL) of IL-8 in the culture supernatant was measured using a human IL-8-specific ELISA kit (manufactured by Bender MedSystems) in accordance with the manual attached thereto (FIG. 10).

As a result, a background value under no addition of LPS was 23.4 pg/mL in a well with no addition of Protein S, 18.9 pg/mL in a well with the addition of human plasma-derived Protein S, and 16.6 pg/mL in a well with the addition of MSPS, respectively. On the other hand, a concentration of IL-8 in the LPS-added well was 133.2 pg/mL in a well with no addition of Protein S, 123.2 pg/mL in a well with the addition of human plasma-derived Protein S, and 68.7 pg/mL in a well with the addition of MSPS, respectively. From these results, the possibility was suggested that fucose-free recombinant Protein S composition would have an inhibitory activity on the production of IL-8 from vascular endothelial cells, and the anti-inflammatory effect.

Example 11

Inhibitory Effects of Protein S on Adhesion of Human Monocytes to Activated Vascular Endothelium It is known that when inflammation in tissues is enhanced by human sepsis, acute lung injury, or the like, a variety of leukocytes including monocytes circulating in peripheral blood bind to the vascular endothelium, roll to adhere to the endothelial surface, and finally infiltrate into tissues, thus worsening inflammation. Accordingly, an investigation was carried out on whether the recombinant Protein S composition inhibits adhesion of human monocytes to the activated vascular endothelium.

Figure 11:
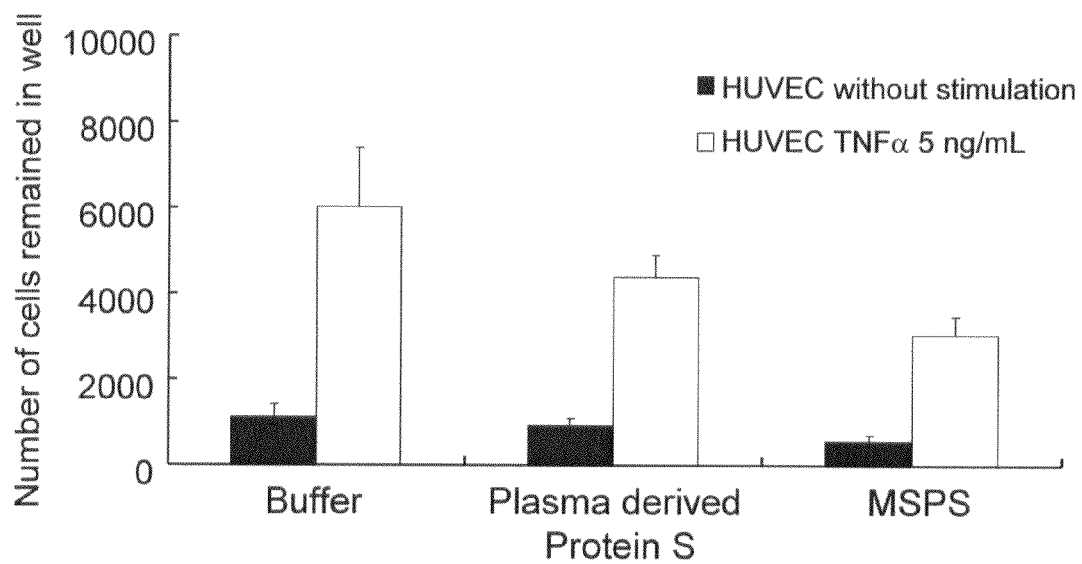
FIG. 11 shows inhibitory effects of Protein S on the adhesion between the human vascular endothelial cell line HUVEC and the human monocyte cell line (U-937). The abscissa represents the type of Protein S added to U-937 cells and the ordinate represents the number of U-937 cells adhered to HUVECs. An open column represents HUVECs with TNFα stimulation and a solid column represents HUVECs without TNFα stimulation. The top represents the neutralizing activity of Protein S on adhesion of TNFα- stimulated U-937 to HUVECs, and the bottom represents the neutralizing activity of Protein S on adhesion of HMGB-1-stimulated U-937 to HUVEC. Each data represents the mean value and standard deviation from three wells.
Figure 11:
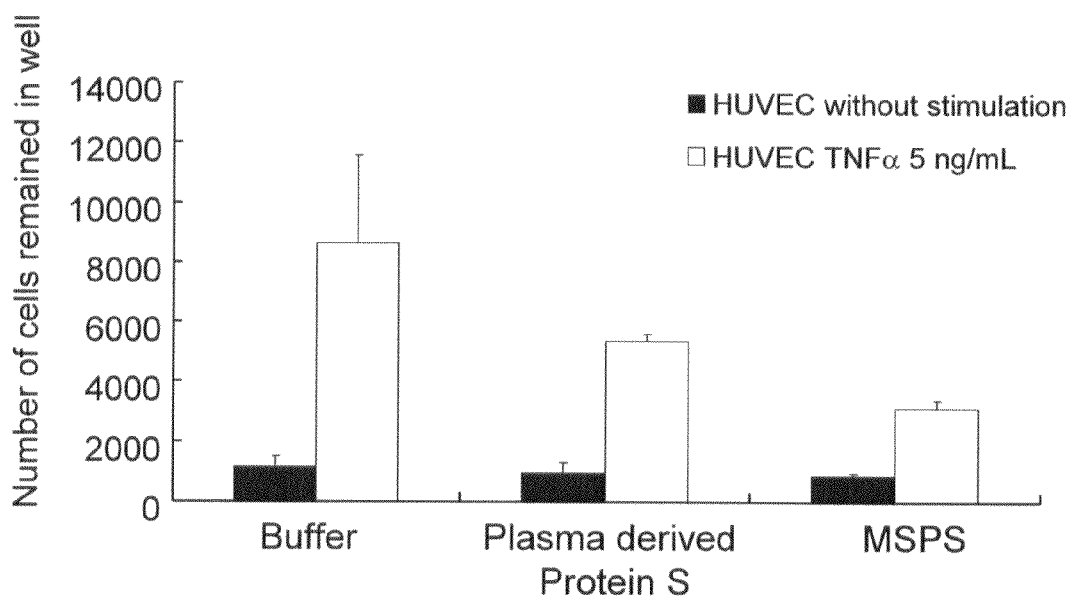

Normal human umbilical vein endothelial cells (HUVECs; manufactured by Lonza) cultured in a low-serum medium (manufactured by Kurabo) for vascular endothelial cells were seeded at a density of $2.0 \times 10^4$ cells/well to a 96-well cell culture plate (manufactured by Becton, Dickinson and Company). After culturing for 48 hours, human TNF-$\alpha$ (manufactured by R&D Systems) at a final concentration of 5 ng/mL was added to HUVECs in the wells, followed by culturing at 37° C. for 4 hours. On the other hand, the human monocyte-derived cell line U-937 cell (ATCC CRL-1593) cultured in an RPMI1640 medium (manufactured by Invitrogen) supplemented with 10% (v/v) fetal bovine serum was labeled with a fluorescent dye PKH67 (manufactured by Sigma). The fluorescent-labeled U-937 cells were suspended in an RPMI1640 medium (manufactured by Invitrogen; containing bovine serum albumin (BSA) at a final concentration of 0.1%) to which Protein S at a final concentration of 50 μg/mL was added, followed by culturing at 37° C. for 1 hour. Next, the U-937 cells were divided into two groups, to each of which HMGB (manufactured by Wako Pure Chemical) at a final concentration of 1 μg/mL, and human TNF-α at a final concentration of 5 ng/mL were added, followed by culturing at 37° C. for 4 hours. Then, 2.0×10⁴ cells/well of these U-937 cells were added to the culture plate where HUVECs had been cultured, followed by culturing at 37° C. for 1 hour for adhesion. Thereafter, each well was washed twice in the medium to remove U-937 cells which had not been adhered to HUVECs. The number of U-937 cells bound to HUVECs was quantified by measuring the fluorescence intensity (excitation: 490 nm, and emission: 535 nm) of wells using a fluorescence plate reader ARVO (manufactured by Perkin-Elmer) (FIG. 11).

As a result of this analysis, it was demonstrated that Protein S inhibits the adhesion of TNFα or HMGB-1-dependently activated U-937 cells to the activated HUVECs. Further, MSPS exhibited remarkably higher adhesion inhibitory effects than human plasma-derived Protein S. From these results, the possibility was suggested that the fucose-free recombinant Protein S composition would have a strong inhibitory activity of cell adhesion, that is, the potent anti-inflammatory effect.

While the invention has been described in detail and with reference to specific embodiments thereof, it will be apparent to one skill in the art that various changes and modifications can be made therein without departing from the spirit and scope thereof.

This application is based on Japanese application No. 2008-208384, filed on Aug. 13, 2008, and U.S. provisional application No. 61/089,271, filed on Aug. 15, 2008, the entire contents of which are incorporated hereinto by reference. All references cited herein are incorporated in their entirety.

What is claimed is:

1. An isolated Protein S composition comprising recombinant Protein S molecules having complex type N-glycoside-linked sugar chains,
wherein said recombinant Protein S molecules comprise an amino acid sequence having 95% or more amino acid sequence identity to the amino acid sequence of SEQ ID NO: 8,
and wherein the proportion of the total complex type N-glycoside-linked sugar chains on said recombinant Protein S molecules that lack fucose is greater than the proportion of the total complex type N-glycoside-linked sugar chains on native Protein S present in healthy human blood that lack fucose.

2. The isolated Protein S composition according to claim 1, wherein
(A) the complex type N-glycoside-linked sugar chains are sugar chains in which fucose is not bound to N-acetylglucosamine in the reducing end in the sugar chains;
(B) the complex type N-glycoside-linked sugar chains are sugar chains in which sialic acid is bound to galactose in the non-reducing end in the sugar chains;
(C) the complex type N-glycoside-linked sugar chains are sugar chains which bind to at least one asparagine residue at positions 458, 468 and 489 from the N-terminal of Protein S; and/or
(D) a sequence of amino acids at positions 1 to 45 from the N-terminal of Protein S is an amino acid sequence in which a side chain of at least one glutamic acid residue in the amino acid sequence is subjected to γ-carboxylation.

3. The isolated Protein S composition according to claim 1, wherein said recombinant Protein S molecules
comprise the amino acid sequence of SEQ ID NO: 8.

4. The Protein S composition according to claim 1, wherein said recombinant Protein S molecules are encoded by a DNA comprising the nucleotide sequence of SEQ ID NO: 7.

5. A cell which produces the recombinant Protein S molecules of claim 1.

6. The cell according to claim 5, wherein
(A) the cell is a cell in which its genome is modified so as to delete the activity of an enzyme relating to the synthesis of an intracellular sugar nucleotide, GDP-fucose;
(B) the cell is a cell in which its genome is modified so as to delete the activity of an enzyme relating to the modification of a sugar chain in which fucose is bound to N-acetylglucosamine in the reducing end through an α-bond in a complex type N-glycoside-linked sugar chain; and/or
(C) the cell is a cell which is resistant to a lectin recognizing a sugar chain structure in which the 1-position of fucose is bound to the 6-position of N-acetylglucosamine in the reducing end through an α-bond in a complex type N-glycoside-linked sugar chain.

7. The cell according to claim 6, wherein the enzyme relating to the synthesis of the intracellular sugar nucleotide, GDP-fucose is an enzyme selected from the group consisting of GDP-mannose 4,6-dehydratase and GDP-4-keto-6-deoxy-D-mannose-3,5-epimerase.

8. The cell according to claim 6, wherein the enzyme relating to the modification of a sugar chain in which fucose is bound to N-acetylglucosamine in the reducing end through an α-bond in a complex type N-glycoside-linked sugar chain is an enzyme selected from the group consisting of α1,6-fucosyltransferase and α1,3-fucosyltransferase.

9. A process for producing the Protein S composition according to claim 1, comprising culturing the cell described in claim 5 in a medium to produce and accumulate the Protein S composition described in claim 1 in the culture, and collecting the Protein S composition from the culture.

10. A pharmaceutical composition comprising the isolated Protein S composition according to claim 1 and a pharmaceutically acceptable carrier.

11. A method for preventing or treating a disease associated with deficiency or deletion of Protein S, comprising administering the Protein S composition according to claim 1.

12. The method according to claim 11, wherein the disease is inflammation.

13. The method according to claim 11, wherein the disease is sepsis.

14. The method according to claim 11, wherein the disease is thrombosis.

* * * * *